US009611301B2

(12) United States Patent
Stapleton et al.

(10) Patent No.: US 9,611,301 B2
(45) Date of Patent: Apr. 4, 2017

(54) GB VIRUS C (HEPATITIS G VIRUS) E2 GLYCOPROTEIN AS AN IMMUNOMODULATORY AGENT

(71) Applicants: THE UNIVERSITY OF IOWA RESEARCH FOUNDATION, Iowa City, IA (US); THE UNITED STATES OF AMERICA AS REPRESENTED BY THE DEPARTMENT OF VETERANS AFFAIRS, Washington, DC (US)

(72) Inventors: Jack T. Stapleton, Iowa City, IA (US); Nirjal Bhattarai, Coralville, IA (US); Jinhua Xiang, Iowa City, IA (US); James H. McLinden, Coralville, IA (US)

(73) Assignees: The University of Iowa Research Foundation, Iowa, IA (US); The United States of America as Represented by The Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/384,775

(22) PCT Filed: Mar. 13, 2013

(86) PCT No.: PCT/US2013/030665
§ 371 (c)(1),
(2) Date: Sep. 12, 2014

(87) PCT Pub. No.: WO2013/142167
PCT Pub. Date: Sep. 26, 2013

(65) Prior Publication Data
US 2015/0071955 A1    Mar. 12, 2015

Related U.S. Application Data

(60) Provisional application No. 61/613,298, filed on Mar. 20, 2012.

(51) Int. Cl.
*A61K 39/29* (2006.01)
*A61K 39/00* (2006.01)
(Continued)

(52) U.S. Cl.
CPC ............ *C07K 14/005* (2013.01); *A61K 38/00* (2013.01); *A61K 38/162* (2013.01); *A61K 45/06* (2013.01);
(Continued)

(58) Field of Classification Search
None
See application file for complete search history.

(56) References Cited

U.S. PATENT DOCUMENTS 6,156,495 A * 12/2000  Pilot-Matias et al. ............... C07K 14/005
                                          435/320.1
6,803,044 B1 * 10/2004 Catania ............... A61K 9/0034
                                          424/278.1

(Continued)

FOREIGN PATENT DOCUMENTS

ES   WO 2010116015 A1 * 10/2010  .......... A61K 38/162
WO   WO 0177157 A2 * 10/2001   ............ A61K 35/76
(Continued)

OTHER PUBLICATIONS

WO2010116015A1, Gomara et al. (2010)(Google Translation).*
(Continued)

*Primary Examiner* — Janet L Andres
*Assistant Examiner* — M. Franco Salvoza
(74) *Attorney, Agent, or Firm* — Parker Highlander PLLC

(57) ABSTRACT

GB virus C (GBV-C or hepatitis G virus) is a flavivirus that frequently leads to chronic viremia in humans. The invention provides compositions and methods involving GBV-C E2 polypeptides and peptides for use in modulating immune (Continued)

responses, including inhibition inflammation related to pathogenic T-cell activation.

19 Claims, 27 Drawing Sheets

(51) Int. Cl.
    *C07K 14/005*     (2006.01)
    *A61K 38/00*     (2006.01)
    *C07K 1/00*     (2006.01)
    *A61K 38/16*     (2006.01)
    *A61K 45/06*     (2006.01)
    *C12N 7/00*     (2006.01)

(52) U.S. Cl.
    CPC ............... *C07K 1/00* (2013.01); *C12N 7/00* (2013.01); *C07K 2319/10* (2013.01); *C12N 2770/24222* (2013.01); *C12N 2770/24233* (2013.01)

(56) References Cited

U.S. PATENT DOCUMENTS

| | | | |
|---|---|---|---|
| 2005/0118181 A1* | 6/2005 | Stapleton et al. ... | C07K 16/109 424/160.1 |
| 2005/0119472 A1 | 6/2005 | Stapleton et al. | |
| 2005/0147993 A1* | 7/2005 | Khan ................... | A61K 48/005 435/6.17 |
| 2009/0010932 A1 | 1/2009 | Stapleton et al. | |
| 2010/0143454 A1 | 6/2010 | McLinden et al. | |
| 2011/0104163 A1 | 5/2011 | Dimitrov et al. | |
| 2012/0058137 A1 | 3/2012 | Bonny | |

FOREIGN PATENT DOCUMENTS

| | | | |
|---|---|---|---|
| WO | WO 2005032595 A2 * | 4/2005 | ......... A61K 38/1709 |
| WO | WO 2013/142167 | 9/2013 | |

OTHER PUBLICATIONS

Lim et al., "Sequence variation and phylogenetic analysis of envelope glycoprotein of hepatitis G virus," Journal of General Virology 78: 2771-2777 (1997).*
Bhattarai et al., "GB virus C viremia is associated with higher levels of double-negative T cells and lower T-cell activation in HIV-infected individuals receiving antiretroviral therapy," *J Infect Dis*, 206(9):1469-1472 (2012).
Bhattarai, et al. "GB virus C: the good boy virus?" *Trends Microbiol.*, 20(3):124-30 (2012).
Bhattarai, et al. "GB virus C envelope protein E2 inhibits TCR-induced IL-2 production and alters IL-2-signaling pathways," *J. Immunol.*, 189(5):2211-2216 (2012).
Bhattarai, et al., "GB Virus C Particles Inhibit T Cell Activation via Envelope E2 Protein-Mediated Inhibition of TCR Signaling," *J. Immunol.*, 190(12) 6351-6359 (2013).
Chivero et al., "Human pegivirus RNA is found in multiple blood mononuclear cells in vivo and serum-derived viral RNA-containing particles are infectious in vitro," *Journal of General Virology*, 95(Pt 6):1307-1319 (2014).
Elssmann, et al., "Blocking the 6-helix-bundle Formation of HIV-1 gp41 by GBV-C E2-derived Peptides Mediates Inhibition of HIV-1 Entry," CROI Seattle (19th Conference on Retroviruses and Opportunistic Infections); Mar. 8, 2012; paper# 218; [Retrieved from the Internet May 28, 2013: <http://retroconference.org/2012b/Abstracts/43876.htm>].

Fernandez et al., "Synthetic peptides derived from an N-terminal domain of the E2 protein of GB virus C in the study of GBV-C/HIV-1 co-infection," *J. Peptide Sci.*, 18(5):326-335 (2012).
George et al., "Clinical isolates of GB virus type C vary in their ability to persist and replicate in peripheral blood mononuclear cell cultures," *Virology*, 316(2):191-201 (2003).
Haro et al. "Study of the inhibition capacity of an 18-mer peptide domain of GBV-C virus on gp41-FP HIV-1 activity." *Biochim. Biophys. Acta*, 1808(6):1567-73 (2011).
Herrera, et al. "Effect of synthetic peptides belonging to E2 envelope protein of GB virus C on human immunodeficiency virus type 1 infection." *J. Med. Chem.*, 53(16):6054-6063, S2, Supplemental Table 1, P25, P27, P28, P29; (2010).
Hotta et al., "Urine processing impacts uric acid level in HIV-infected adults: implications for diagnosing tenofovir-associated proximal tubulopathy," *AIDS* 27:1827-1832 (2013).
Jung, et al. "HIV entry inhibition by the envelope 2 glycoprotein of GB virus C." *AIDS*, 21(5):645-647 (2007).
Koedel et al., "Peptides derived from a distinct region of GB virus C glycoprotein E2 mediate strain specific HIV-1 entry inhibition," *J Virol.*; 85(14):7037-7047 (2011).
Landires et al., "HIV infection perturbs interleukin-7 signaling at the step of STAT5 nuclear relocalization," *AIDS*, 25(15):1843-1853 (2011).
Maidana-Giret et al., "GB virus type C infection modulates T-cell activation independently of HIV-1 viral load," *AIDS*, 23(17):2277-2287 (2009).
Mohr et al., "GB virus type C interactions with HIV: the role of envelope glycoproteins," *J Viral Hepat.*, 16(11): 757-768 (2009).
Mohr, "GB virus C: cellular interactions, HIV inhibition and natural history," PhD Thesis. May 2012. [Retrieved from the Internet May 28, 2013: <http://ir.uiowa.edu/cgi/viewcontent.cgi?article=3095&context=etd>].
PCT International Search Report and Opinion issued in PCT International Application No. PCT/US2013/030665, mailed on Jul. 11, 2013.
Rydze, et al., "GB virus C infection is associated with a reduced rate of reactivation of latent HIV and protection against activation-induced T-cell death," *Antivir Ther* 17(7): 1271-1279, (2012).
Schwarze-Zander et al. "Role of GB virus C in modulating HIV disease," *Expert Rev. Anti Infect Ther.*, 10(5): 563-72 (2012).
Stapleton et al., "GB virus C infection is associated with altered lymphocyte subset distribution and reduced T cell activation and proliferation in HIV-infected individuals," *PLoS One* 7(11): e50563 (2012).
Stapleton et al., "GBV-C viremia is associated with reduced CD4 expansion in HIV-infected people receiving HAART and interleukin-2 therapy," *AIDS*, 23(5):605-610 (2009).
Stapleton et al., "The GB viruses: a review and proposed classification of GBV-A, GBV-C (HGV), and GBV-D in genus *Pegivirus* within the family Flaviviridae," *J. Gen. Virol.*, 92(Pt 2):233-246 (2011).
Stapleton et al., "A Novel T Cell Evasion Mechanism in Persistent RNA Virus Infection," *Trans Am Clin Climatol Assoc.*, 125:14-24 (2014).
Xiang et al. "Characterization of a peptide domain within the GB virus C envelope glycoprotein (E2) that inhibits HIV replication," *Virology* 430(1):53-62 (2012).
Xiang et al., "An 85-aa segment of the GB virus type C NS5A phosphoprotein inhibits HIV-1 replication in CD4+ Jurkat T cells," *Proc. Natl. Acad. Sci USA*, 103(42):15570-15575 (2006).
Zimmerli et al., "HIV-1-specific IFN-.gamma./IL-2-secreting CD8 T cells support CD4-independent proliferation of HIV-1-specific CD8 T cells," *PNAS USA*, 102(20):7239-7244 (2004).

* cited by examiner

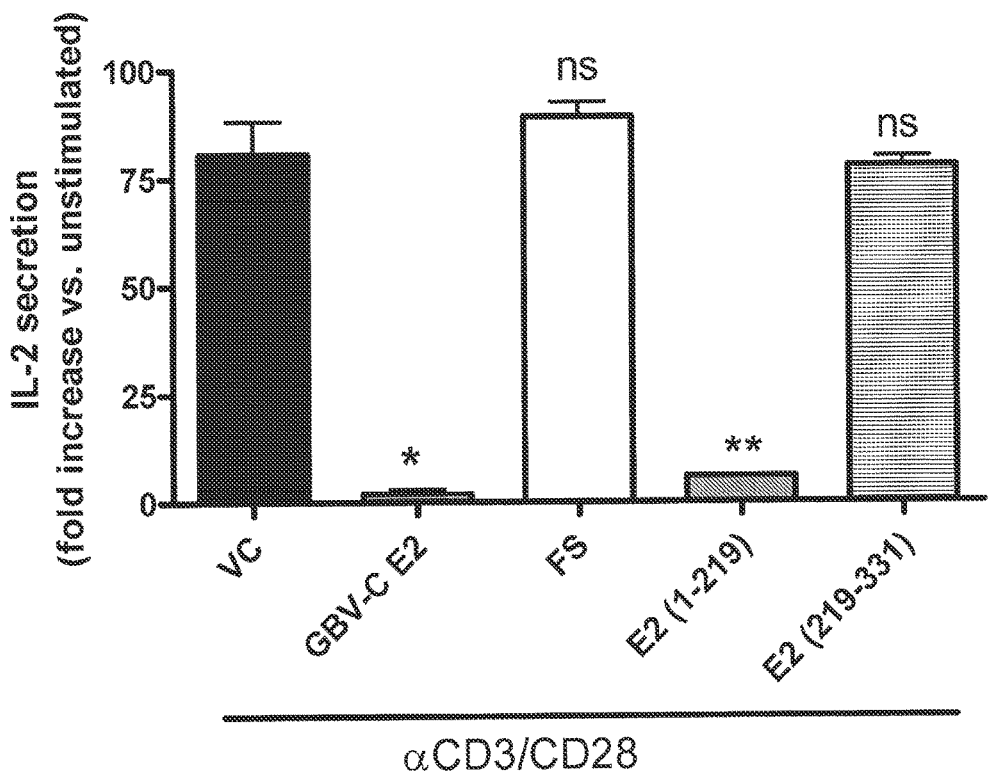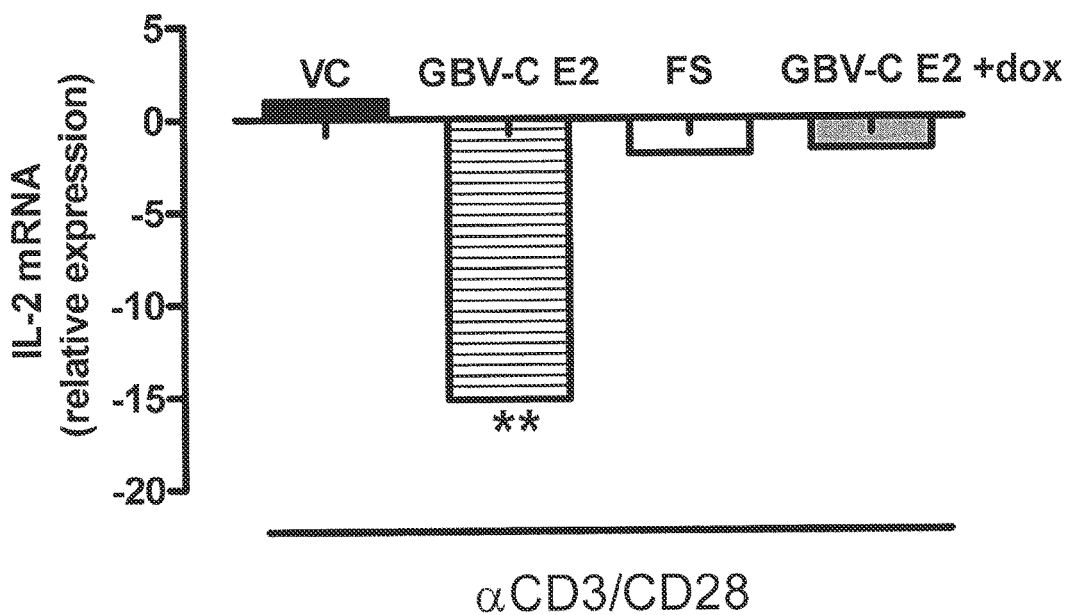
FIG. 2A-B

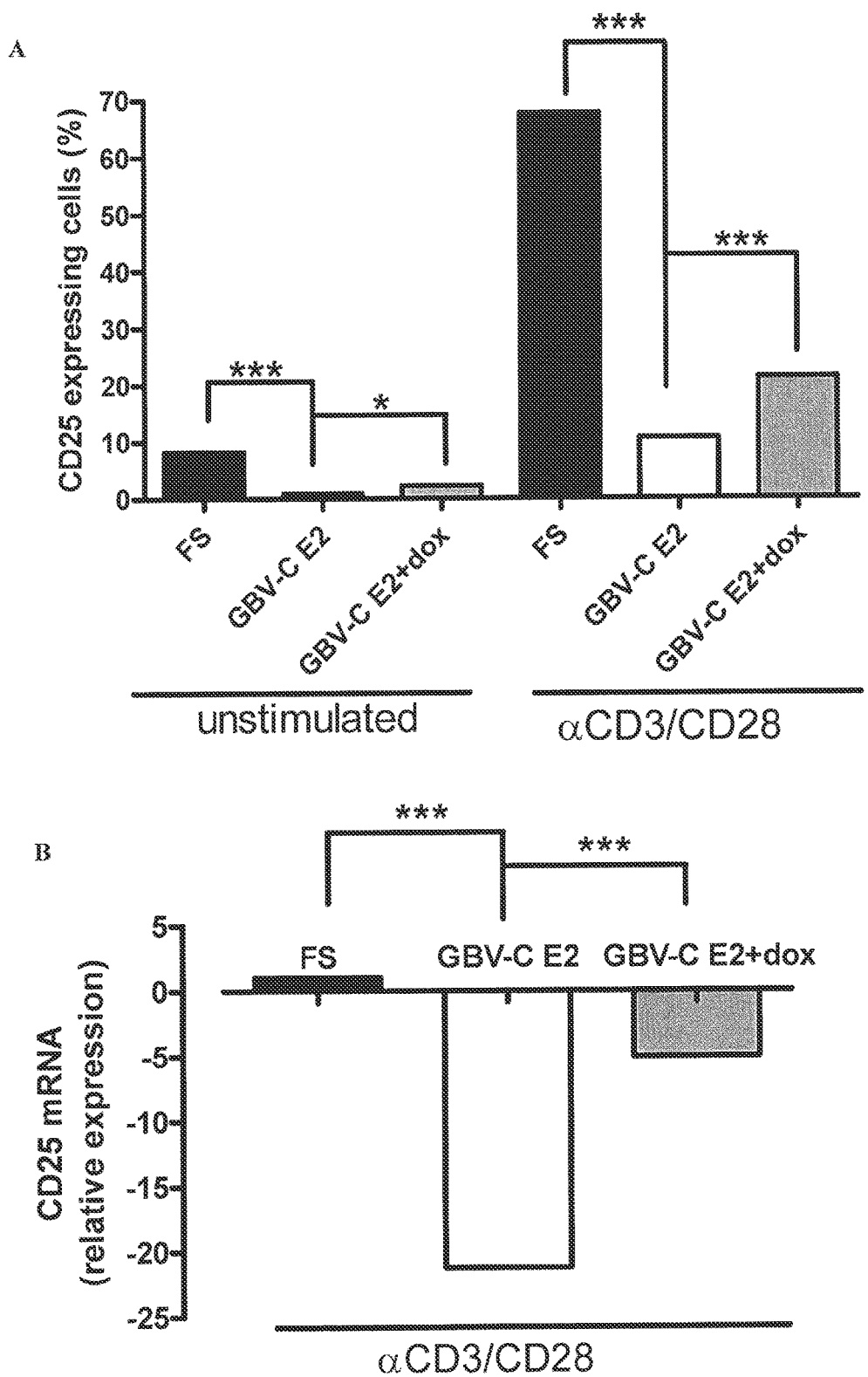
FIG. 3A-B

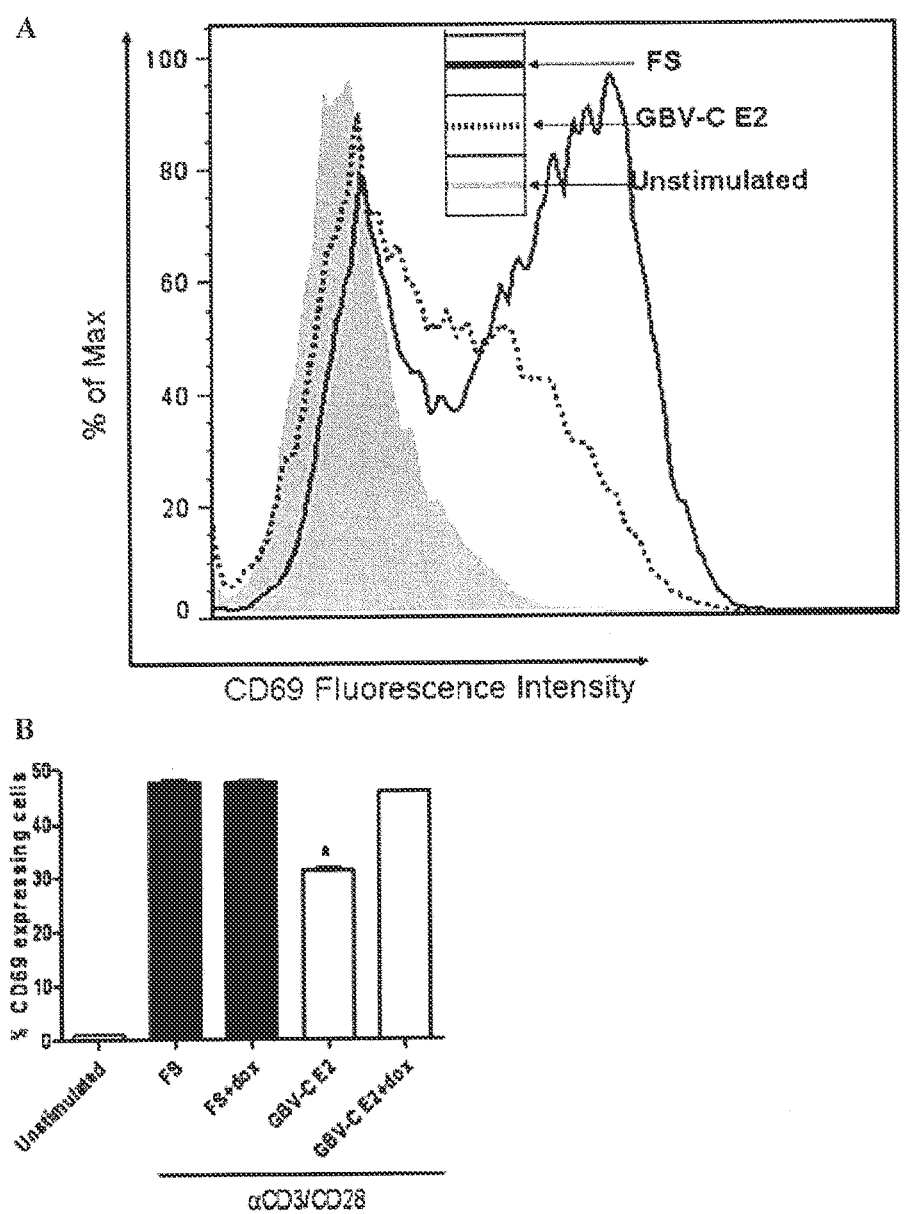
FIG. 6A-B

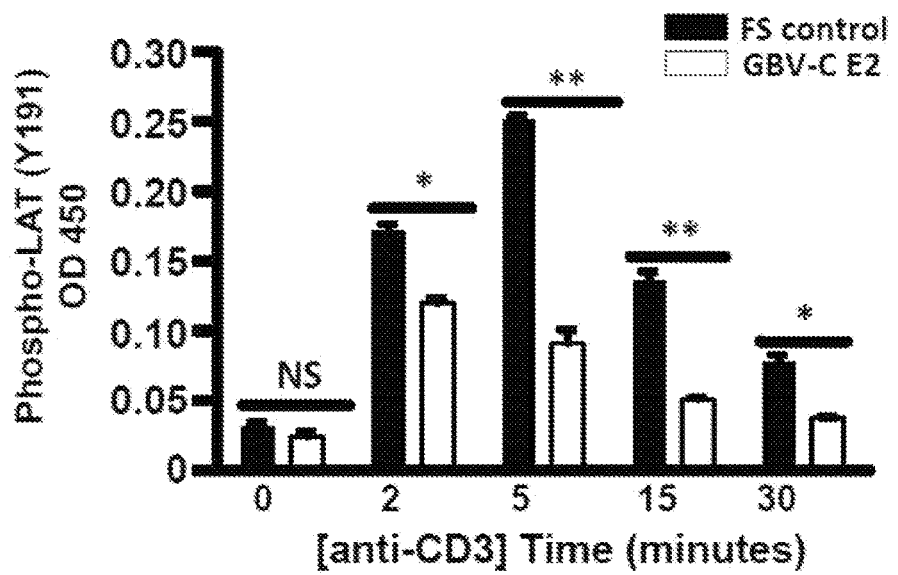
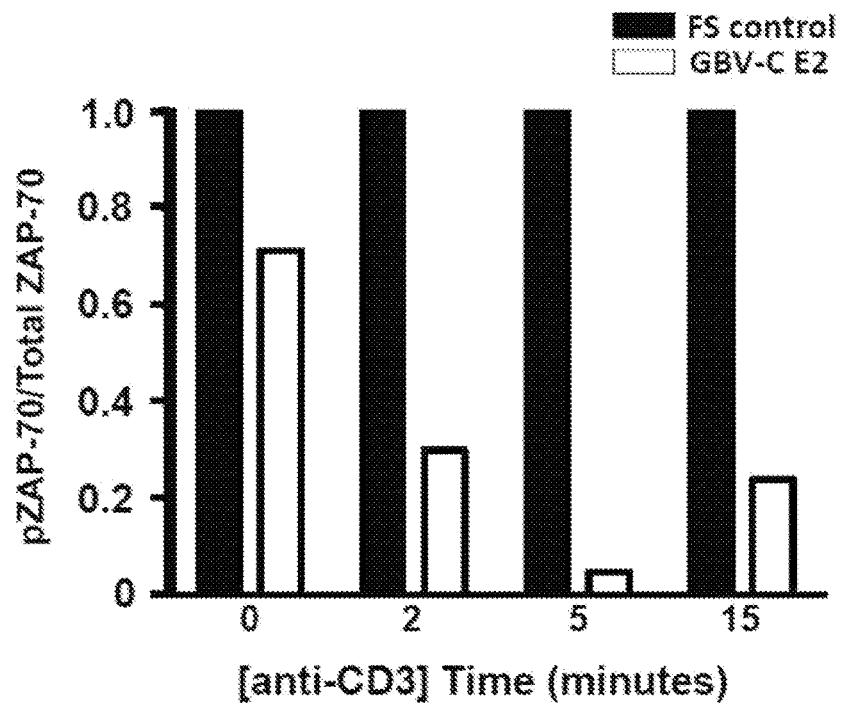
FIG. 19A-B

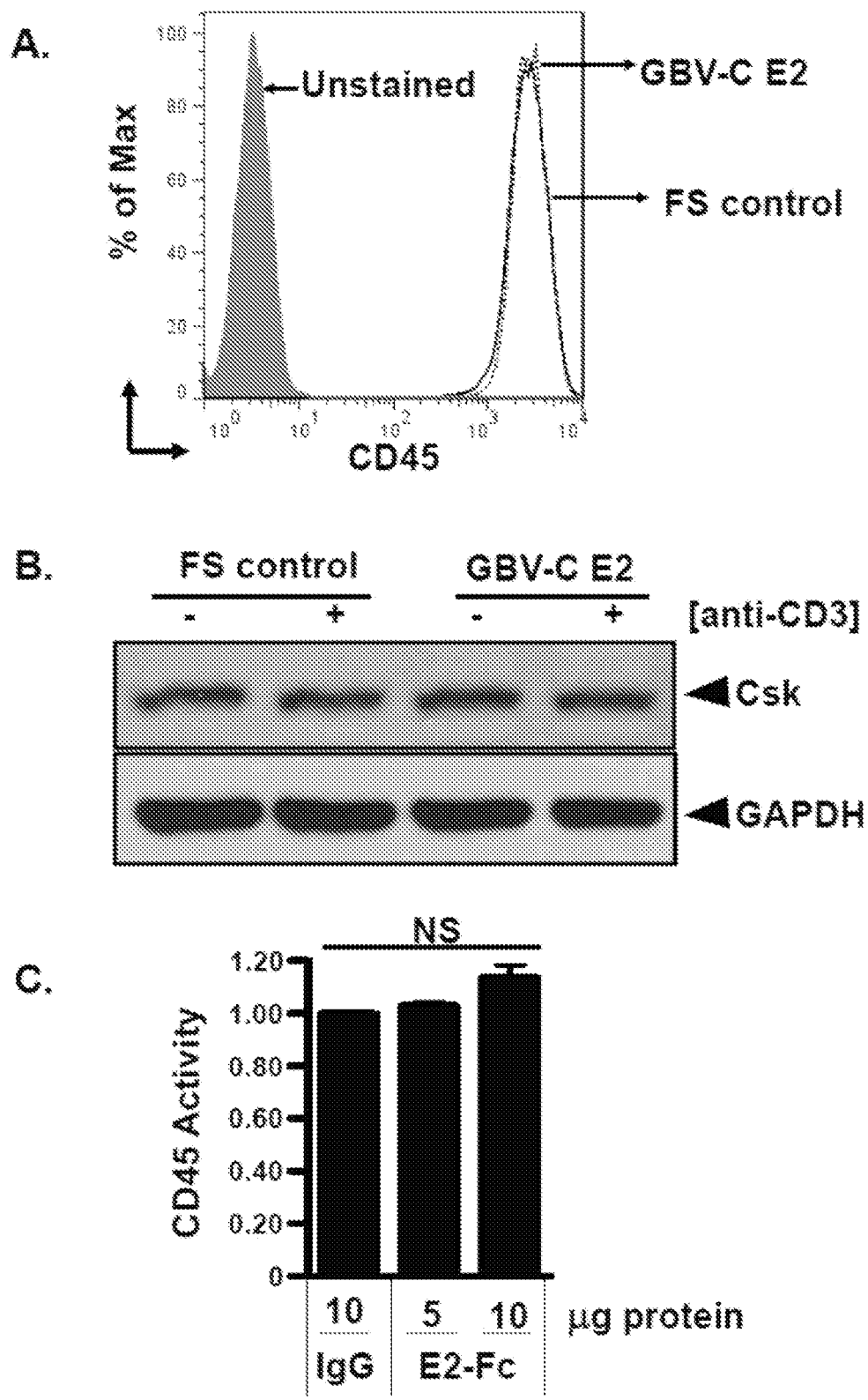
FIG. 20A-C

```
A. PQYVYGSVS  B. TGGFYEPLV  C. PNGP  D. PGTP  ⎫
   ---------     ----------     ----     --V-  ⎪
   ---------     ----------     ----     --V-  ⎪
   ---------     ----------     ----     --V-  ⎪
   ---------     ----------     ----     --V-  ⎪
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     --V-  ⎪
   ---------     ----------     ----     --V-  ⎪
   ------A--     ----------     ----     ----  ⎪
   ------A--     ----------     ----     ----  ⎪
   ---------     ----------     ----     --V-  ⎪
   ---------     ----------     ----     ----  ⎪
   ---------     ----------     ----     ----  ⎪
   ---------     ----------     ----     --V-  ⎪
   ---------     ----------     ----     ----  ⎪
   ---------     ----------     ----     ----  ⎬ GBV-C_hum
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     ----  ⎪
   ---------     ----------     ----     ----  ⎪
   -L-------     ----------     ----     ----  ⎪
   ---------     ----------     ----     ----  ⎪
   ---------     ----------     ----     --I-  ⎪
   ---------     ----------     ----     ----  ⎪
   ---------     ----------     ----     ----  ⎪
   ---------     ----------     ----     ----  ⎪
   ---------     ----------     ----     --V-  ⎪
   ---------     ----------     ----     --V-  ⎪
   ---------     ----------     ----     --V-  ⎭
   -R--H-HIT     --AF-----A     ----     --A-  ⎫
   -R--H-HIT     --AF------     ----     --A-  ⎬ GBV-C_cpz
   -R--H-HIT     --AF------     ----     --A-  ⎭
   aa 83-91      aa 281-289    aa 48-51  aa 257-260
```

FIG. 22A-D

A. No Peptide

B. TAT only — 86.0%

C. GBV-C E2 (Y87) — 88.7%

D. GBV-C E2 (Y87H) — 86.3%

FIG. 24A-D

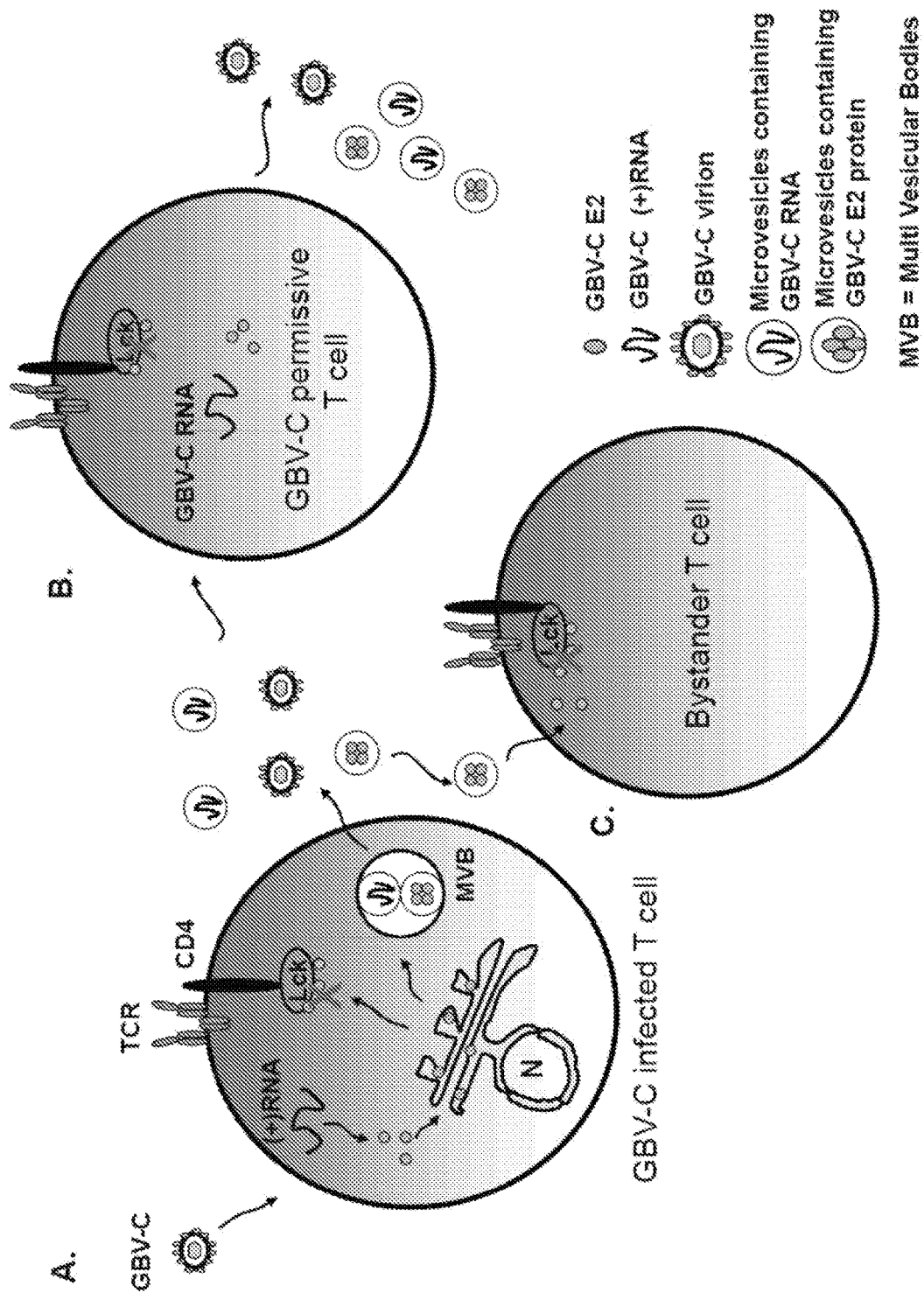
FIG. 25A-C

US 9,611,301 B2

SEQUENCE LISTING

```
<160> NUMBER OF SEQ ID NOS: 21

<210> SEQ ID NO 1
<211> LENGTH: 9395
<212> TYPE: DNA
<213> ORGANISM: Hepatitis GB Virus C
<220> FEATURE:
<221> NAME/KEY: CDS
<222> LOCATION: (555)..(9083)

<400> SEQUENCE: 1
tgacgtgggg gggttgatcc ccccccccg gcactgggtg caagcccat aaaccgacgc      60 ctatctaagt agacgcaatg actcggcgcc gactcggcga ccggccaaaa ggtggtggat    120
gggtggtgac agggttggta ggtcgtaaat cccggtcatc ctggtagcca ctataggtgg   180
gtcttaagag aaggtcaaga ctcctcttgt gcctgcggcg agaccgcgca cggtccacag   240
gtgctggccc taccggtgtg aataagggcc cgacgtcagg ctcgtcgtta aaccgagccc   300
```

```
gtcacccacc tgggcaaacg acgcccacgt acggtccacg tcgcccttca atgtctctct      360
tgaccaatag gtttatccgg cgagttgaca aggaccagtg ggggccgggg gttatgggga      420
aggaccccaa accctgccct tcccggtggg ccgggaaatg catggggcca cccagctccg      480
cggcggcctg cagccggggt agcccaagaa tccttcgggt gagggcgggt ggcatttctc      540
ttttctatac catc atg gca gtc ctt ctg ctc ctt ctc gtg gtt gag gcc         590
              Met Ala Val Leu Leu Leu Leu Val Val Glu Ala
              1               5                   10 ggg gcc att ctg gcc ccg gcc acc cac gct tgt cga gcg aat ggg caa         638
Gly Ala Ile Leu Ala Pro Ala Thr His Ala Cys Arg Ala Asn Gly Gln
            15                  20                  25 tat ttc ctc aca aat tgc tgt gcc ccg gaa gac atc ggg ttc tgc ctg         686
Tyr Phe Leu Thr Asn Cys Cys Ala Pro Glu Asp Ile Gly Phe Cys Leu
    30                  35                  40 gaa ggc gga tgc ctg gtg gcc ctg ggc tgc acg gtt tgc acc gac cgt         734
Glu Gly Gly Cys Leu Val Ala Leu Gly Cys Thr Val Cys Thr Asp Arg
45              50                  55                  60 tgc tgg cca ctg tat cag gcg ggt ttg gct gtg cgg cct ggc aag tcc         782
Cys Trp Pro Leu Tyr Gln Ala Gly Leu Ala Val Arg Pro Gly Lys Ser
                65                  70                  75 gcg gcc cag ctc gtt ggg gaa ctg ggg agc ctg tac ggg ccc ttg tcg         830
Ala Ala Gln Leu Val Gly Glu Leu Gly Ser Leu Tyr Gly Pro Leu Ser
            80                  85                  90 gtc tcg gct tac gta gcc ggg atc ctg ggt ctg ggc gag gtt tac tcc         878
Val Ser Ala Tyr Val Ala Gly Ile Leu Gly Leu Gly Glu Val Tyr Ser
        95                  100                 105 ggg gtc ctg aca gtt ggt gtt gcg ttg agg cgc cgg gtc tac ctg atg         926
Gly Val Leu Thr Val Gly Val Ala Leu Arg Arg Arg Val Tyr Leu Met
    110                 115                 120 ccc aac ctg aag tgt gca gta gaa tgt gac gtt aag tgg gga agt gag         974
Pro Asn Leu Lys Cys Ala Val Glu Cys Asp Val Lys Trp Gly Ser Glu
125                 130                 135                 140 ttt tgg aga tgg act gag cag ttg gcc tcc aat tac tgg att ttg gaa        1022
Phe Trp Arg Trp Thr Glu Gln Leu Ala Ser Asn Tyr Trp Ile Leu Glu
                145                 150                 155 tac ctt tgg aaa gtc cca ttt gaa ttt tgg aga gga gtg atg agc ctg        1070
Tyr Leu Trp Lys Val Pro Phe Glu Phe Trp Arg Gly Val Met Ser Leu
            160                 165                 170 acc cct ctg ttg gtt tgg gtg gcc gca ttg ctt ttg ctg gag caa cgg        1118
Thr Pro Leu Leu Val Trp Val Ala Ala Leu Leu Leu Glu Gln Arg
        175                 180                 185 att gtc atg gtt ttc ctg ctg gtg acg atg gcg ggg atg ttg caa ggc        1166
Ile Val Met Val Phe Leu Leu Val Thr Met Ala Gly Met Leu Gln Gly
    190                 195                 200 gcc ccc gcc tcc gtt ttg ggg tcc cgc ccc ttt gac tac ggg ttg aag        1214
Ala Pro Ala Ser Val Leu Gly Ser Arg Pro Phe Asp Tyr Gly Leu Lys
205                 210                 215                 220 tgg cag tca tgc tcc tgc agg gct aac ggg tcg cgt att ccc act ggg        1262
Trp Gln Ser Cys Ser Cys Arg Ala Asn Gly Ser Arg Ile Pro Thr Gly
                225                 230                 235 gag agg gtg tgg gat cga ggg aat gtc acg ctc ttg tgt gac tgc ccc        1310
Glu Arg Val Trp Asp Arg Gly Asn Val Thr Leu Leu Cys Asp Cys Pro
            240                 245                 250 aac ggc ccc tgg gtt tgg gtc ccg gcc ttt tgc cag gcg gtt ggg tgg        1358
Asn Gly Pro Trp Val Trp Val Pro Ala Phe Cys Gln Ala Val Gly Trp
        255                 260                 265 ggc gac ccc atc acc cat tgg agc cac gga caa aac cag tgg ccc cta        1406
Gly Asp Pro Ile Thr His Trp Ser His Gly Gln Asn Gln Trp Pro Leu
    270                 275                 280
```

| | | | | | | | | | | | | | | |
|---|---|---|---|---|---|---|---|---|---|---|---|---|---|---|
| tca | tgc | ccc | caa | tat | gtc | tat | ggg | tct | gtg | tcc | gta | acg | tgc | gtg | tgg | 1454 |
| Ser | Cys | Pro | Gln | Tyr | Val | Tyr | Gly | Ser | Val | Ser | Val | Thr | Cys | Val | Trp | |
| 285 | | | | 290 | | | | | 295 | | | | | 300 | | | ggt tcc gtg tct tgg ttt gcc tcg acc ggc ggt cgt gat tcg aag atc 1502
Gly Ser Val Ser Trp Phe Ala Ser Thr Gly Gly Arg Asp Ser Lys Ile
                305                 310                 315 gat gtg tgg agt ttg gtg ccg gtt gga tct gcc agc tgc acc ata gcc 1550
Asp Val Trp Ser Leu Val Pro Val Gly Ser Ala Ser Cys Thr Ile Ala
        320                 325                 330 gct cta ggg tca tcg gat cgc gac acg gtt gag ctc tcc gag tgg 1598
Ala Leu Gly Ser Ser Asp Arg Asp Thr Val Val Glu Leu Ser Glu Trp
    335                 340                 345 gga gtc ccg tgc gta acg tgt att ctg gac cgt cgg cct gct tca tgt 1646
Gly Val Pro Cys Val Thr Cys Ile Leu Asp Arg Arg Pro Ala Ser Cys
        350                 355                 360 ggc acc tgt gtg cgg gac tgc tgg ccc gaa acc ggg tcg gtt aga ttc 1694
Gly Thr Cys Val Arg Asp Cys Trp Pro Glu Thr Gly Ser Val Arg Phe
365                 370                 375                 380 cct ttc cat cgg tgc ggc acg ggg cct cgg ctg aca aag gac ttg gaa 1742
Pro Phe His Arg Cys Gly Thr Gly Pro Arg Leu Thr Lys Asp Leu Glu
            385                 390                 395 gct gtg ccc ttc gtc aac agg aca act ccc ttc acc ata agg ggc ccc 1790
Ala Val Pro Phe Val Asn Arg Thr Thr Pro Phe Thr Ile Arg Gly Pro
        400                 405                 410 ctg ggc aac cag ggg aga ggc aac ccg gtg cgg tcg ccc ctg ggt ttt 1838
Leu Gly Asn Gln Gly Arg Gly Asn Pro Val Arg Ser Pro Leu Gly Phe
    415                 420                 425 ggg tcc tac acc atg acc aag atc cgg gat tcc ctg cat ttg gtg aaa 1886
Gly Ser Tyr Thr Met Thr Lys Ile Arg Asp Ser Leu His Leu Val Lys
430                 435                 440 tgt ccc aca cca gcc ata gag cct ccg act gga acg ttc ggg ttc ttc 1934
Cys Pro Thr Pro Ala Ile Glu Pro Pro Thr Gly Thr Phe Gly Phe Phe
445                 450                 455                 460 ccc gga gtc ccg ccc att aac aac tgc atg ccg cta ggc acg gaa gtg 1982
Pro Gly Val Pro Pro Ile Asn Asn Cys Met Pro Leu Gly Thr Glu Val
            465                 470                 475 tct gag gca ttg ggc gga gct ggg ctt acg ggg ggg ttc tac gag cct 2030
Ser Glu Ala Leu Gly Gly Ala Gly Leu Thr Gly Gly Phe Tyr Glu Pro
        480                 485                 490 ctg gtt cgc agg tgt tcg gag ctg atg gga cgc cga aat ccg gtt tgc 2078
Leu Val Arg Arg Cys Ser Glu Leu Met Gly Arg Arg Asn Pro Val Cys
    495                 500                 505 ccg ggg tac gca tgg ctg tcc tct ggt aga cct gac ggg ttc ata cac 2126
Pro Gly Tyr Ala Trp Leu Ser Ser Gly Arg Pro Asp Gly Phe Ile His
510                 515                 520 gtc cag ggg cac ctg cag gag gtg gat gcg ggc aac ttc atc cct cct 2174
Val Gln Gly His Leu Gln Glu Val Asp Ala Gly Asn Phe Ile Pro Pro
525                 530                 535                 540 cca cgc tgg ttg ctc ttg gat ttt gta ttt gtc ctg ctc tat ctg atg 2222
Pro Arg Trp Leu Leu Leu Asp Phe Val Phe Val Leu Leu Tyr Leu Met
            545                 550                 555 aag ctg gct gag gca cgg ttg gtc ccg ttg atc ttg ctt ctg ctg tgg 2270
Lys Leu Ala Glu Ala Arg Leu Val Pro Leu Ile Leu Leu Leu Leu Trp
        560                 565                 570 tgg tgg gtg aac cag ttg gcg gtt cta gga ctg ccg gct gtg gac gct 2318
Trp Trp Val Asn Gln Leu Ala Val Leu Gly Leu Pro Ala Val Asp Ala
    575                 580                 585 gcc gtg gcg ggt gaa gtt ttt gcg ggc cct gcc ttg tca tgg tgt ttg 2366
Ala Val Ala Gly Glu Val Phe Ala Gly Pro Ala Leu Ser Trp Cys Leu -continued

```
              590                 595                 600
ggc ctt ccc act gtc agt atg ata cta ggt cta gca aac ctg gtg ttg    2414
Gly Leu Pro Thr Val Ser Met Ile Leu Gly Leu Ala Asn Leu Val Leu
605                 610                 615                 620 tac ttt cgg tgg atg ggc cct cag cgc ctc atg ttc ctc gtg ttg tgg    2462
Tyr Phe Arg Trp Met Gly Pro Gln Arg Leu Met Phe Leu Val Leu Trp
                625                 630                 635 aag ctc gct cgg gga gct ttc ccg ctg gca ctt ttg atg ggg att tcg    2510
Lys Leu Ala Arg Gly Ala Phe Pro Leu Ala Leu Leu Met Gly Ile Ser
            640                 645                 650 gcg acc cgc ggg cgc acc tct gtg ctc ggg gcc gag ttc tgc ttc gat    2558
Ala Thr Arg Gly Arg Thr Ser Val Leu Gly Ala Glu Phe Cys Phe Asp
        655                 660                 665 gtc aca ttc gag gtg gac act tcg gtg ttg ggc tgg gtg gtg gcc agc    2606
Val Thr Phe Glu Val Asp Thr Ser Val Leu Gly Trp Val Val Ala Ser
    670                 675                 680 gtg gtg gct tgg gcc ata gcg ctc ctg agc tca atg agc gca ggg ggg    2654
Val Val Ala Trp Ala Ile Ala Leu Leu Ser Ser Met Ser Ala Gly Gly
685                 690                 695                 700 tgg aag cac aag gcc gtg atc tat agg acg tgg tgt aaa ggg tac cag    2702
Trp Lys His Lys Ala Val Ile Tyr Arg Thr Trp Cys Lys Gly Tyr Gln
                705                 710                 715 gct gtg cgc cag agg gtg gtg cgg agc ccc ctc ggg gag ggg cgt cct    2750
Ala Val Arg Gln Arg Val Val Arg Ser Pro Leu Gly Glu Gly Arg Pro
            720                 725                 730 acc aag ctt ctg acg ttc gcc tgg tgc ttg gcc tca tac atc tgg ccg    2798
Thr Lys Leu Leu Thr Phe Ala Trp Cys Leu Ala Ser Tyr Ile Trp Pro
        735                 740                 745 gat gct gtg atg atg gtg gtg gtg gcc ttg gtc ctc ctc ttc ggc ctg    2846
Asp Ala Val Met Met Val Val Val Ala Leu Val Leu Leu Phe Gly Leu
    750                 755                 760 ttc gac gca ctg gac tgg gcc ctg gag gag ctc ctg gtc tcc cgg ccc    2894
Phe Asp Ala Leu Asp Trp Ala Leu Glu Glu Leu Leu Val Ser Arg Pro
765                 770                 775                 780 tcg tta cgg cga ctg gca cgg gtg gtt gag tgc tgt gtg atg gcg ggc    2942
Ser Leu Arg Arg Leu Ala Arg Val Val Glu Cys Cys Val Met Ala Gly
                785                 790                 795 gag aag gcc acc acc atc cga ctg gtc tcc aag atg tgc gca aga ggg    2990
Glu Lys Ala Thr Thr Ile Arg Leu Val Ser Lys Met Cys Ala Arg Gly
            800                 805                 810 gcc tac ctg ttt gac cac atg ggc tct ttc tcg cgc gct gtc aag gag    3038
Ala Tyr Leu Phe Asp His Met Gly Ser Phe Ser Arg Ala Val Lys Glu
        815                 820                 825 cgc ttg ttg gaa tgg gac gcg gct ttg gag ccc ttg tca ttc act agg    3086
Arg Leu Leu Glu Trp Asp Ala Ala Leu Glu Pro Leu Ser Phe Thr Arg
    830                 835                 840 acg gac tgt cgc atc atc aga gat gcc gcg agg acc ctg tcc tgc gga    3134
Thr Asp Cys Arg Ile Ile Arg Asp Ala Ala Arg Thr Leu Ser Cys Gly
845                 850                 855                 860 cag tgc gtc atg ggt tta ccc gtg gta gca cgg cgc ggt gat gag gtt    3182
Gln Cys Val Met Gly Leu Pro Val Val Ala Arg Arg Gly Asp Glu Val
                865                 870                 875 ctc atc ggc gtc ttt cag gat gtg aat cat ttg cct ccc ggg ttt gtc    3230
Leu Ile Gly Val Phe Gln Asp Val Asn His Leu Pro Pro Gly Phe Val
            880                 885                 890 ccg act gca cca gtt gtc atc cgt cgg tgc gga aag ggc ttc ctg ggg    3278
Pro Thr Ala Pro Val Val Ile Arg Arg Cys Gly Lys Gly Phe Leu Gly
        895                 900                 905 gtc acg aag gca gcc ttg aca ggt agg gat cct gac tta cat cca ggg    3326
```

|  |  |
|---|---|
| Val Thr Lys Ala Ala Leu Thr Gly Arg Asp Pro Asp Leu His Pro Gly<br>          910                    915                    920 |  |
| aac gtc atg gtg ttg ggg acg gct acg tca cga agc atg ggc aca tgt<br>Asn Val Met Val Leu Gly Thr Ala Thr Ser Arg Ser Met Gly Thr Cys<br>925                    930                    935                    940 | 3374 |
| ctg aat ggc ctg ctg ttc aca act ttc cat ggg gct tca tcc cga acc<br>Leu Asn Gly Leu Leu Phe Thr Thr Phe His Gly Ala Ser Ser Arg Thr<br>                    945                    950                    955 | 3422 |
| atc gcc acg ccc gtg ggg gcc ctt aat ccc agg tgg tgg tca gcc agt<br>Ile Ala Thr Pro Val Gly Ala Leu Asn Pro Arg Trp Trp Ser Ala Ser<br>            960                    965                    970 | 3470 |
| gat gac gtc acg gtg tac ccg ctt cca gat ggg gca act tcg ttg acg<br>Asp Asp Val Thr Val Tyr Pro Leu Pro Asp Gly Ala Thr Ser Leu Thr<br>                  975                    980                    985 | 3518 |
| ccc tgc act tgc cag gcg gag tcc tgt tgg gtt att aga tcc gac ggg<br>Pro Cys Thr Cys Gln Ala Glu Ser Cys Trp Val Ile Arg Ser Asp Gly<br>          990                    995                   1000 | 3566 |
| gct ttg tgc cat ggc ttg agc aag ggg gac aag gtt gag ctg gat<br>Ala Leu Cys His Gly Leu Ser Lys Gly Asp Lys Val Glu Leu Asp<br>1005                  1010                     1015 | 3611 |
| gtg gcc atg gag gtc tct gac ttc cgt ggt tcg tct ggt tca ccg<br>Val Ala Met Glu Val Ser Asp Phe Arg Gly Ser Ser Gly Ser Pro<br>1020                  1025                     1030 | 3656 |
| gtc ctt tgc gac aaa ggg cac gca gta aga atg ctc gtg tca gtg<br>Val Leu Cys Asp Lys Gly His Ala Val Arg Met Leu Val Ser Val<br>1035                  1040                     1045 | 3701 |
| ctc cac tct ggc ggc agg gtt act gcg gcg cga ttc act agg ccg<br>Leu His Ser Gly Gly Arg Val Thr Ala Ala Arg Phe Thr Arg Pro<br>1050                  1055                     1060 | 3746 |
| tgg act caa gta cca aca gat gcc aag act acc aca gaa ccc cct<br>Trp Thr Gln Val Pro Thr Asp Ala Lys Thr Thr Thr Glu Pro Pro<br>1065                  1070                     1075 | 3791 |
| ccg gtg ccg gca aaa gga gtt ttc aag gag gcc ccg ttg ttt atg<br>Pro Val Pro Ala Lys Gly Val Phe Lys Glu Ala Pro Leu Phe Met<br>1080                  1085                     1090 | 3836 |
| cct acg ggg gcg gga aag agc acc cgt gta ccg ttg gag tac ggc<br>Pro Thr Gly Ala Gly Lys Ser Thr Arg Val Pro Leu Glu Tyr Gly<br>1095                  1100                     1105 | 3881 |
| aac atg ggc cac aag gtc ttg atc ttg aac ccg tcg gta gct acc<br>Asn Met Gly His Lys Val Leu Ile Leu Asn Pro Ser Val Ala Thr<br>1110                  1115                     1120 | 3926 |
| gtg agg gcc atg ggc cca tac atg gag cgg ctg gcg ggg aaa cac<br>Val Arg Ala Met Gly Pro Tyr Met Glu Arg Leu Ala Gly Lys His<br>1125                  1130                     1135 | 3971 |
| ccc agt att tac tgt ggc cat gac acc act gct ttc aca agg atc<br>Pro Ser Ile Tyr Cys Gly His Asp Thr Thr Ala Phe Thr Arg Ile<br>1140                  1145                     1150 | 4016 |
| act gac tcg ccc ctt acg tat tcc act tac gga agg ttt ttg gcc<br>Thr Asp Ser Pro Leu Thr Tyr Ser Thr Tyr Gly Arg Phe Leu Ala<br>1155                  1160                     1165 | 4061 |
| aac cct agg cag atg ctg agg ggt gtg tcg gtg gtc att tgt gac<br>Asn Pro Arg Gln Met Leu Arg Gly Val Ser Val Val Ile Cys Asp<br>1170                  1175                     1180 | 4106 |
| gag tgc cac agt cat gac tca act gtg ttg ttg ggc att ggg cgt<br>Glu Cys His Ser His Asp Ser Thr Val Leu Leu Gly Ile Gly Arg<br>1185                  1190                     1195 | 4151 |
| gtc agg gag ctg gcg cga gga tgt gga gtg caa ttg gtg ctc tac<br>Val Arg Glu Leu Ala Arg Gly Cys Gly Val Gln Leu Val Leu Tyr<br>1200                  1205                     1210 | 4196 |

```
gcc  act  gcc  acc  cct  ccc  gga  tcc  ccg  atg  acc  cag  cac  cca  tca        4241
Ala  Thr  Ala  Thr  Pro  Pro  Gly  Ser  Pro  Met  Thr  Gln  His  Pro  Ser
1215                 1220                      1225 atc  att  gag  aca  aaa  ctg  gac  gtg  gga  gag  atc  ccc  ttc  tat  ggg        4286
Ile  Ile  Glu  Thr  Lys  Leu  Asp  Val  Gly  Glu  Ile  Pro  Phe  Tyr  Gly
1230                 1235                      1240 cat  ggc  ata  cct  ctt  gag  cgg  atg  cgg  acc  gga  agg  cat  ctc  gta        4331
His  Gly  Ile  Pro  Leu  Glu  Arg  Met  Arg  Thr  Gly  Arg  His  Leu  Val
1245                 1250                      1255 ttc  tgc  cac  tcc  aag  gct  gag  tgc  gag  cgc  ctg  gcg  ggc  cag  ttt        4376
Phe  Cys  His  Ser  Lys  Ala  Glu  Cys  Glu  Arg  Leu  Ala  Gly  Gln  Phe
1260                 1265                      1270 tcg  gct  agg  ggg  gta  aat  gcc  atc  gcc  tat  tac  agg  ggg  aaa  gac        4421
Ser  Ala  Arg  Gly  Val  Asn  Ala  Ile  Ala  Tyr  Tyr  Arg  Gly  Lys  Asp
1275                 1280                      1285 agt  tct  atc  atc  aaa  gat  gga  gac  ctg  gtg  gtg  tgt  gct  aca  gac        4466
Ser  Ser  Ile  Ile  Lys  Asp  Gly  Asp  Leu  Val  Val  Cys  Ala  Thr  Asp
1290                 1295                      1300 gca  cta  tcc  act  ggg  tac  act  ggg  aac  ttc  gat  tct  gtc  acc  gat        4511
Ala  Leu  Ser  Thr  Gly  Tyr  Thr  Gly  Asn  Phe  Asp  Ser  Val  Thr  Asp
1305                 1310                      1315 tgt  ggg  tta  gtg  gtg  gag  gag  gtc  gtc  gag  gtg  acc  ctt  gat  ccc        4556
Cys  Gly  Leu  Val  Val  Glu  Glu  Val  Val  Glu  Val  Thr  Leu  Asp  Pro
1320                 1325                      1330 acc  att  acc  atc  tcc  ctg  cgc  acg  gtg  ccc  gcg  tcg  gct  gaa  ctg        4601
Thr  Ile  Thr  Ile  Ser  Leu  Arg  Thr  Val  Pro  Ala  Ser  Ala  Glu  Leu
1335                 1340                      1345 tcg  atg  cag  cgg  cga  gga  cgc  acg  ggt  agg  ggc  agg  tct  ggg  cgc        4646
Ser  Met  Gln  Arg  Arg  Gly  Arg  Thr  Gly  Arg  Gly  Arg  Ser  Gly  Arg
1350                 1355                      1360 tac  tac  tac  gcg  ggg  gtc  ggc  aag  gcc  cct  gct  ggt  gtg  gtg  cgc        4691
Tyr  Tyr  Tyr  Ala  Gly  Val  Gly  Lys  Ala  Pro  Ala  Gly  Val  Val  Arg
1365                 1370                      1375 tca  ggt  cct  gtc  tgg  tcg  gcg  gtg  gaa  gcc  ggt  gtg  acc  tgg  tac        4736
Ser  Gly  Pro  Val  Trp  Ser  Ala  Val  Glu  Ala  Gly  Val  Thr  Trp  Tyr
1380                 1385                      1390 gga  atg  gaa  cct  gac  ctg  aca  gca  aac  cta  ctg  aga  ctt  tac  gac        4781
Gly  Met  Glu  Pro  Asp  Leu  Thr  Ala  Asn  Leu  Leu  Arg  Leu  Tyr  Asp
1395                 1400                      1405 aac  tgc  cct  tac  acc  gca  gcc  gtc  gca  gct  gac  att  ggg  gaa  gcc        4826
Asn  Cys  Pro  Tyr  Thr  Ala  Ala  Val  Ala  Ala  Asp  Ile  Gly  Glu  Ala
1410                 1415                      1420 gcg  gtg  ttc  ttt  tcg  ggg  ctt  gcc  ccg  ttg  agg  atg  cat  ccc  gat        4871
Ala  Val  Phe  Phe  Ser  Gly  Leu  Ala  Pro  Leu  Arg  Met  His  Pro  Asp
1425                 1430                      1435 gtt  agc  tgg  gca  aaa  gtt  cgc  ggc  gtc  aac  tgg  ccc  ttc  ctg  gtg        4916
Val  Ser  Trp  Ala  Lys  Val  Arg  Gly  Val  Asn  Trp  Pro  Phe  Leu  Val
1440                 1445                      1450 ggt  gtt  cag  cgg  acc  atg  tgc  cgg  gaa  aca  ctg  tct  ccc  ggc  cca        4961
Gly  Val  Gln  Arg  Thr  Met  Cys  Arg  Glu  Thr  Leu  Ser  Pro  Gly  Pro
1455                 1460                      1465 tcg  gat  gac  ccc  cag  tgg  gca  ggt  ctg  aag  ggc  ccg  aat  cct  gtc        5006
Ser  Asp  Asp  Pro  Gln  Trp  Ala  Gly  Leu  Lys  Gly  Pro  Asn  Pro  Val
1470                 1475                      1480 cca  ctc  ctg  ctg  agg  tgg  ggc  aat  gat  tta  cca  tct  aaa  gtg  gcc        5051
Pro  Leu  Leu  Leu  Arg  Trp  Gly  Asn  Asp  Leu  Pro  Ser  Lys  Val  Ala
1485                 1490                      1495 ggc  cat  cac  atc  gtg  gac  gac  ctg  gtc  cgt  agg  ctc  ggg  gtg  gcg        5096
Gly  His  His  Ile  Val  Asp  Asp  Leu  Val  Arg  Arg  Leu  Gly  Val  Ala
1500                 1505                      1510
```

-continued

| | |
|---|---|
| gag ggt tac gtc cgc tgc gat gcg gga ccc atc ttg atg gtg ggc<br>Glu Gly Tyr Val Arg Cys Asp Ala Gly Pro Ile Leu Met Val Gly<br>1515                      1520                        1525 | 5141 |
| ctc gct att gcg ggg ggc atg atc tat gcg tca tac acc ggg tct<br>Leu Ala Ile Ala Gly Gly Met Ile Tyr Ala Ser Tyr Thr Gly Ser<br>1530                      1535                        1540 | 5186 |
| ctc gtg gtg gtt aca gac tgg gat gtg aag ggg ggt ggc agc ccc<br>Leu Val Val Val Thr Asp Trp Asp Val Lys Gly Gly Gly Ser Pro<br>1545                      1550                        1555 | 5231 |
| ctt tat cgg cat gga gac cag gcc acg ccc cag ccg gtt gtg cag<br>Leu Tyr Arg His Gly Asp Gln Ala Thr Pro Gln Pro Val Val Gln<br>1560                      1565                        1570 | 5276 |
| gtc ccc ccg gta gac cat cgg ccg ggg gga gag tct gcg cca tcg<br>Val Pro Pro Val Asp His Arg Pro Gly Gly Glu Ser Ala Pro Ser<br>1575                      1580                        1585 | 5321 |
| gat gcc aac aca gtg aca gat gcg gtg gcg gcc atc cag gtg gat<br>Asp Ala Asn Thr Val Thr Asp Ala Val Ala Ala Ile Gln Val Asp<br>1590                      1595                        1600 | 5366 |
| tgc gat tgg tca gtc atg acc ctg tcg atc ggg gaa gtg ctg tcc<br>Cys Asp Trp Ser Val Met Thr Leu Ser Ile Gly Glu Val Leu Ser<br>1605                      1610                        1615 | 5411 |
| ttg gcc cag gct aag acg gcc gag gcc tac gca gct acc acc aag<br>Leu Ala Gln Ala Lys Thr Ala Glu Ala Tyr Ala Ala Thr Thr Lys<br>1620                      1625                        1630 | 5456 |
| tgg ctt gct ggc tgc tac acg ggg acg cgg gcc gtc ccc act gtt<br>Trp Leu Ala Gly Cys Tyr Thr Gly Thr Arg Ala Val Pro Thr Val<br>1635                      1640                        1645 | 5501 |
| tca att gtt gac aag ctc ttc gcc ggg ggc tgg gcg gcg gtg gta<br>Ser Ile Val Asp Lys Leu Phe Ala Gly Gly Trp Ala Ala Val Val<br>1650                      1655                        1660 | 5546 |
| ggc cat tgc cac agt gta ata gct gcg gca gtg gcg gcc tat ggg<br>Gly His Cys His Ser Val Ile Ala Ala Ala Val Ala Ala Tyr Gly<br>1665                      1670                        1675 | 5591 |
| gct tct agg agc cct cca ttg gct gct gcc gct tcc tac ctc atg<br>Ala Ser Arg Ser Pro Pro Leu Ala Ala Ala Ala Ser Tyr Leu Met<br>1680                      1685                        1690 | 5636 |
| ggg ttg ggc gtc gga ggc aac gcg caa acc cgc tta gcc tcc gct<br>Gly Leu Gly Val Gly Gly Asn Ala Gln Thr Arg Leu Ala Ser Ala<br>1695                      1700                        1705 | 5681 |
| ctc cta cta ggg gcc gct ggg acc gct ctg ggc acg cct gtc gtg<br>Leu Leu Leu Gly Ala Ala Gly Thr Ala Leu Gly Thr Pro Val Val<br>1710                      1715                        1720 | 5726 |
| ggg tta acc atg gcg ggc gcg ttc atg gga agt gct agc gtc tcc<br>Gly Leu Thr Met Ala Gly Ala Phe Met Gly Ser Ala Ser Val Ser<br>1725                      1730                        1735 | 5771 |
| ccc tcc ttg gtc acc att tta ctg ggg gcc gtg ggg ggc tgg gag<br>Pro Ser Leu Val Thr Ile Leu Leu Gly Ala Val Gly Gly Trp Glu<br>1740                      1745                        1750 | 5816 |
| ggc gtg gtg aat gcg gct agc ctt gtc ttc gac ttt atg gcg ggg<br>Gly Val Val Asn Ala Ala Ser Leu Val Phe Asp Phe Met Ala Gly<br>1755                      1760                        1765 | 5861 |
| aaa cta tca tca gaa gat ctg tgg tat gcc atc cca gtg cta acc<br>Lys Leu Ser Ser Glu Asp Leu Trp Tyr Ala Ile Pro Val Leu Thr<br>1770                      1775                        1780 | 5906 |
| agt ccg ggg gca gga ctt gcg ggg atc gcc ctc ggg ttg gtg ttg<br>Ser Pro Gly Ala Gly Leu Ala Gly Ile Ala Leu Gly Leu Val Leu<br>1785                      1790                        1795 | 5951 |
| tac tca gct aac aac tct ggc act acc act tgg ttg aac cgt ctg<br>Tyr Ser Ala Asn Asn Ser Gly Thr Thr Thr Trp Leu Asn Arg Leu | 5996 |

```
                                                        -continued 1800                    1805                    1810 ctg act aca ttg cca agg tcc tca tgc atc cct gac agt tac ttt    6041
Leu Thr Thr Leu Pro Arg Ser Ser Cys Ile Pro Asp Ser Tyr Phe
1815                    1820                    1825 cag cag gcc gat tac tgt gac aag gtc tca gct gtg ctc cga cgc    6086
Gln Gln Ala Asp Tyr Cys Asp Lys Val Ser Ala Val Leu Arg Arg
1830                    1835                    1840 ttg agc ctc act cgc acc gtg gtt gcc ctg gtc aac agg gag cct    6131
Leu Ser Leu Thr Arg Thr Val Val Ala Leu Val Asn Arg Glu Pro
1845                    1850                    1855 aag gtg gat gag gtt cag gtg ggg tac gtc tgg gac ttg tgg gag    6176
Lys Val Asp Glu Val Gln Val Gly Tyr Val Trp Asp Leu Trp Glu
1860                    1865                    1870 tgg atc atg cgt caa gtg cgc atg gtg atg gcc aga ctt cgg gcc    6221
Trp Ile Met Arg Gln Val Arg Met Val Met Ala Arg Leu Arg Ala
1875                    1880                    1885 ctc tgc ccc gtg gtg tca tta ccc tta tgg cac tgc ggg gag ggg    6266
Leu Cys Pro Val Val Ser Leu Pro Leu Trp His Cys Gly Glu Gly
1890                    1895                    1900 tgg tcc gga gaa tgg ttg ttg gac ggc cat gtt gag agt cgt tgt    6311
Trp Ser Gly Glu Trp Leu Leu Asp Gly His Val Glu Ser Arg Cys
1905                    1910                    1915 ctt tgt ggt tgc gtg atc acc ggt gat gtt ttg aat ggg caa ctc    6356
Leu Cys Gly Cys Val Ile Thr Gly Asp Val Leu Asn Gly Gln Leu
1920                    1925                    1930 aaa gat cca gtt tac tct acc aag ctg tgc agg cat tat tgg atg    6401
Lys Asp Pro Val Tyr Ser Thr Lys Leu Cys Arg His Tyr Trp Met
1935                    1940                    1945 ggg aca gtc cct gtg aac atg ctg ggc tat ggc gag acg tcg cct    6446
Gly Thr Val Pro Val Asn Met Leu Gly Tyr Gly Glu Thr Ser Pro
1950                    1955                    1960 ttg ctc gcc tca gac acc ccg aag gtg gta cca ttc ggg acg tct    6491
Leu Leu Ala Ser Asp Thr Pro Lys Val Val Pro Phe Gly Thr Ser
1965                    1970                    1975 ggg tgg gct gag gtg gtg gtg acc cct acc cac gtt gtg atc agg    6536
Gly Trp Ala Glu Val Val Val Thr Pro Thr His Val Val Ile Arg
1980                    1985                    1990 cga aca tcc gcc tac aaa ctg ctg cgc cag caa atc ctg tcg gct    6581
Arg Thr Ser Ala Tyr Lys Leu Leu Arg Gln Gln Ile Leu Ser Ala
1995                    2000                    2005 gct gtt gct gag ccc tat tac gtc gac ggc ata ccg gtc tca tgg    6626
Ala Val Ala Glu Pro Tyr Tyr Val Asp Gly Ile Pro Val Ser Trp
2010                    2015                    2020 gac gcg gac gcg cga gcg cct gcc atg gtc tat ggc cct ggg caa    6671
Asp Ala Asp Ala Arg Ala Pro Ala Met Val Tyr Gly Pro Gly Gln
2025                    2030                    2035 agt gtc acc att gac ggg gaa cgc tac acc ctt ccg cat caa ctg    6716
Ser Val Thr Ile Asp Gly Glu Arg Tyr Thr Leu Pro His Gln Leu
2040                    2045                    2050 cgg ctt agg aat gtg gcg ccc tct gag gtg tca tcc gag gtg tcc    6761
Arg Leu Arg Asn Val Ala Pro Ser Glu Val Ser Ser Glu Val Ser
2055                    2060                    2065 att gac att ggg acg gag act gaa gac tca gaa ctg act gag gcc    6806
Ile Asp Ile Gly Thr Glu Thr Glu Asp Ser Glu Leu Thr Glu Ala
2070                    2075                    2080 gac ctg ccg ccg gcg gct gca gcc ctt cag gct atc gag aat gct    6851
Asp Leu Pro Pro Ala Ala Ala Ala Leu Gln Ala Ile Glu Asn Ala
2085                    2090                    2095 gcg aga att ctt gaa cct cac ata gat gtc atc atg gaa gat tgc    6896
```

```
Ala Arg Ile Leu Glu Pro His Ile Asp Val Ile Met Glu Asp Cys
2100                2105                2110 agt aca ccc tct ctt tgt ggg agt agc cga gag atg cct gtg tgg     6941
Ser Thr Pro Ser Leu Cys Gly Ser Ser Arg Glu Met Pro Val Trp
2115                2120                2125 gga gaa gac ata ccc cgc act cca tcg cca gca ctt atc tcg gtt     6986
Gly Glu Asp Ile Pro Arg Thr Pro Ser Pro Ala Leu Ile Ser Val
2130                2135                2140 act gag agc agc cca gat gag aag acc ccg tcg gtg tct tcc tcg     7031
Thr Glu Ser Ser Pro Asp Glu Lys Thr Pro Ser Val Ser Ser Ser
2145                2150                2155 cag gag gat acc ccg tct tct gac tca ttc gag gtc atc caa gag     7076
Gln Glu Asp Thr Pro Ser Ser Asp Ser Phe Glu Val Ile Gln Glu
2160                2165                2170 tcc gag aca gcc gaa ggg gag gaa agc gtc ttc aac gtg gct ctt     7121
Ser Glu Thr Ala Glu Gly Glu Glu Ser Val Phe Asn Val Ala Leu
2175                2180                2185 tcc gta cta aaa gcc ttg ttt cca cag agc gat gcc aca aga aag     7166
Ser Val Leu Lys Ala Leu Phe Pro Gln Ser Asp Ala Thr Arg Lys
2190                2195                2200 ctt acc gtt aag atg tca tgc tgt gtt gag aag agc gta aca cgc     7211
Leu Thr Val Lys Met Ser Cys Cys Val Glu Lys Ser Val Thr Arg
2205                2210                2215 ttc ttt tca ttg gga ttg acg gtc gct gac gtg gca agc ctg tgt     7256
Phe Phe Ser Leu Gly Leu Thr Val Ala Asp Val Ala Ser Leu Cys
2220                2225                2230 gag atg gaa atc cag aac cat aca gcc tat tgt gac aag gtg cgc     7301
Glu Met Glu Ile Gln Asn His Thr Ala Tyr Cys Asp Lys Val Arg
2235                2240                2245 act ccg ctt gaa ttg cag gtt ggg tgc ttg gtg ggc aat gaa ctt     7346
Thr Pro Leu Glu Leu Gln Val Gly Cys Leu Val Gly Asn Glu Leu
2250                2255                2260 acc ttt gaa tgt gac aag tgt gag gct agg caa gag acc ttg gct     7391
Thr Phe Glu Cys Asp Lys Cys Glu Ala Arg Gln Glu Thr Leu Ala
2265                2270                2275 tcc ttc tct tac att tgg tct ggg gtg cca ctg acg agg gcc act     7436
Ser Phe Ser Tyr Ile Trp Ser Gly Val Pro Leu Thr Arg Ala Thr
2280                2285                2290 ccg gcc aag ccc cct gtg gtg agg ccg gtt ggc tcc ttg ctg gtg     7481
Pro Ala Lys Pro Pro Val Val Arg Pro Val Gly Ser Leu Leu Val
2295                2300                2305 gcc gac acc acc aag gtg tat gtc acc aac ccg gac aat gtt ggg     7526
Ala Asp Thr Thr Lys Val Tyr Val Thr Asn Pro Asp Asn Val Gly
2310                2315                2320 aga aga gtt gac aag gtt acc ttc tgg cgt gcc cct agg gtt cat     7571
Arg Arg Val Asp Lys Val Thr Phe Trp Arg Ala Pro Arg Val His
2325                2330                2335 gac aaa ttc ctc gtg gac tcc ata gag cgc gct aag agg gca gct     7616
Asp Lys Phe Leu Val Asp Ser Ile Glu Arg Ala Lys Arg Ala Ala
2340                2345                2350 caa gcc tgc cta agc atg ggt tac act tat gag gag gca ata agg     7661
Gln Ala Cys Leu Ser Met Gly Tyr Thr Tyr Glu Glu Ala Ile Arg
2355                2360                2365 act gta agg cca cat gct gcc atg ggc tgg gga tct aag gtg tcg     7706
Thr Val Arg Pro His Ala Ala Met Gly Trp Gly Ser Lys Val Ser
2370                2375                2380 gtc aag gac ctc gcc acc cct gcg ggg aag atg gct gtc cat gac     7751
Val Lys Asp Leu Ala Thr Pro Ala Gly Lys Met Ala Val His Asp
2385                2390                2395
```

-continued

| | | | | | | | | | | | | | | |
|---|---|---|---|---|---|---|---|---|---|---|---|---|---|---|
| cgg | ctc | cag | gag | ata | ctt | gaa | ggg | acg | cca | gtc | ccc | ttt | act | ctt | 7796 |
| Arg | Leu | Gln | Glu | Ile | Leu | Glu | Gly | Thr | Pro | Val | Pro | Phe | Thr | Leu | |
| 2400 | | | | 2405 | | | | | 2410 | | | | | | | act gtg aaa aag gaa gtg ttc ttc aaa gac cga aag gaa gag aag    7841
Thr Val Lys Lys Glu Val Phe Phe Lys Asp Arg Lys Glu Glu Lys
2415            2420                2425 gcc ccc cgc ctc att gtg ttc ccc ccc ctg gac ttc cgg ata gct    7886
Ala Pro Arg Leu Ile Val Phe Pro Pro Leu Asp Phe Arg Ile Ala
2430            2435                2440 gaa aag ctt att ctg gga gac cct gga cgg gta gcc aag gcg gtg    7931
Glu Lys Leu Ile Leu Gly Asp Pro Gly Arg Val Ala Lys Ala Val
2445            2450                2455 ttg ggg ggg gcc tac gcc ttc cag tac acc cca aat cag cga att    7976
Leu Gly Gly Ala Tyr Ala Phe Gln Tyr Thr Pro Asn Gln Arg Ile
2460            2465                2470 agg gag atg ctc aaa ctg tgg gaa tca aag aag aca cca tgc gcc    8021
Arg Glu Met Leu Lys Leu Trp Glu Ser Lys Lys Thr Pro Cys Ala
2475            2480                2485 atc tgt gtg gac gcc aca tgc ttc gac agt agc ata act gaa gag    8066
Ile Cys Val Asp Ala Thr Cys Phe Asp Ser Ser Ile Thr Glu Glu
2490            2495                2500 gac gtg gcg ctg gag aca gag ctt tat gcc ctg gct tca gac cat    8111
Asp Val Ala Leu Glu Thr Glu Leu Tyr Ala Leu Ala Ser Asp His
2505            2510                2515 cca gaa tgg gtg cgt gcc ctg ggg aaa tac tat gcc tct ggc aca    8156
Pro Glu Trp Val Arg Ala Leu Gly Lys Tyr Tyr Ala Ser Gly Thr
2520            2525                2530 atg gta acc ccc gag ggg gtg cca gtg ggt gag agg tat tgt aga    8201
Met Val Thr Pro Glu Gly Val Pro Val Gly Glu Arg Tyr Cys Arg
2535            2540                2545 tcc tca ggg gtc ttg acc acc agt gcg agc aac tgc ttg act tgc    8246
Ser Ser Gly Val Leu Thr Thr Ser Ala Ser Asn Cys Leu Thr Cys
2550            2555                2560 tat atc aag gtg aaa gcc gcc tgt gag agg gtg ggg ctg aaa aat    8291
Tyr Ile Lys Val Lys Ala Ala Cys Glu Arg Val Gly Leu Lys Asn
2565            2570                2575 gtc tcg ctc ctc atc gct ggc gat gac tgt ttg atc ata tgc gaa    8336
Val Ser Leu Leu Ile Ala Gly Asp Asp Cys Leu Ile Ile Cys Glu
2580            2585                2590 cgg cct gtg tgc gat cct agc gac gct ttg ggc aga gcc ctg gcg    8381
Arg Pro Val Cys Asp Pro Ser Asp Ala Leu Gly Arg Ala Leu Ala
2595            2600                2605 agc tac ggg tac gca tgc gag cct tcg tat cat gca tca ctg gac    8426
Ser Tyr Gly Tyr Ala Cys Glu Pro Ser Tyr His Ala Ser Leu Asp
2610            2615                2620 acg gcc ccc ttc tgc tcc act tgg cta gct gag tgc aat gca gat    8471
Thr Ala Pro Phe Cys Ser Thr Trp Leu Ala Glu Cys Asn Ala Asp
2625            2630                2635 ggg aaa cgc cat ttc ttc ctg acc acg gac ttt cgg agg ccc ctc    8516
Gly Lys Arg His Phe Phe Leu Thr Thr Asp Phe Arg Arg Pro Leu
2640            2645                2650 gct cgc atg tcg agc gag tac agt gac cca atg gct tcg gcc atc    8561
Ala Arg Met Ser Ser Glu Tyr Ser Asp Pro Met Ala Ser Ala Ile
2655            2660                2665 ggt tac atc ctc cta tac cct tgg cat cct atc aca cgg tgg gtc    8606
Gly Tyr Ile Leu Leu Tyr Pro Trp His Pro Ile Thr Arg Trp Val
2670            2675                2680 atc atc cct cac gtg ctc acc tgc gcg ttt agg ggt ggt ggc aca    8651
Ile Ile Pro His Val Leu Thr Cys Ala Phe Arg Gly Gly Gly Thr
2685            2690                2695

-continued

| | | | | | | | | | | | | | | |
|---|---|---|---|---|---|---|---|---|---|---|---|---|---|---|
| ccg | tct | gat | cct | gtg | tgg | tgc | cag | gta | cat | ggt | aat | tac | tac | aag | 8696 |
| Pro | Ser | Asp | Pro | Val | Trp | Cys | Gln | Val | His | Gly | Asn | Tyr | Tyr | Lys | |
| 2700 | | | | 2705 | | | | | 2710 | | | | | | |

| | | | | | | | | | | | | | | |
|---|---|---|---|---|---|---|---|---|---|---|---|---|---|---|
| ttt | cca | ctg | gac | aaa | ctg | cct | aac | atc | atc | gtg | gcc | ctc | cac | gga | 8741 |
| Phe | Pro | Leu | Asp | Lys | Leu | Pro | Asn | Ile | Ile | Val | Ala | Leu | His | Gly | |
| 2715 | | | | 2720 | | | | | 2725 | | | | | | |

| | | | | | | | | | | | | | | |
|---|---|---|---|---|---|---|---|---|---|---|---|---|---|---|
| cca | gca | gcg | ttg | agg | gtt | acc | gca | gac | aca | act | aag | aca | aaa | atg | 8786 |
| Pro | Ala | Ala | Leu | Arg | Val | Thr | Ala | Asp | Thr | Thr | Lys | Thr | Lys | Met | |
| 2730 | | | | 2735 | | | | | 2740 | | | | | | |

| | | | | | | | | | | | | | | |
|---|---|---|---|---|---|---|---|---|---|---|---|---|---|---|
| gag | gct | ggc | aag | gtg | ctg | agc | gac | ctc | aag | ctc | cct | ggc | cta | gca | 8831 |
| Glu | Ala | Gly | Lys | Val | Leu | Ser | Asp | Leu | Lys | Leu | Pro | Gly | Leu | Ala | |
| 2745 | | | | 2750 | | | | | 2755 | | | | | | |

| | | | | | | | | | | | | | | |
|---|---|---|---|---|---|---|---|---|---|---|---|---|---|---|
| gtc | cac | cgg | aag | aag | gcc | ggg | gca | ttg | cga | acg | cgt | atg | ctc | cgg | 8876 |
| Val | His | Arg | Lys | Lys | Ala | Gly | Ala | Leu | Arg | Thr | Arg | Met | Leu | Arg | |
| 2760 | | | | 2765 | | | | | 2770 | | | | | | |

| | | | | | | | | | | | | | | |
|---|---|---|---|---|---|---|---|---|---|---|---|---|---|---|
| tcg | cgc | ggt | tgg | gct | gag | ttg | gct | agg | ggg | ctg | ttg | tgg | cgt | cca | 8921 |
| Ser | Arg | Gly | Trp | Ala | Glu | Leu | Ala | Arg | Gly | Leu | Leu | Trp | Arg | Pro | |
| 2775 | | | | 2780 | | | | | 2785 | | | | | | |

| | | | | | | | | | | | | | | |
|---|---|---|---|---|---|---|---|---|---|---|---|---|---|---|
| ggc | ctg | cgg | ctt | ccc | cct | ccg | gag | att | gct | ggt | atc | ccc | ggg | ggt | 8966 |
| Gly | Leu | Arg | Leu | Pro | Pro | Pro | Glu | Ile | Ala | Gly | Ile | Pro | Gly | Gly | |
| 2790 | | | | 2795 | | | | | 2800 | | | | | | |

| | | | | | | | | | | | | | | |
|---|---|---|---|---|---|---|---|---|---|---|---|---|---|---|
| ttc | ccc | ctt | tcc | ccc | ccc | tat | atg | ggg | gtg | gtt | cat | caa | ttg | gat | 9011 |
| Phe | Pro | Leu | Ser | Pro | Pro | Tyr | Met | Gly | Val | Val | His | Gln | Leu | Asp | |
| 2805 | | | | 2810 | | | | | 2815 | | | | | | |

| | | | | | | | | | | | | | | |
|---|---|---|---|---|---|---|---|---|---|---|---|---|---|---|
| ttc | aca | agc | cag | agg | agt | cgc | tgg | cgg | tgg | ttg | ggg | ttc | tta | gcc | 9056 |
| Phe | Thr | Ser | Gln | Arg | Ser | Arg | Trp | Arg | Trp | Leu | Gly | Phe | Leu | Ala | |
| 2820 | | | | 2825 | | | | | 2830 | | | | | | |

| | | | | | | | | | |
|---|---|---|---|---|---|---|---|---|---|
| ctg | ctc | atc | gta | gcc | ctc | ttc | ggg | tga | actaaattca tctgttgcgg | 9103 |
| Leu | Leu | Ile | Val | Ala | Leu | Phe | Gly | | | |
| 2835 | | | | 2840 | | | | | | | caaggtccgg tgactgatca tcactggagg aggttcccgc cctccccgcc ccaggggtct 9163 cccccgctggg taaaaagggc ccggccttgg gaggcatggt ggttactaac ccctggcag 9223 ggtcaaagcc tgatggtgct aatgcactgc cacttcggtg gcgggtcgct accttatagc 9283 gtaatccgtg actacgggct gctcgcagag ccctcccccgg atggggcaca gtgcactgtg 9343 atctgaaggg gtgcaccccg gtaagagctc ggcccaaagg ccgggttcta ct 9395

<210> SEQ ID NO 2
<211> LENGTH: 2842
<212> TYPE: PRT
<213> ORGANISM: Hepatitis GB Virus C

<400> SEQUENCE: 2

Met Ala Val Leu Leu Leu Leu Val Val Glu Ala Gly Ala Ile Leu
1               5                   10                  15

Ala Pro Ala Thr His Ala Cys Arg Ala Asn Gly Gln Tyr Phe Leu Thr
                20                  25                  30

Asn Cys Cys Ala Pro Glu Asp Ile Gly Phe Cys Leu Glu Gly Gly Cys
            35                  40                  45

Leu Val Ala Leu Gly Cys Thr Val Cys Thr Asp Arg Cys Trp Pro Leu
        50                  55                  60

Tyr Gln Ala Gly Leu Ala Val Arg Pro Gly Lys Ser Ala Ala Gln Leu
65                  70                  75                  80

Val Gly Glu Leu Gly Ser Leu Tyr Gly Pro Leu Ser Val Ser Ala Tyr
                85                  90                  95

Val Ala Gly Ile Leu Gly Leu Gly Glu Val Tyr Ser Gly Val Leu Thr
            100                 105                 110

```
Val Gly Val Ala Leu Arg Arg Val Tyr Leu Met Pro Asn Leu Lys
        115                 120                 125

Cys Ala Val Glu Cys Asp Val Lys Trp Gly Ser Glu Phe Trp Arg Trp
    130                 135                 140

Thr Glu Gln Leu Ala Ser Asn Tyr Trp Ile Leu Glu Tyr Leu Trp Lys
145                 150                 155                 160

Val Pro Phe Glu Phe Trp Arg Gly Val Met Ser Leu Thr Pro Leu Leu
                165                 170                 175

Val Trp Val Ala Ala Leu Leu Leu Glu Gln Arg Ile Val Met Val
                180                 185                 190

Phe Leu Leu Val Thr Met Ala Gly Met Leu Gln Gly Ala Pro Ala Ser
            195                 200                 205

Val Leu Gly Ser Arg Pro Phe Asp Tyr Gly Leu Lys Trp Gln Ser Cys
        210                 215                 220

Ser Cys Arg Ala Asn Gly Ser Arg Ile Pro Thr Gly Glu Arg Val Trp
225                 230                 235                 240

Asp Arg Gly Asn Val Thr Leu Leu Cys Asp Cys Pro Asn Gly Pro Trp
                245                 250                 255

Val Trp Val Pro Ala Phe Cys Gln Ala Val Gly Trp Gly Asp Pro Ile
                260                 265                 270

Thr His Trp Ser His Gly Gln Asn Gln Trp Pro Leu Ser Cys Pro Gln
            275                 280                 285

Tyr Val Tyr Gly Ser Val Ser Val Thr Cys Val Trp Gly Ser Val Ser
        290                 295                 300

Trp Phe Ala Ser Thr Gly Gly Arg Asp Ser Lys Ile Asp Val Trp Ser
305                 310                 315                 320

Leu Val Pro Val Gly Ser Ala Ser Cys Thr Ile Ala Ala Leu Gly Ser
                325                 330                 335

Ser Asp Arg Asp Thr Val Val Glu Leu Ser Glu Trp Gly Val Pro Cys
            340                 345                 350

Val Thr Cys Ile Leu Asp Arg Arg Pro Ala Ser Cys Gly Thr Cys Val
        355                 360                 365

Arg Asp Cys Trp Pro Glu Thr Gly Ser Val Arg Phe Pro Phe His Arg
            370                 375                 380

Cys Gly Thr Gly Pro Arg Leu Thr Lys Asp Leu Glu Ala Val Pro Phe
385                 390                 395                 400

Val Asn Arg Thr Thr Pro Phe Thr Ile Arg Gly Pro Leu Gly Asn Gln
                405                 410                 415

Gly Arg Gly Asn Pro Val Arg Ser Pro Leu Gly Phe Gly Ser Tyr Thr
                420                 425                 430

Met Thr Lys Ile Arg Asp Ser Leu His Leu Val Lys Cys Pro Thr Pro
            435                 440                 445

Ala Ile Glu Pro Pro Thr Gly Thr Phe Gly Phe Pro Gly Val Pro
450                 455                 460

Pro Ile Asn Asn Cys Met Pro Leu Gly Thr Glu Val Ser Glu Ala Leu
465                 470                 475                 480

Gly Gly Ala Gly Leu Thr Gly Gly Phe Tyr Glu Pro Leu Val Arg Arg
                485                 490                 495

Cys Ser Glu Leu Met Gly Arg Arg Asn Pro Val Cys Pro Gly Tyr Ala
                500                 505                 510

Trp Leu Ser Ser Gly Arg Pro Asp Gly Phe Ile His Val Gln Gly His
            515                 520                 525
```

-continued

```
Leu Gln Glu Val Asp Ala Gly Asn Phe Ile Pro Pro Arg Trp Leu
    530                 535                 540

Leu Leu Asp Phe Val Phe Val Leu Leu Tyr Leu Met Lys Leu Ala Glu
545                 550                 555                 560

Ala Arg Leu Val Pro Leu Ile Leu Leu Leu Trp Trp Trp Val Asn
                565                 570                 575

Gln Leu Ala Val Leu Gly Leu Pro Ala Val Asp Ala Ala Val Ala Gly
                580                 585                 590

Glu Val Phe Ala Gly Pro Ala Leu Ser Trp Cys Leu Gly Leu Pro Thr
        595                 600                 605

Val Ser Met Ile Leu Gly Leu Ala Asn Leu Val Leu Tyr Phe Arg Trp
        610                 615                 620

Met Gly Pro Gln Arg Leu Met Phe Leu Val Leu Trp Lys Leu Ala Arg
625                 630                 635                 640

Gly Ala Phe Pro Leu Ala Leu Leu Met Gly Ile Ser Ala Thr Arg Gly
                645                 650                 655

Arg Thr Ser Val Leu Gly Ala Glu Phe Cys Phe Asp Val Thr Phe Glu
                660                 665                 670

Val Asp Thr Ser Val Leu Gly Trp Val Val Ala Ser Val Ala Trp
        675                 680                 685

Ala Ile Ala Leu Leu Ser Ser Met Ser Ala Gly Gly Trp Lys His Lys
        690                 695                 700

Ala Val Ile Tyr Arg Thr Trp Cys Lys Gly Tyr Gln Ala Val Arg Gln
705                 710                 715                 720

Arg Val Val Arg Ser Pro Leu Gly Glu Gly Arg Pro Thr Lys Leu Leu
                725                 730                 735

Thr Phe Ala Trp Cys Leu Ala Ser Tyr Ile Trp Pro Asp Ala Val Met
                740                 745                 750

Met Val Val Val Ala Leu Val Leu Phe Gly Leu Phe Asp Ala Leu
        755                 760                 765

Asp Trp Ala Leu Glu Glu Leu Leu Val Ser Arg Pro Ser Leu Arg Arg
        770                 775                 780

Leu Ala Arg Val Val Glu Cys Cys Val Met Ala Gly Glu Lys Ala Thr
785                 790                 795                 800

Thr Ile Arg Leu Val Ser Lys Met Cys Ala Arg Gly Ala Tyr Leu Phe
                805                 810                 815

Asp His Met Gly Ser Phe Ser Arg Ala Val Lys Glu Arg Leu Leu Glu
                820                 825                 830

Trp Asp Ala Ala Leu Glu Pro Leu Ser Phe Thr Arg Thr Asp Cys Arg
        835                 840                 845

Ile Ile Arg Asp Ala Ala Arg Thr Leu Ser Cys Gly Gln Cys Val Met
        850                 855                 860

Gly Leu Pro Val Val Ala Arg Arg Gly Asp Glu Val Leu Ile Gly Val
865                 870                 875                 880

Phe Gln Asp Val Asn His Leu Pro Pro Gly Phe Val Pro Thr Ala Pro
                885                 890                 895

Val Val Ile Arg Arg Cys Gly Lys Gly Phe Leu Gly Val Thr Lys Ala
                900                 905                 910

Ala Leu Thr Gly Arg Asp Pro Asp Leu His Pro Gly Asn Val Met Val
        915                 920                 925

Leu Gly Thr Ala Thr Ser Arg Ser Met Gly Thr Cys Leu Asn Gly Leu
        930                 935                 940

Leu Phe Thr Thr Phe His Gly Ala Ser Ser Arg Thr Ile Ala Thr Pro
```

```
                945                 950                 955                 960
            Val Gly Ala Leu Asn Pro Arg Trp Trp Ser Ala Ser Asp Asp Val Thr
                            965                 970                 975
            Val Tyr Pro Leu Pro Asp Gly Ala Thr Ser Leu Thr Pro Cys Thr Cys
                            980                 985                 990
            Gln Ala Glu Ser Cys Trp Val Ile Arg Ser Asp Gly Ala Leu Cys His
                            995                 1000                1005
            Gly Leu Ser Lys Gly Asp Lys Val Glu Leu Asp Val Ala Met Glu
                1010                1015                1020
            Val Ser Asp Phe Arg Gly Ser Ser Gly Ser Pro Val Leu Cys Asp
                1025                1030                1035
            Lys Gly His Ala Val Arg Met Leu Val Ser Val Leu His Ser Gly
                1040                1045                1050
            Gly Arg Val Thr Ala Ala Arg Phe Thr Arg Pro Trp Thr Gln Val
                1055                1060                1065
            Pro Thr Asp Ala Lys Thr Thr Thr Glu Pro Pro Val Pro Ala
                1070                1075                1080
            Lys Gly Val Phe Lys Glu Ala Pro Leu Phe Met Pro Thr Gly Ala
                1085                1090                1095
            Gly Lys Ser Thr Arg Val Pro Leu Glu Tyr Gly Asn Met Gly His
                1100                1105                1110
            Lys Val Leu Ile Leu Asn Pro Ser Val Ala Thr Val Arg Ala Met
                1115                1120                1125
            Gly Pro Tyr Met Glu Arg Leu Ala Gly Lys His Pro Ser Ile Tyr
                1130                1135                1140
            Cys Gly His Asp Thr Thr Ala Phe Thr Arg Ile Thr Asp Ser Pro
                1145                1150                1155
            Leu Thr Tyr Ser Thr Tyr Gly Arg Phe Leu Ala Asn Pro Arg Gln
                1160                1165                1170
            Met Leu Arg Gly Val Ser Val Val Ile Cys Asp Glu Cys His Ser
                1175                1180                1185
            His Asp Ser Thr Val Leu Leu Gly Ile Gly Arg Val Arg Glu Leu
                1190                1195                1200
            Ala Arg Gly Cys Gly Val Gln Leu Val Leu Tyr Ala Thr Ala Thr
                1205                1210                1215
            Pro Pro Gly Ser Pro Met Thr Gln His Pro Ser Ile Ile Glu Thr
                1220                1225                1230
            Lys Leu Asp Val Gly Glu Ile Pro Phe Tyr Gly His Gly Ile Pro
                1235                1240                1245
            Leu Glu Arg Met Arg Thr Gly Arg His Leu Val Phe Cys His Ser
                1250                1255                1260
            Lys Ala Glu Cys Glu Arg Leu Ala Gly Gln Phe Ser Ala Arg Gly
                1265                1270                1275
            Val Asn Ala Ile Ala Tyr Tyr Arg Gly Lys Asp Ser Ser Ile Ile
                1280                1285                1290
            Lys Asp Gly Asp Leu Val Val Cys Ala Thr Asp Ala Leu Ser Thr
                1295                1300                1305
            Gly Tyr Thr Gly Asn Phe Asp Ser Val Thr Asp Cys Gly Leu Val
                1310                1315                1320
            Val Glu Glu Val Val Glu Val Thr Leu Asp Pro Thr Ile Thr Ile
                1325                1330                1335
            Ser Leu Arg Thr Val Pro Ala Ser Ala Glu Leu Ser Met Gln Arg
                1340                1345                1350
```

```
Arg Gly Arg Thr Gly Arg Gly Arg Ser Gly Arg Tyr Tyr Tyr Ala
    1355            1360                1365
Gly Val Gly Lys Ala Pro Ala Gly Val Val Arg Ser Gly Pro Val
    1370            1375                1380
Trp Ser Ala Val Glu Ala Gly Val Thr Trp Tyr Gly Met Glu Pro
    1385            1390                1395
Asp Leu Thr Ala Asn Leu Leu Arg Leu Tyr Asp Asn Cys Pro Tyr
    1400            1405                1410
Thr Ala Ala Val Ala Ala Asp Ile Gly Glu Ala Val Phe Phe
    1415            1420                1425
Ser Gly Leu Ala Pro Leu Arg Met His Pro Asp Val Ser Trp Ala
    1430            1435                1440
Lys Val Arg Gly Val Asn Trp Pro Phe Leu Val Gly Val Gln Arg
    1445            1450                1455
Thr Met Cys Arg Glu Thr Leu Ser Pro Gly Pro Ser Asp Asp Pro
    1460            1465                1470
Gln Trp Ala Gly Leu Lys Gly Pro Asn Pro Val Pro Leu Leu Leu
    1475            1480                1485
Arg Trp Gly Asn Asp Leu Pro Ser Lys Val Ala Gly His His Ile
    1490            1495                1500
Val Asp Asp Leu Val Arg Arg Leu Gly Val Ala Glu Gly Tyr Val
    1505            1510                1515
Arg Cys Asp Ala Gly Pro Ile Leu Met Val Gly Leu Ala Ile Ala
    1520            1525                1530
Gly Gly Met Ile Tyr Ala Ser Tyr Thr Gly Ser Leu Val Val Val
    1535            1540                1545
Thr Asp Trp Asp Val Lys Gly Gly Gly Ser Pro Leu Tyr Arg His
    1550            1555                1560
Gly Asp Gln Ala Thr Pro Gln Pro Val Val Gln Val Pro Pro Val
    1565            1570                1575
Asp His Arg Pro Gly Gly Glu Ser Ala Pro Ser Asp Ala Asn Thr
    1580            1585                1590
Val Thr Asp Ala Val Ala Ala Ile Gln Val Asp Cys Asp Trp Ser
    1595            1600                1605
Val Met Thr Leu Ser Ile Gly Glu Val Leu Ser Leu Ala Gln Ala
    1610            1615                1620
Lys Thr Ala Glu Ala Tyr Ala Ala Thr Thr Lys Trp Leu Ala Gly
    1625            1630                1635
Cys Tyr Thr Gly Thr Arg Ala Val Pro Thr Val Ser Ile Val Asp
    1640            1645                1650
Lys Leu Phe Ala Gly Gly Trp Ala Ala Val Val Gly His Cys His
    1655            1660                1665
Ser Val Ile Ala Ala Ala Val Ala Ala Tyr Gly Ala Ser Arg Ser
    1670            1675                1680
Pro Pro Leu Ala Ala Ala Ala Ser Tyr Leu Met Gly Leu Gly Val
    1685            1690                1695
Gly Gly Asn Ala Gln Thr Arg Leu Ala Ser Ala Leu Leu Leu Gly
    1700            1705                1710
Ala Ala Gly Thr Ala Leu Gly Thr Pro Val Val Gly Leu Thr Met
    1715            1720                1725
Ala Gly Ala Phe Met Gly Ser Ala Ser Val Ser Pro Ser Leu Val
    1730            1735                1740
```

```
Thr Ile Leu Leu Gly Ala Val Gly Gly Trp Glu Gly Val Val Asn
1745                1750                1755

Ala Ala Ser Leu Val Phe Asp Phe Met Ala Gly Lys Leu Ser Ser
1760                1765                1770

Glu Asp Leu Trp Tyr Ala Ile Pro Val Leu Thr Ser Pro Gly Ala
1775                1780                1785

Gly Leu Ala Gly Ile Ala Leu Gly Leu Val Leu Tyr Ser Ala Asn
1790                1795                1800

Asn Ser Gly Thr Thr Thr Trp Leu Asn Arg Leu Leu Thr Thr Leu
1805                1810                1815

Pro Arg Ser Ser Cys Ile Pro Asp Ser Tyr Phe Gln Gln Ala Asp
1820                1825                1830

Tyr Cys Asp Lys Val Ser Ala Val Leu Arg Arg Leu Ser Leu Thr
1835                1840                1845

Arg Thr Val Val Ala Leu Val Asn Arg Glu Pro Lys Val Asp Glu
1850                1855                1860

Val Gln Val Gly Tyr Val Trp Asp Leu Trp Glu Trp Ile Met Arg
1865                1870                1875

Gln Val Arg Met Val Met Ala Arg Leu Arg Ala Leu Cys Pro Val
1880                1885                1890

Val Ser Leu Pro Leu Trp His Cys Gly Glu Gly Trp Ser Gly Glu
1895                1900                1905

Trp Leu Leu Asp Gly His Val Glu Ser Arg Cys Leu Cys Gly Cys
1910                1915                1920

Val Ile Thr Gly Asp Val Leu Asn Gly Gln Leu Lys Asp Pro Val
1925                1930                1935

Tyr Ser Thr Lys Leu Cys Arg His Tyr Trp Met Gly Thr Val Pro
1940                1945                1950

Val Asn Met Leu Gly Tyr Gly Glu Thr Ser Pro Leu Leu Ala Ser
1955                1960                1965

Asp Thr Pro Lys Val Val Pro Phe Gly Thr Ser Gly Trp Ala Glu
1970                1975                1980

Val Val Val Thr Pro Thr His Val Val Ile Arg Arg Thr Ser Ala
1985                1990                1995

Tyr Lys Leu Leu Arg Gln Gln Ile Leu Ser Ala Ala Val Ala Glu
2000                2005                2010

Pro Tyr Tyr Val Asp Gly Ile Pro Val Ser Trp Asp Ala Asp Ala
2015                2020                2025

Arg Ala Pro Ala Met Val Tyr Gly Pro Gly Gln Ser Val Thr Ile
2030                2035                2040

Asp Gly Glu Arg Tyr Thr Leu Pro His Gln Leu Arg Leu Arg Asn
2045                2050                2055

Val Ala Pro Ser Glu Val Ser Ser Glu Val Ser Ile Asp Ile Gly
2060                2065                2070

Thr Glu Thr Glu Asp Ser Glu Leu Thr Glu Ala Asp Leu Pro Pro
2075                2080                2085

Ala Ala Ala Ala Leu Gln Ala Ile Glu Asn Ala Ala Arg Ile Leu
2090                2095                2100

Glu Pro His Ile Asp Val Ile Met Glu Asp Cys Ser Thr Pro Ser
2105                2110                2115

Leu Cys Gly Ser Ser Arg Glu Met Pro Val Trp Gly Glu Asp Ile
2120                2125                2130

Pro Arg Thr Pro Ser Pro Ala Leu Ile Ser Val Thr Glu Ser Ser
```

```
                    2135                2140                2145

Pro  Asp  Glu  Lys  Thr  Pro  Ser  Val  Ser  Ser  Gln  Glu  Asp  Thr
               2150                2155                2160

Pro  Ser  Ser  Asp  Ser  Phe  Glu  Val  Ile  Gln  Glu  Ser  Glu  Thr  Ala
          2165                2170                2175

Glu  Gly  Glu  Glu  Ser  Val  Phe  Asn  Val  Ala  Leu  Ser  Val  Leu  Lys
     2180                2185                2190

Ala  Leu  Phe  Pro  Gln  Ser  Asp  Ala  Thr  Arg  Lys  Leu  Thr  Val  Lys
2195                2200                2205

Met  Ser  Cys  Cys  Val  Glu  Lys  Ser  Val  Thr  Arg  Phe  Phe  Ser  Leu
          2210                2215                2220

Gly  Leu  Thr  Val  Ala  Asp  Val  Ala  Ser  Leu  Cys  Glu  Met  Glu  Ile
     2225                2230                2235

Gln  Asn  His  Thr  Ala  Tyr  Cys  Asp  Lys  Val  Arg  Thr  Pro  Leu  Glu
2240                2245                2250

Leu  Gln  Val  Gly  Cys  Leu  Val  Gly  Asn  Glu  Leu  Thr  Phe  Glu  Cys
          2255                2260                2265

Asp  Lys  Cys  Glu  Ala  Arg  Gln  Glu  Thr  Leu  Ala  Ser  Phe  Ser  Tyr
     2270                2275                2280

Ile  Trp  Ser  Gly  Val  Pro  Leu  Thr  Arg  Ala  Thr  Pro  Ala  Lys  Pro
2285                2290                2295

Pro  Val  Val  Arg  Pro  Val  Gly  Ser  Leu  Leu  Val  Ala  Asp  Thr  Thr
     2300                2305                2310

Lys  Val  Tyr  Val  Thr  Asn  Pro  Asp  Asn  Val  Gly  Arg  Arg  Val  Asp
     2315                2320                2325

Lys  Val  Thr  Phe  Trp  Arg  Ala  Pro  Arg  Val  His  Asp  Lys  Phe  Leu
     2330                2335                2340

Val  Asp  Ser  Ile  Glu  Arg  Ala  Lys  Arg  Ala  Ala  Gln  Ala  Cys  Leu
     2345                2350                2355

Ser  Met  Gly  Tyr  Thr  Tyr  Glu  Glu  Ala  Ile  Arg  Thr  Val  Arg  Pro
     2360                2365                2370

His  Ala  Ala  Met  Gly  Trp  Gly  Ser  Lys  Val  Ser  Val  Lys  Asp  Leu
     2375                2380                2385

Ala  Thr  Pro  Ala  Gly  Lys  Met  Ala  Val  His  Asp  Arg  Leu  Gln  Glu
     2390                2395                2400

Ile  Leu  Glu  Gly  Thr  Pro  Val  Pro  Phe  Thr  Leu  Thr  Val  Lys  Lys
     2405                2410                2415

Glu  Val  Phe  Phe  Lys  Asp  Arg  Lys  Glu  Glu  Lys  Ala  Pro  Arg  Leu
     2420                2425                2430

Ile  Val  Phe  Pro  Pro  Leu  Asp  Phe  Arg  Ile  Ala  Glu  Lys  Leu  Ile
     2435                2440                2445

Leu  Gly  Asp  Pro  Gly  Arg  Val  Ala  Lys  Ala  Val  Leu  Gly  Gly  Ala
     2450                2455                2460

Tyr  Ala  Phe  Gln  Tyr  Thr  Pro  Asn  Gln  Arg  Ile  Arg  Glu  Met  Leu
     2465                2470                2475

Lys  Leu  Trp  Glu  Ser  Lys  Lys  Thr  Pro  Cys  Ala  Ile  Cys  Val  Asp
     2480                2485                2490

Ala  Thr  Cys  Phe  Asp  Ser  Ser  Ile  Thr  Glu  Glu  Asp  Val  Ala  Leu
     2495                2500                2505

Glu  Thr  Glu  Leu  Tyr  Ala  Leu  Ala  Ser  Asp  His  Pro  Glu  Trp  Val
     2510                2515                2520

Arg  Ala  Leu  Gly  Lys  Tyr  Tyr  Ala  Ser  Gly  Thr  Met  Val  Thr  Pro
     2525                2530                2535
```

```
Glu Gly Val Pro Val Gly Glu Arg Tyr Cys Arg Ser Ser Gly Val
        2540                2545                2550

Leu Thr Thr Ser Ala Ser Asn Cys Leu Thr Cys Tyr Ile Lys Val
    2555                2560                2565

Lys Ala Ala Cys Glu Arg Val Gly Leu Lys Asn Val Ser Leu Leu
    2570                2575                2580

Ile Ala Gly Asp Asp Cys Leu Ile Ile Cys Glu Arg Pro Val Cys
    2585                2590                2595

Asp Pro Ser Asp Ala Leu Gly Arg Ala Leu Ala Ser Tyr Gly Tyr
    2600                2605                2610

Ala Cys Glu Pro Ser Tyr His Ala Ser Leu Asp Thr Ala Pro Phe
    2615                2620                2625

Cys Ser Thr Trp Leu Ala Glu Cys Asn Ala Asp Gly Lys Arg His
    2630                2635                2640

Phe Phe Leu Thr Thr Asp Phe Arg Arg Pro Leu Ala Arg Met Ser
    2645                2650                2655

Ser Glu Tyr Ser Asp Pro Met Ala Ser Ala Ile Gly Tyr Ile Leu
    2660                2665                2670

Leu Tyr Pro Trp His Pro Ile Thr Arg Trp Val Ile Ile Pro His
    2675                2680                2685

Val Leu Thr Cys Ala Phe Arg Gly Gly Gly Thr Pro Ser Asp Pro
    2690                2695                2700

Val Trp Cys Gln Val His Gly Asn Tyr Tyr Lys Phe Pro Leu Asp
    2705                2710                2715

Lys Leu Pro Asn Ile Ile Val Ala Leu His Gly Pro Ala Ala Leu
    2720                2725                2730

Arg Val Thr Ala Asp Thr Thr Lys Thr Lys Met Glu Ala Gly Lys
    2735                2740                2745

Val Leu Ser Asp Leu Lys Leu Pro Gly Leu Ala Val His Arg Lys
    2750                2755                2760

Lys Ala Gly Ala Leu Arg Thr Arg Met Leu Arg Ser Arg Gly Trp
    2765                2770                2775

Ala Glu Leu Ala Arg Gly Leu Leu Trp Arg Pro Gly Leu Arg Leu
    2780                2785                2790

Pro Pro Pro Glu Ile Ala Gly Ile Pro Gly Gly Phe Pro Leu Ser
    2795                2800                2805

Pro Pro Tyr Met Gly Val Val His Gln Leu Asp Phe Thr Ser Gln
    2810                2815                2820

Arg Ser Arg Trp Arg Trp Leu Gly Phe Leu Ala Leu Leu Ile Val
    2825                2830                2835

Ala Leu Phe Gly
    2840

<210> SEQ ID NO 3
<211> LENGTH: 2842
<212> TYPE: PRT
<213> ORGANISM: Hepatitis GB virus C

<400> SEQUENCE: 3

Met Ala Val Leu Leu Leu Leu Val Val Glu Ala Gly Ala Ile Leu
1               5                   10                  15

Ala Pro Ala Thr His Ala Cys Arg Ala Asn Gly Gln Tyr Phe Leu Thr
                20                  25                  30

Asn Cys Cys Ala Pro Glu Asp Ile Gly Phe Cys Leu Glu Gly Gly Cys
```

```
                35                  40                  45
Leu Val Ala Leu Gly Cys Thr Val Cys Thr Asp Arg Cys Trp Pro Leu
             50                  55                  60
Tyr Gln Ala Gly Leu Ala Val Arg Pro Gly Lys Ser Ala Ala Gln Leu
 65                  70                  75                  80
Val Gly Glu Leu Gly Ser Leu Tyr Gly Pro Leu Ser Val Ser Ala Tyr
                 85                  90                  95
Val Ala Gly Ile Leu Gly Leu Gly Glu Val Tyr Ser Gly Val Leu Thr
                100                 105                 110
Val Gly Val Ala Leu Arg Arg Arg Val Tyr Leu Met Pro Asn Leu Lys
                115                 120                 125
Cys Ala Val Glu Cys Asp Val Lys Trp Gly Ser Glu Phe Trp Arg Trp
            130                 135                 140
Thr Glu Gln Leu Ala Ser Asn Tyr Trp Ile Leu Glu Tyr Leu Trp Lys
145                 150                 155                 160
Val Pro Phe Glu Phe Trp Arg Gly Val Met Ser Leu Thr Pro Leu Leu
                165                 170                 175
Val Trp Val Ala Ala Leu Leu Leu Glu Gln Arg Ile Val Met Val
            180                 185                 190
Phe Leu Leu Val Thr Met Ala Gly Met Leu Gln Gly Ala Pro Ala Ser
            195                 200                 205
Val Leu Gly Ser Arg Pro Phe Asp Tyr Gly Leu Lys Trp Gln Ser Cys
            210                 215                 220
Ser Cys Arg Ala Asn Gly Ser Arg Ile Pro Thr Gly Glu Arg Val Trp
225                 230                 235                 240
Asp Arg Gly Asn Val Thr Leu Leu Cys Asp Cys Pro Asn Gly Pro Trp
                245                 250                 255
Val Trp Val Pro Ala Phe Cys Gln Ala Val Gly Trp Gly Asp Pro Ile
            260                 265                 270
Thr His Trp Ser His Gly Gln Asn Gln Trp Pro Leu Ser Cys Pro Gln
            275                 280                 285
Tyr Val Tyr Gly Ser Val Ser Val Thr Cys Val Trp Gly Ser Val Ser
        290                 295                 300
Trp Phe Ala Ser Thr Gly Gly Arg Asp Ser Lys Ile Asp Val Trp Ser
305                 310                 315                 320
Leu Val Pro Val Gly Ser Ala Ser Cys Thr Ile Ala Ala Leu Gly Ser
                325                 330                 335
Ser Asp Arg Asp Thr Val Val Glu Leu Ser Glu Trp Gly Val Pro Cys
            340                 345                 350
Val Thr Cys Ile Leu Asp Arg Arg Pro Ala Ser Cys Gly Thr Cys Val
            355                 360                 365
Arg Asp Cys Trp Pro Glu Thr Gly Ser Val Arg Phe Pro Phe His Arg
    370                 375                 380
Cys Gly Thr Gly Pro Arg Leu Thr Lys Asp Leu Glu Ala Val Pro Phe
385                 390                 395                 400
Val Asn Arg Thr Thr Pro Phe Thr Ile Arg Gly Pro Leu Gly Asn Gln
                405                 410                 415
Gly Arg Gly Asn Pro Val Arg Ser Pro Leu Gly Phe Ser Tyr Thr
                420                 425                 430
Met Thr Lys Ile Arg Asp Ser Leu His Leu Val Lys Cys Pro Thr Pro
            435                 440                 445
Ala Ile Glu Pro Pro Thr Gly Thr Phe Gly Phe Phe Pro Gly Val Pro
            450                 455                 460
```

```
Pro Ile Asn Asn Cys Met Pro Leu Gly Thr Glu Val Ser Glu Ala Leu
465                 470                 475                 480

Gly Gly Ala Gly Leu Thr Gly Gly Phe Tyr Glu Pro Leu Val Arg Arg
            485                 490                 495

Cys Ser Glu Leu Met Gly Arg Arg Asn Pro Val Cys Pro Gly Tyr Ala
        500                 505                 510

Trp Leu Ser Ser Gly Arg Pro Asp Gly Phe Ile His Val Gln Gly His
            515                 520                 525

Leu Gln Glu Val Asp Ala Gly Asn Phe Ile Pro Pro Arg Trp Leu
    530                 535                 540

Leu Leu Asp Phe Val Phe Val Leu Leu Tyr Leu Met Lys Leu Ala Glu
545                 550                 555                 560

Ala Arg Leu Val Pro Leu Ile Leu Leu Leu Trp Trp Val Asn
                565                 570                 575

Gln Leu Ala Val Leu Gly Leu Pro Ala Val Asp Ala Ala Val Ala Gly
            580                 585                 590

Glu Val Phe Ala Gly Pro Ala Leu Ser Trp Cys Leu Gly Leu Pro Thr
        595                 600                 605

Val Ser Met Ile Leu Gly Leu Ala Asn Leu Val Leu Tyr Phe Arg Trp
    610                 615                 620

Met Gly Pro Gln Arg Leu Met Phe Leu Val Leu Trp Lys Leu Ala Arg
625                 630                 635                 640

Gly Ala Phe Pro Leu Ala Leu Leu Met Gly Ile Ser Ala Thr Arg Gly
                645                 650                 655

Arg Thr Ser Val Leu Gly Ala Glu Phe Cys Phe Asp Val Thr Phe Glu
            660                 665                 670

Val Asp Thr Ser Val Leu Gly Trp Val Val Ala Ser Val Ala Trp
    675                 680                 685

Ala Ile Ala Leu Leu Ser Ser Met Ser Ala Gly Gly Trp Lys His Lys
        690                 695                 700

Ala Val Ile Tyr Arg Thr Trp Cys Lys Gly Tyr Gln Ala Val Arg Gln
705                 710                 715                 720

Arg Val Val Arg Ser Pro Leu Gly Glu Gly Arg Pro Thr Lys Leu Leu
                725                 730                 735

Thr Phe Ala Trp Cys Leu Ala Ser Tyr Ile Trp Pro Asp Ala Val Met
            740                 745                 750

Met Val Val Ala Leu Val Leu Phe Gly Leu Phe Asp Ala Leu
    755                 760                 765

Asp Trp Ala Leu Glu Glu Leu Leu Val Ser Arg Pro Ser Leu Arg Arg
    770                 775                 780

Leu Ala Arg Val Val Glu Cys Cys Val Met Ala Gly Glu Lys Ala Thr
785                 790                 795                 800

Thr Ile Arg Leu Val Ser Lys Met Cys Ala Arg Gly Ala Tyr Leu Phe
                805                 810                 815

Asp His Met Gly Ser Phe Ser Arg Ala Val Lys Glu Arg Leu Leu Glu
            820                 825                 830

Trp Asp Ala Ala Leu Glu Pro Leu Ser Phe Thr Arg Thr Asp Cys Arg
    835                 840                 845

Ile Ile Arg Asp Ala Ala Arg Thr Leu Ser Cys Gly Gln Cys Val Met
        850                 855                 860

Gly Leu Pro Val Val Ala Arg Arg Gly Asp Glu Val Leu Ile Gly Val
865                 870                 875                 880
```

-continued

```
Phe Gln Asp Val Asn His Leu Pro Pro Gly Phe Val Pro Thr Ala Pro
                885                 890                 895

Val Val Ile Arg Arg Cys Gly Lys Gly Phe Leu Gly Val Thr Lys Ala
            900                 905                 910

Ala Leu Thr Gly Arg Asp Pro Asp Leu His Pro Gly Asn Val Met Val
            915                 920                 925

Leu Gly Thr Ala Thr Ser Arg Ser Met Gly Thr Cys Leu Asn Gly Leu
            930                 935                 940

Leu Phe Thr Thr Phe His Gly Ala Ser Ser Arg Thr Ile Ala Thr Pro
945                 950                 955                 960

Val Gly Ala Leu Asn Pro Arg Trp Trp Ser Ala Ser Asp Asp Val Thr
            965                 970                 975

Val Tyr Pro Leu Pro Asp Gly Ala Thr Ser Leu Thr Pro Cys Thr Cys
            980                 985                 990

Gln Ala Glu Ser Cys Trp Val Ile Arg Ser Asp Gly Ala Leu Cys His
            995                 1000                1005

Gly Leu Ser Lys Gly Asp Lys Val Glu Leu Asp Val Ala Met Glu
        1010                1015                1020

Val Ser Asp Phe Arg Gly Ser Ser Gly Ser Pro Val Leu Cys Asp
        1025                1030                1035

Lys Gly His Ala Val Arg Met Leu Val Ser Val Leu His Ser Gly
        1040                1045                1050

Gly Arg Val Thr Ala Ala Arg Phe Thr Arg Pro Trp Thr Gln Val
        1055                1060                1065

Pro Thr Asp Ala Lys Thr Thr Thr Glu Pro Pro Val Pro Ala
        1070                1075                1080

Lys Gly Val Phe Lys Glu Ala Pro Leu Phe Met Pro Thr Gly Ala
        1085                1090                1095

Gly Lys Ser Thr Arg Val Pro Leu Glu Tyr Gly Asn Met Gly His
        1100                1105                1110

Lys Val Leu Ile Leu Asn Pro Ser Val Ala Thr Val Arg Ala Met
        1115                1120                1125

Gly Pro Tyr Met Glu Arg Leu Ala Gly Lys His Pro Ser Ile Tyr
        1130                1135                1140

Cys Gly His Asp Thr Thr Ala Phe Thr Arg Ile Thr Asp Ser Pro
        1145                1150                1155

Leu Thr Tyr Ser Thr Tyr Gly Arg Phe Leu Ala Asn Pro Arg Gln
        1160                1165                1170

Met Leu Arg Gly Val Ser Val Val Ile Cys Asp Glu Cys His Ser
        1175                1180                1185

His Asp Ser Thr Val Leu Leu Gly Ile Gly Arg Val Arg Glu Leu
        1190                1195                1200

Ala Arg Gly Cys Gly Val Gln Leu Val Leu Tyr Ala Thr Ala Thr
        1205                1210                1215

Pro Pro Gly Ser Pro Met Thr Gln His Pro Ser Ile Ile Glu Thr
        1220                1225                1230

Lys Leu Asp Val Gly Glu Ile Pro Phe Tyr Gly His Gly Ile Pro
        1235                1240                1245

Leu Glu Arg Met Arg Thr Gly Arg His Leu Val Phe Cys His Ser
        1250                1255                1260

Lys Ala Glu Cys Glu Arg Leu Ala Gly Gln Phe Ser Ala Arg Gly
        1265                1270                1275

Val Asn Ala Ile Ala Tyr Tyr Arg Gly Lys Asp Ser Ser Ile Ile
```

-continued

```
            1280                 1285                 1290
Lys Asp Gly Asp Leu Val Val Cys Ala Thr Asp Ala Leu Ser Thr
            1295                 1300                 1305
Gly Tyr Thr Gly Asn Phe Asp Ser Val Thr Asp Cys Gly Leu Val
            1310                 1315                 1320
Val Glu Glu Val Val Glu Val Thr Leu Asp Pro Thr Ile Thr Ile
            1325                 1330                 1335
Ser Leu Arg Thr Val Pro Ala Ser Ala Glu Leu Ser Met Gln Arg
            1340                 1345                 1350
Arg Gly Arg Thr Gly Arg Gly Arg Ser Gly Arg Tyr Tyr Tyr Ala
            1355                 1360                 1365
Gly Val Gly Lys Ala Pro Ala Gly Val Val Arg Ser Gly Pro Val
            1370                 1375                 1380
Trp Ser Ala Val Glu Ala Gly Val Thr Trp Tyr Gly Met Glu Pro
            1385                 1390                 1395
Asp Leu Thr Ala Asn Leu Leu Arg Leu Tyr Asp Asn Cys Pro Tyr
            1400                 1405                 1410
Thr Ala Ala Val Ala Ala Asp Ile Gly Glu Ala Ala Val Phe Phe
            1415                 1420                 1425
Ser Gly Leu Ala Pro Leu Arg Met His Pro Asp Val Ser Trp Ala
            1430                 1435                 1440
Lys Val Arg Gly Val Asn Trp Pro Phe Leu Val Gly Val Gln Arg
            1445                 1450                 1455
Thr Met Cys Arg Glu Thr Leu Ser Pro Gly Pro Ser Asp Asp Pro
            1460                 1465                 1470
Gln Trp Ala Gly Leu Lys Gly Pro Asn Pro Val Pro Leu Leu Leu
            1475                 1480                 1485
Arg Trp Gly Asn Asp Leu Pro Ser Lys Val Ala Gly His His Ile
            1490                 1495                 1500
Val Asp Asp Leu Val Arg Arg Leu Gly Val Ala Glu Gly Tyr Val
            1505                 1510                 1515
Arg Cys Asp Ala Gly Pro Ile Leu Met Val Gly Leu Ala Ile Ala
            1520                 1525                 1530
Gly Gly Met Ile Tyr Ala Ser Tyr Thr Gly Ser Leu Val Val Val
            1535                 1540                 1545
Thr Asp Trp Asp Val Lys Gly Gly Gly Ser Pro Leu Tyr Arg His
            1550                 1555                 1560
Gly Asp Gln Ala Thr Pro Gln Pro Val Val Gln Val Pro Pro Val
            1565                 1570                 1575
Asp His Arg Pro Gly Gly Glu Ser Ala Pro Ser Asp Ala Asn Thr
            1580                 1585                 1590
Val Thr Asp Ala Val Ala Ala Ile Gln Val Asp Cys Asp Trp Ser
            1595                 1600                 1605
Val Met Thr Leu Ser Ile Gly Glu Val Leu Ser Leu Ala Gln Ala
            1610                 1615                 1620
Lys Thr Ala Glu Ala Tyr Ala Ala Thr Thr Lys Trp Leu Ala Gly
            1625                 1630                 1635
Cys Tyr Thr Gly Thr Arg Ala Val Pro Thr Val Ser Ile Val Asp
            1640                 1645                 1650
Lys Leu Phe Ala Gly Gly Trp Ala Ala Val Val Gly His Cys His
            1655                 1660                 1665
Ser Val Ile Ala Ala Ala Val Ala Ala Tyr Gly Ala Ser Arg Ser
            1670                 1675                 1680
```

-continued

Pro Pro Leu Ala Ala Ala Ser Tyr Leu Met Gly Leu Gly Val
1685            1690            1695

Gly Gly Asn Ala Gln Thr Arg Leu Ala Ser Ala Leu Leu Leu Gly
1700            1705            1710

Ala Ala Gly Thr Ala Leu Gly Thr Pro Val Val Gly Leu Thr Met
1715            1720            1725

Ala Gly Ala Phe Met Gly Ser Ala Ser Val Ser Pro Ser Leu Val
1730            1735            1740

Thr Ile Leu Leu Gly Ala Val Gly Gly Trp Glu Gly Val Val Asn
1745            1750            1755

Ala Ala Ser Leu Val Phe Asp Phe Met Ala Gly Lys Leu Ser Ser
1760            1765            1770

Glu Asp Leu Trp Tyr Ala Ile Pro Val Leu Thr Ser Pro Gly Ala
1775            1780            1785

Gly Leu Ala Gly Ile Ala Leu Gly Leu Val Leu Tyr Ser Ala Asn
1790            1795            1800

Asn Ser Gly Thr Thr Thr Trp Leu Asn Arg Leu Leu Thr Thr Leu
1805            1810            1815

Pro Arg Ser Ser Cys Ile Pro Asp Ser Tyr Phe Gln Gln Ala Asp
1820            1825            1830

Tyr Cys Asp Lys Val Ser Ala Val Leu Arg Arg Leu Ser Leu Thr
1835            1840            1845

Arg Thr Val Val Ala Leu Val Asn Arg Glu Pro Lys Val Asp Glu
1850            1855            1860

Val Gln Val Gly Tyr Val Trp Asp Leu Trp Glu Trp Ile Met Arg
1865            1870            1875

Gln Val Arg Met Val Met Ala Arg Leu Arg Ala Leu Cys Pro Val
1880            1885            1890

Val Ser Leu Pro Leu Trp His Cys Gly Glu Gly Trp Ser Gly Glu
1895            1900            1905

Trp Leu Leu Asp Gly His Val Glu Ser Arg Cys Leu Cys Gly Cys
1910            1915            1920

Val Ile Thr Gly Asp Val Leu Asn Gly Gln Leu Lys Asp Pro Val
1925            1930            1935

Tyr Ser Thr Lys Leu Cys Arg His Tyr Trp Met Gly Thr Val Pro
1940            1945            1950

Val Asn Met Leu Gly Tyr Gly Glu Thr Ser Pro Leu Leu Ala Ser
1955            1960            1965

Asp Thr Pro Lys Val Val Pro Phe Gly Thr Ser Gly Trp Ala Glu
1970            1975            1980

Val Val Val Thr Pro Thr His Val Val Ile Arg Arg Thr Ser Ala
1985            1990            1995

Tyr Lys Leu Leu Arg Gln Gln Ile Leu Ser Ala Ala Val Ala Glu
2000            2005            2010

Pro Tyr Tyr Val Asp Gly Ile Pro Val Ser Trp Asp Ala Asp Ala
2015            2020            2025

Arg Ala Pro Ala Met Val Tyr Gly Pro Gly Gln Ser Val Thr Ile
2030            2035            2040

Asp Gly Glu Arg Tyr Thr Leu Pro His Gln Leu Arg Leu Arg Asn
2045            2050            2055

Val Ala Pro Ser Glu Val Ser Ser Glu Val Ser Ile Asp Ile Gly
2060            2065            2070

```
Thr Glu Thr Glu Asp Ser Glu Leu Thr Glu Ala Asp Leu Pro Pro
2075                2080                2085

Ala Ala Ala Ala Leu Gln Ala Ile Glu Asn Ala Ala Arg Ile Leu
2090                2095                2100

Glu Pro His Ile Asp Val Ile Met Glu Asp Cys Ser Thr Pro Ser
2105                2110                2115

Leu Cys Gly Ser Ser Arg Glu Met Pro Val Trp Gly Glu Asp Ile
2120                2125                2130

Pro Arg Thr Pro Ser Pro Ala Leu Ile Ser Val Thr Glu Ser Ser
2135                2140                2145

Pro Asp Glu Lys Thr Pro Ser Val Ser Ser Ser Gln Glu Asp Thr
2150                2155                2160

Pro Ser Ser Asp Ser Phe Glu Val Ile Gln Glu Ser Glu Thr Ala
2165                2170                2175

Glu Gly Glu Glu Ser Val Phe Asn Val Ala Leu Ser Val Leu Lys
2180                2185                2190

Ala Leu Phe Pro Gln Ser Asp Ala Thr Arg Lys Leu Thr Val Lys
2195                2200                2205

Met Ser Cys Cys Val Glu Lys Ser Val Thr Arg Phe Phe Ser Leu
2210                2215                2220

Gly Leu Thr Val Ala Asp Val Ala Ser Leu Cys Glu Met Glu Ile
2225                2230                2235

Gln Asn His Thr Ala Tyr Cys Asp Lys Val Arg Thr Pro Leu Glu
2240                2245                2250

Leu Gln Val Gly Cys Leu Val Gly Asn Glu Leu Thr Phe Glu Cys
2255                2260                2265

Asp Lys Cys Glu Ala Arg Gln Glu Thr Leu Ala Ser Phe Ser Tyr
2270                2275                2280

Ile Trp Ser Gly Val Pro Leu Thr Arg Ala Thr Pro Ala Lys Pro
2285                2290                2295

Pro Val Val Arg Pro Val Gly Ser Leu Leu Val Ala Asp Thr Thr
2300                2305                2310

Lys Val Tyr Val Thr Asn Pro Asp Asn Val Gly Arg Arg Val Asp
2315                2320                2325

Lys Val Thr Phe Trp Arg Ala Pro Arg Val His Asp Lys Phe Leu
2330                2335                2340

Val Asp Ser Ile Glu Arg Ala Lys Arg Ala Ala Gln Ala Cys Leu
2345                2350                2355

Ser Met Gly Tyr Thr Tyr Glu Glu Ala Ile Arg Thr Val Arg Pro
2360                2365                2370

His Ala Ala Met Gly Trp Gly Ser Lys Val Ser Val Lys Asp Leu
2375                2380                2385

Ala Thr Pro Ala Gly Lys Met Ala Val His Asp Arg Leu Gln Glu
2390                2395                2400

Ile Leu Glu Gly Thr Pro Val Pro Phe Thr Leu Thr Val Lys Lys
2405                2410                2415

Glu Val Phe Phe Lys Asp Arg Lys Glu Glu Lys Ala Pro Arg Leu
2420                2425                2430

Ile Val Phe Pro Pro Leu Asp Phe Arg Ile Ala Glu Lys Leu Ile
2435                2440                2445

Leu Gly Asp Pro Gly Arg Val Ala Lys Ala Val Leu Gly Gly Ala
2450                2455                2460

Tyr Ala Phe Gln Tyr Thr Pro Asn Gln Arg Ile Arg Glu Met Leu
```

2465                2470                2475

Lys Leu Trp Glu Ser Lys Lys Thr Pro Cys Ala Ile Cys Val Asp
        2480                2485                2490

Ala Thr Cys Phe Asp Ser Ser Ile Thr Glu Glu Asp Val Ala Leu
        2495                2500                2505

Glu Thr Glu Leu Tyr Ala Leu Ala Ser Asp His Pro Glu Trp Val
        2510                2515                2520

Arg Ala Leu Gly Lys Tyr Tyr Ala Ser Gly Thr Met Val Thr Pro
        2525                2530                2535

Glu Gly Val Pro Val Gly Glu Arg Tyr Cys Arg Ser Ser Gly Val
        2540                2545                2550

Leu Thr Thr Ser Ala Ser Asn Cys Leu Thr Cys Tyr Ile Lys Val
        2555                2560                2565

Lys Ala Ala Cys Glu Arg Val Gly Leu Lys Asn Val Ser Leu Leu
        2570                2575                2580

Ile Ala Gly Asp Asp Cys Leu Ile Ile Cys Glu Arg Pro Val Cys
        2585                2590                2595

Asp Pro Ser Asp Ala Leu Gly Arg Ala Leu Ala Ser Tyr Gly Tyr
        2600                2605                2610

Ala Cys Glu Pro Ser Tyr His Ala Ser Leu Asp Thr Ala Pro Phe
        2615                2620                2625

Cys Ser Thr Trp Leu Ala Glu Cys Asn Ala Asp Gly Lys Arg His
        2630                2635                2640

Phe Phe Leu Thr Thr Asp Phe Arg Arg Pro Leu Ala Arg Met Ser
        2645                2650                2655

Ser Glu Tyr Ser Asp Pro Met Ala Ser Ala Ile Gly Tyr Ile Leu
        2660                2665                2670

Leu Tyr Pro Trp His Pro Ile Thr Arg Trp Val Ile Ile Pro His
        2675                2680                2685

Val Leu Thr Cys Ala Phe Arg Gly Gly Thr Pro Ser Asp Pro
        2690                2695                2700

Val Trp Cys Gln Val His Gly Asn Tyr Tyr Lys Phe Pro Leu Asp
        2705                2710                2715

Lys Leu Pro Asn Ile Ile Val Ala Leu His Gly Pro Ala Ala Leu
        2720                2725                2730

Arg Val Thr Ala Asp Thr Thr Lys Thr Lys Met Glu Ala Gly Lys
        2735                2740                2745

Val Leu Ser Asp Leu Lys Leu Pro Gly Leu Ala Val His Arg Lys
        2750                2755                2760

Lys Ala Gly Ala Leu Arg Thr Arg Met Leu Arg Ser Arg Gly Trp
        2765                2770                2775

Ala Glu Leu Ala Arg Gly Leu Leu Trp Arg Pro Gly Leu Arg Leu
        2780                2785                2790

Pro Pro Pro Glu Ile Ala Gly Ile Pro Gly Gly Phe Pro Leu Ser
        2795                2800                2805

Pro Pro Tyr Met Gly Val Val His Gln Leu Asp Phe Thr Ser Gln
        2810                2815                2820

Arg Ser Arg Trp Arg Trp Leu Gly Phe Leu Ala Leu Leu Ile Val
        2825                2830                2835

Ala Leu Phe Gly
        2840

<210> SEQ ID NO 4

<211> LENGTH: 1167
<212> TYPE: DNA
<213> ORGANISM: Hepatitis GB Virus C
<220> FEATURE:
<221> NAME/KEY: CDS
<222> LOCATION: (1)..(1167)

<400> SEQUENCE: 4

```
atg gca gtc ctt ctg ctc ctt ctc gtg gtt gag gcc ggg gcc att ctg      48
Met Ala Val Leu Leu Leu Leu Leu Val Val Glu Ala Gly Ala Ile Leu
1               5                   10                  15 gcc ccg gcc acc cac gct tgt cga gcg aat ggg caa tat ttc ctc aca      96
Ala Pro Ala Thr His Ala Cys Arg Ala Asn Gly Gln Tyr Phe Leu Thr
                20                  25                  30 aat tgc tgt gcc ccg gaa gac atc ggg ttc tgc ctg gaa ggc gga tgc     144
Asn Cys Cys Ala Pro Glu Asp Ile Gly Phe Cys Leu Glu Gly Gly Cys
            35                  40                  45 ctg gtg gcc ctg ggg tgc acg gtt tgc acc gac cgt tgc tgg cca ctg     192
Leu Val Ala Leu Gly Cys Thr Val Cys Thr Asp Arg Cys Trp Pro Leu
        50                  55                  60 tat cag gcg ggt ttg gct gtg cgg cct ggc aag tcc gcg gcc cag ctc     240
Tyr Gln Ala Gly Leu Ala Val Arg Pro Gly Lys Ser Ala Ala Gln Leu
65                  70                  75                  80 gtt ggg gaa ctg ggg agc ctg tac ggg ccc ttg tcg gtc tcg gct tac     288
Val Gly Glu Leu Gly Ser Leu Tyr Gly Pro Leu Ser Val Ser Ala Tyr
                85                  90                  95 gta gcc ggg atc ctg ggt ctg ggc gag gtt tac tcc ggg gtc ctg aca     336
Val Ala Gly Ile Leu Gly Leu Gly Glu Val Tyr Ser Gly Val Leu Thr
                100                 105                 110 gtt ggt gtt gcg ttg agg cgc cgg gtc tac ctg atg ccc aac ctg aag     384
Val Gly Val Ala Leu Arg Arg Arg Val Tyr Leu Met Pro Asn Leu Lys
            115                 120                 125 tgt gca gta gaa tgt gac gtt aag tgg gga agt gag ttt tgg aga tgg     432
Cys Ala Val Glu Cys Asp Val Lys Trp Gly Ser Glu Phe Trp Arg Trp
        130                 135                 140 act gag cag ttg gcc tcc aat tac tgg att ttg gaa tac ctt tgg aaa     480
Thr Glu Gln Leu Ala Ser Asn Tyr Trp Ile Leu Glu Tyr Leu Trp Lys
145                 150                 155                 160 gtc cca ttt gaa ttt tgg aga gga gtg atg agc ctg acc cct ctg ttg     528
Val Pro Phe Glu Phe Trp Arg Gly Val Met Ser Leu Thr Pro Leu Leu
                165                 170                 175 gtt tgg gtg gcc gca ttg ctt ttg ctg gag caa cgg att gtc atg gtt     576
Val Trp Val Ala Ala Leu Leu Leu Glu Gln Arg Ile Val Met Val
                180                 185                 190 ttc ctg ctg gtg acg atg gcg ggg atg ttg caa ggc gcc ccc gcc tcc     624
Phe Leu Leu Val Thr Met Ala Gly Met Leu Gln Gly Ala Pro Ala Ser
            195                 200                 205 gtt ttg ggg tcc cgc ccc ttt gac tac ggg ttg aag tgg cag tca tgc     672
Val Leu Gly Ser Arg Pro Phe Asp Tyr Gly Leu Lys Trp Gln Ser Cys
        210                 215                 220 tcc tgc agg gct aac ggg tcg cgt att ccc act ggg gag agg gtg tgg     720
Ser Cys Arg Ala Asn Gly Ser Arg Ile Pro Thr Gly Glu Arg Val Trp
225                 230                 235                 240 gat cga ggg aat gtc acg ctc ttg tgt gac tgc ccc aac ggc ccc tgg     768
Asp Arg Gly Asn Val Thr Leu Leu Cys Asp Cys Pro Asn Gly Pro Trp
                245                 250                 255 gtt tgg gtc ccg gcc ttt tgc cag gcg gtt ggg tgg ggc gac ccc atc     816
Val Trp Val Pro Ala Phe Cys Gln Ala Val Gly Trp Gly Asp Pro Ile
                260                 265                 270 acc cat tgg agc cac gga caa aac cag tgg ccc cta tca tgc ccc caa     864
Thr His Trp Ser His Gly Gln Asn Gln Trp Pro Leu Ser Cys Pro Gln
```

```
                    275                 280                 285
tat gtc tat ggg tct gtg tcc gta acg tgc gtg tgg ggt tcc gtg tct      912
Tyr Val Tyr Gly Ser Val Ser Val Thr Cys Val Trp Gly Ser Val Ser
290                 295                 300 tgg ttt gcc tcg acc ggc ggt cgt gat tcg aag atc gat gtg tgg agt      960
Trp Phe Ala Ser Thr Gly Gly Arg Asp Ser Lys Ile Asp Val Trp Ser
305                 310                 315                 320 ttg gtg ccg gtt gga tct gcc agc tgc acc ata gcc gct cta ggg tca     1008
Leu Val Pro Val Gly Ser Ala Ser Cys Thr Ile Ala Ala Leu Gly Ser
                325                 330                 335 tcg gat cgc gac acg gtg gtt gag ctc tcc gag tgg gga gtc ccg tgc     1056
Ser Asp Arg Asp Thr Val Val Glu Leu Ser Glu Trp Gly Val Pro Cys
            340                 345                 350 gta acg tgt att ctg gac cgt cgg cct gct tca tgt ggc acc tgt gtg     1104
Val Thr Cys Ile Leu Asp Arg Arg Pro Ala Ser Cys Gly Thr Cys Val
        355                 360                 365 cgg gac tgc tgg ccc gaa acc ggg tcg gtt aga ttc cct ttc cat cgg     1152
Arg Asp Cys Trp Pro Glu Thr Gly Ser Val Arg Phe Pro Phe His Arg
370                 375                 380 tgc ggc acg ggg cct                                                 1167
Cys Gly Thr Gly Pro
385

<210> SEQ ID NO 5
<211> LENGTH: 389
<212> TYPE: PRT
<213> ORGANISM: Hepatitis GB Virus C

<400> SEQUENCE: 5

Met Ala Val Leu Leu Leu Leu Val Val Glu Ala Gly Ala Ile Leu
1               5                   10                  15

Ala Pro Ala Thr His Ala Cys Arg Ala Asn Gly Gln Tyr Phe Leu Thr
                20                  25                  30

Asn Cys Cys Ala Pro Glu Asp Ile Gly Phe Cys Leu Glu Gly Gly Cys
            35                  40                  45

Leu Val Ala Leu Gly Cys Thr Val Cys Thr Asp Arg Cys Trp Pro Leu
        50                  55                  60

Tyr Gln Ala Gly Leu Ala Val Arg Pro Gly Lys Ser Ala Ala Gln Leu
65                  70                  75                  80

Val Gly Glu Leu Gly Ser Leu Tyr Gly Pro Leu Ser Val Ser Ala Tyr
                85                  90                  95

Val Ala Gly Ile Leu Gly Leu Gly Glu Val Tyr Ser Gly Val Leu Thr
            100                 105                 110

Val Gly Val Ala Leu Arg Arg Arg Val Tyr Leu Met Pro Asn Leu Lys
        115                 120                 125

Cys Ala Val Glu Cys Asp Val Lys Trp Gly Ser Glu Phe Trp Arg Trp
130                 135                 140

Thr Glu Gln Leu Ala Ser Asn Tyr Trp Ile Leu Glu Tyr Leu Trp Lys
145                 150                 155                 160

Val Pro Phe Glu Phe Trp Arg Gly Val Met Ser Leu Thr Pro Leu Leu
                165                 170                 175

Val Trp Val Ala Ala Leu Leu Leu Leu Glu Gln Arg Ile Val Met Val
            180                 185                 190

Phe Leu Leu Val Thr Met Ala Gly Met Leu Gln Gly Ala Pro Ala Ser
        195                 200                 205

Val Leu Gly Ser Arg Pro Phe Asp Tyr Gly Leu Lys Trp Gln Ser Cys
210                 215                 220
```

-continued

```
Ser Cys Arg Ala Asn Gly Ser Arg Ile Pro Thr Gly Glu Arg Val Trp
225                 230                 235                 240

Asp Arg Gly Asn Val Thr Leu Leu Cys Asp Cys Pro Asn Gly Pro Trp
            245                 250                 255

Val Trp Val Pro Ala Phe Cys Gln Ala Val Gly Trp Gly Asp Pro Ile
        260                 265                 270

Thr His Trp Ser His Gly Gln Asn Gln Trp Pro Leu Ser Cys Pro Gln
    275                 280                 285

Tyr Val Tyr Gly Ser Val Ser Val Thr Cys Val Trp Gly Ser Val Ser
290                 295                 300

Trp Phe Ala Ser Thr Gly Gly Arg Asp Ser Lys Ile Asp Val Trp Ser
305                 310                 315                 320

Leu Val Pro Val Gly Ser Ala Ser Cys Thr Ile Ala Ala Leu Gly Ser
            325                 330                 335

Ser Asp Arg Asp Thr Val Val Glu Leu Ser Glu Trp Gly Val Pro Cys
        340                 345                 350

Val Thr Cys Ile Leu Asp Arg Arg Pro Ala Ser Cys Gly Thr Cys Val
    355                 360                 365

Arg Asp Cys Trp Pro Glu Thr Gly Ser Val Arg Phe Pro Phe His Arg
370                 375                 380

Cys Gly Thr Gly Pro
385

<210> SEQ ID NO 6
<211> LENGTH: 389
<212> TYPE: PRT
<213> ORGANISM: Hepatitis GB virus C

<400> SEQUENCE: 6

Met Ala Val Leu Leu Leu Leu Val Val Glu Ala Gly Ala Ile Leu
1               5                   10                  15

Ala Pro Ala Thr His Ala Cys Arg Ala Asn Gly Gln Tyr Phe Leu Thr
            20                  25                  30

Asn Cys Cys Ala Pro Glu Asp Ile Gly Phe Cys Leu Glu Gly Gly Cys
        35                  40                  45

Leu Val Ala Leu Gly Cys Thr Val Cys Thr Asp Arg Cys Trp Pro Leu
    50                  55                  60

Tyr Gln Ala Gly Leu Ala Val Arg Pro Gly Lys Ser Ala Ala Gln Leu
65                  70                  75                  80

Val Gly Glu Leu Gly Ser Leu Tyr Gly Pro Leu Ser Val Ser Ala Tyr
                85                  90                  95

Val Ala Gly Ile Leu Gly Leu Gly Glu Val Tyr Ser Gly Val Leu Thr
            100                 105                 110

Val Gly Val Ala Leu Arg Arg Val Tyr Leu Met Pro Asn Leu Lys
        115                 120                 125

Cys Ala Val Glu Cys Asp Val Lys Trp Gly Ser Glu Phe Trp Arg Trp
    130                 135                 140

Thr Glu Gln Leu Ala Ser Asn Tyr Trp Ile Leu Glu Tyr Leu Trp Lys
145                 150                 155                 160

Val Pro Phe Glu Phe Trp Arg Gly Val Met Ser Leu Thr Pro Leu Leu
                165                 170                 175

Val Trp Val Ala Ala Leu Leu Leu Glu Gln Arg Ile Val Met Val
            180                 185                 190

Phe Leu Leu Val Thr Met Ala Gly Met Leu Gln Gly Ala Pro Ala Ser
```

-continued

```
                195                 200                 205
Val Leu Gly Ser Arg Pro Phe Asp Tyr Gly Leu Lys Trp Gln Ser Cys
210                 215                 220

Ser Cys Arg Ala Asn Gly Ser Arg Ile Pro Thr Gly Glu Arg Val Trp
225                 230                 235                 240

Asp Arg Gly Asn Val Thr Leu Leu Cys Asp Cys Pro Asn Gly Pro Trp
                245                 250                 255

Val Trp Val Pro Ala Phe Cys Gln Ala Val Gly Trp Gly Asp Pro Ile
                260                 265                 270

Thr His Trp Ser His Gly Gln Asn Gln Trp Pro Leu Ser Cys Pro Gln
                275                 280                 285

Tyr Val Tyr Gly Ser Val Ser Val Thr Cys Val Trp Gly Ser Val Ser
                290                 295                 300

Trp Phe Ala Ser Thr Gly Gly Arg Asp Ser Lys Ile Asp Val Trp Ser
305                 310                 315                 320

Leu Val Pro Val Gly Ser Ala Ser Cys Thr Ile Ala Ala Leu Gly Ser
                325                 330                 335

Ser Asp Arg Asp Thr Val Val Glu Leu Ser Glu Trp Gly Val Pro Cys
                340                 345                 350

Val Thr Cys Ile Leu Asp Arg Pro Ala Ser Cys Gly Thr Cys Val
                355                 360                 365

Arg Asp Cys Trp Pro Glu Thr Gly Ser Val Arg Phe Pro Phe His Arg
370                 375                 380

Cys Gly Thr Gly Pro
385
```

<210> SEQ ID NO 7
<211> LENGTH: 698
<212> TYPE: DNA
<213> ORGANISM: Hepatitis GB Virus C
<220> FEATURE:
<221> NAME/KEY: CDS
<222> LOCATION: (1)..(696)

<400> SEQUENCE: 7

```
gcc ccc gcc tcc gtt ttg ggg tcc cgc ccc ttt gac tac ggg ttg aag        48
Ala Pro Ala Ser Val Leu Gly Ser Arg Pro Phe Asp Tyr Gly Leu Lys
1               5                   10                  15 tgg cag tca tgc tcc tgc agg gct aac ggg tcg cgt att ccc act ggg        96
Trp Gln Ser Cys Ser Cys Arg Ala Asn Gly Ser Arg Ile Pro Thr Gly
                20                  25                  30 gag agg gtg tgg gat cga ggg aat gtc acg ctc ttg tgt gac tgc ccc       144
Glu Arg Val Trp Asp Arg Gly Asn Val Thr Leu Leu Cys Asp Cys Pro
            35                  40                  45 aac ggc ccc tgg gtt tgg gtc ccg gcc ttt tgc cag gcg gtt ggg tgg       192
Asn Gly Pro Trp Val Trp Val Pro Ala Phe Cys Gln Ala Val Gly Trp
        50                  55                  60 ggc gac ccc atc acc cat tgg agc cac gga caa aac cag tgg ccc cta       240
Gly Asp Pro Ile Thr His Trp Ser His Gly Gln Asn Gln Trp Pro Leu
65                  70                  75                  80 tca tgc ccc caa tat gtc tat ggg tct gtg tcc gta acg tgc gtg tgg       288
Ser Cys Pro Gln Tyr Val Tyr Gly Ser Val Ser Val Thr Cys Val Trp
                85                  90                  95 ggt tcc gtg tct tgg ttt gcc tcg acc ggc ggt cgt gat tcg aag atc       336
Gly Ser Val Ser Trp Phe Ala Ser Thr Gly Gly Arg Asp Ser Lys Ile
                100                 105                 110 gat gtg tgg agt ttg gtg ccg gtt gga tct gcc agc tgc acc ata gcc       384
Asp Val Trp Ser Leu Val Pro Val Gly Ser Ala Ser Cys Thr Ile Ala
```

```
            115                 120                 125
gct cta ggg tca tcg gat cgc gac acg gtg gtt gag ctc tcc gag tgg      432
Ala Leu Gly Ser Ser Asp Arg Asp Thr Val Val Glu Leu Ser Glu Trp
130                 135                 140 gga gtc ccg tgc gta acg tgt att ctg gac cgt cgg cct gct tca tgt      480
Gly Val Pro Cys Val Thr Cys Ile Leu Asp Arg Arg Pro Ala Ser Cys
145                 150                 155                 160 ggc acc tgt gtg cgg gac tgc tgg ccc gaa acc ggg tcg gtt aga ttc      528
Gly Thr Cys Val Arg Asp Cys Trp Pro Glu Thr Gly Ser Val Arg Phe
                165                 170                 175 cct ttc cat cgg tgc ggc acg ggg cct cgg ctg aca aag gac ttg gaa      576
Pro Phe His Arg Cys Gly Thr Gly Pro Arg Leu Thr Lys Asp Leu Glu
            180                 185                 190 gct gtg ccc ttc gtc aac agg aca act ccc ttc acc ata agg ggc ccc      624
Ala Val Pro Phe Val Asn Arg Thr Thr Pro Phe Thr Ile Arg Gly Pro
        195                 200                 205 ctg ggc aac cag ggg aga ggc aac ccg gtg cgg tcg ccc ctg ggt ttt      672
Leu Gly Asn Gln Gly Arg Gly Asn Pro Val Arg Ser Pro Leu Gly Phe
210                 215                 220 ggg tcc tac acc atg acc aag atc cg                                   698
Gly Ser Tyr Thr Met Thr Lys Ile
225                 230

<210> SEQ ID NO 8
<211> LENGTH: 232
<212> TYPE: PRT
<213> ORGANISM: Hepatitis GB Virus C

<400> SEQUENCE: 8

Ala Pro Ala Ser Val Leu Gly Ser Arg Pro Phe Asp Tyr Gly Leu Lys
1               5                   10                  15

Trp Gln Ser Cys Ser Cys Arg Ala Asn Gly Ser Arg Ile Pro Thr Gly
            20                  25                  30

Glu Arg Val Trp Asp Arg Gly Asn Val Thr Leu Leu Cys Asp Cys Pro
        35                  40                  45

Asn Gly Pro Trp Val Trp Val Pro Ala Phe Cys Gln Ala Val Gly Trp
    50                  55                  60

Gly Asp Pro Ile Thr His Trp Ser His Gly Gln Asn Gln Trp Pro Leu
65                  70                  75                  80

Ser Cys Pro Gln Tyr Val Tyr Gly Ser Val Ser Val Thr Cys Val Trp
                85                  90                  95

Gly Ser Val Ser Trp Phe Ala Ser Thr Gly Gly Arg Asp Ser Lys Ile
            100                 105                 110

Asp Val Trp Ser Leu Val Pro Val Gly Ser Ala Ser Cys Thr Ile Ala
        115                 120                 125

Ala Leu Gly Ser Ser Asp Arg Asp Thr Val Val Glu Leu Ser Glu Trp
    130                 135                 140

Gly Val Pro Cys Val Thr Cys Ile Leu Asp Arg Arg Pro Ala Ser Cys
145                 150                 155                 160

Gly Thr Cys Val Arg Asp Cys Trp Pro Glu Thr Gly Ser Val Arg Phe
                165                 170                 175

Pro Phe His Arg Cys Gly Thr Gly Pro Arg Leu Thr Lys Asp Leu Glu
            180                 185                 190

Ala Val Pro Phe Val Asn Arg Thr Thr Pro Phe Thr Ile Arg Gly Pro
        195                 200                 205

Leu Gly Asn Gln Gly Arg Gly Asn Pro Val Arg Ser Pro Leu Gly Phe
    210                 215                 220
```

```
Gly Ser Tyr Thr Met Thr Lys Ile
225                 230

<210> SEQ ID NO 9
<211> LENGTH: 232
<212> TYPE: PRT
<213> ORGANISM: Hepatitis GB virus C

<400> SEQUENCE: 9

Ala Pro Ala Ser Val Leu Gly Ser Arg Pro Phe Asp Tyr Gly Leu Lys
1               5                   10                  15

Trp Gln Ser Cys Ser Cys Arg Ala Asn Gly Ser Arg Ile Pro Thr Gly
            20                  25                  30

Glu Arg Val Trp Asp Arg Gly Asn Val Thr Leu Leu Cys Asp Cys Pro
        35                  40                  45

Asn Gly Pro Trp Val Trp Val Pro Ala Phe Cys Gln Ala Val Gly Trp
    50                  55                  60

Gly Asp Pro Ile Thr His Trp Ser His Gly Gln Asn Gln Trp Pro Leu
65                  70                  75                  80

Ser Cys Pro Gln Tyr Val Tyr Gly Ser Val Ser Val Thr Cys Val Trp
                85                  90                  95

Gly Ser Val Ser Trp Phe Ala Ser Thr Gly Gly Arg Asp Ser Lys Ile
            100                 105                 110

Asp Val Trp Ser Leu Val Pro Val Gly Ser Ala Ser Cys Thr Ile Ala
        115                 120                 125

Ala Leu Gly Ser Ser Asp Arg Asp Thr Val Val Glu Leu Ser Glu Trp
    130                 135                 140

Gly Val Pro Cys Val Thr Cys Ile Leu Asp Arg Arg Pro Ala Ser Cys
145                 150                 155                 160

Gly Thr Cys Val Arg Asp Cys Trp Pro Glu Thr Gly Ser Val Arg Phe
                165                 170                 175

Pro Phe His Arg Cys Gly Thr Gly Pro Arg Leu Thr Lys Asp Leu Glu
            180                 185                 190

Ala Val Pro Phe Val Asn Arg Thr Thr Pro Phe Thr Ile Arg Gly Pro
        195                 200                 205

Leu Gly Asn Gln Gly Arg Gly Asn Pro Val Arg Ser Pro Leu Gly Phe
    210                 215                 220

Gly Ser Tyr Thr Met Thr Lys Ile
225                 230

<210> SEQ ID NO 10
<211> LENGTH: 199
<212> TYPE: DNA
<213> ORGANISM: Hepatitis GB Virus C
<220> FEATURE:
<221> NAME/KEY: CDS
<222> LOCATION: (1)..(198)

<400> SEQUENCE: 10 gag agg gtg tgg gat cga ggg aat gtc acg ctc ttg tgt gac tgc ccc      48
Glu Arg Val Trp Asp Arg Gly Asn Val Thr Leu Leu Cys Asp Cys Pro
1               5                   10                  15 aac ggc ccc tgg gtt tgg gtc ccg gcc ttt tgc cag gcg gtt ggg tgg      96
Asn Gly Pro Trp Val Trp Val Pro Ala Phe Cys Gln Ala Val Gly Trp
            20                  25                  30 ggc gac ccc atc acc cat tgg agc cac gga caa aac cag tgg ccc cta     144
Gly Asp Pro Ile Thr His Trp Ser His Gly Gln Asn Gln Trp Pro Leu
        35                  40                  45
```

```
tca tgc ccc caa tat gtc tat ggg tct gtg tcc gta acg tgc gtg tgg    192
Ser Cys Pro Gln Tyr Val Tyr Gly Ser Val Ser Val Thr Cys Val Trp
    50                  55                  60 ggt tcc g                                                           199
Gly Ser
65
```

<210> SEQ ID NO 11
<211> LENGTH: 66
<212> TYPE: PRT
<213> ORGANISM: Hepatitis GB Virus C

<400> SEQUENCE: 11

```
Glu Arg Val Trp Asp Arg Gly Asn Val Thr Leu Leu Cys Asp Cys Pro
1               5                   10                  15

Asn Gly Pro Trp Val Trp Val Pro Ala Phe Cys Gln Ala Val Gly Trp
            20                  25                  30

Gly Asp Pro Ile Thr His Trp Ser His Gly Gln Asn Gln Trp Pro Leu
        35                  40                  45

Ser Cys Pro Gln Tyr Val Tyr Gly Ser Val Ser Val Thr Cys Val Trp
    50                  55                  60

Gly Ser
65
```

<210> SEQ ID NO 12
<211> LENGTH: 66
<212> TYPE: PRT
<213> ORGANISM: Hepatitis GB virus C

<400> SEQUENCE: 12

```
Glu Arg Val Trp Asp Arg Gly Asn Val Thr Leu Leu Cys Asp Cys Pro
1               5                   10                  15

Asn Gly Pro Trp Val Trp Val Pro Ala Phe Cys Gln Ala Val Gly Trp
            20                  25                  30

Gly Asp Pro Ile Thr His Trp Ser His Gly Gln Asn Gln Trp Pro Leu
        35                  40                  45

Ser Cys Pro Gln Tyr Val Tyr Gly Ser Val Ser Val Thr Cys Val Trp
    50                  55                  60

Gly Ser
65
```

<210> SEQ ID NO 13
<211> LENGTH: 13
<212> TYPE: PRT
<213> ORGANISM: Hepatitis GB virus C

<400> SEQUENCE: 13

```
Val Tyr Gly Ser Val Ser Val Thr Cys Val Trp Gly Ser
1               5                   10
```

<210> SEQ ID NO 14
<211> LENGTH: 9
<212> TYPE: PRT
<213> ORGANISM: Hepatitis GB virus C

<400> SEQUENCE: 14

```
Pro Gln Tyr Val Tyr Gly Ser Val Ser
1               5
```

<210> SEQ ID NO 15

-continued

```
<211> LENGTH: 6
<212> TYPE: PRT
<213> ORGANISM: Hepatitis GB virus C

<400> SEQUENCE: 15

Val Tyr Gly Ser Val Ser
1               5

<210> SEQ ID NO 16
<211> LENGTH: 10
<212> TYPE: PRT
<213> ORGANISM: Hepatitis GB virus C

<400> SEQUENCE: 16

Gln Tyr Val Tyr Gly Ser Val Ser Val Thr
1               5                   10

<210> SEQ ID NO 17
<211> LENGTH: 14
<212> TYPE: PRT
<213> ORGANISM: Hepatitis GB virus C

<400> SEQUENCE: 17

Gly Gly Gly Gly Gly Arg Lys Lys Arg Arg Gln Arg Arg Arg
1               5                   10

<210> SEQ ID NO 18
<211> LENGTH: 27
<212> TYPE: PRT
<213> ORGANISM: Hepatitis GB virus C

<400> SEQUENCE: 18

Gly Gly Gly Gly Gly Arg Lys Lys Arg Arg Gln Arg Arg Arg Val Tyr
1               5                   10                  15

Gly Ser Val Ser Val Thr Cys Val Trp Gly Ser
            20                  25

<210> SEQ ID NO 19
<211> LENGTH: 27
<212> TYPE: PRT
<213> ORGANISM: Hepatitis GB virus C

<400> SEQUENCE: 19

Gly Gly Gly Gly Gly Arg Lys Lys Arg Arg Gln Arg Arg Arg Val His
1               5                   10                  15

Gly Ser Val Ser Val Thr Cys Val Trp Gly Ser
            20                  25

<210> SEQ ID NO 20
<211> LENGTH: 17
<212> TYPE: PRT
<213> ORGANISM: Hepatitis GB virus C

<400> SEQUENCE: 20

Gly Gly Ala Gly Leu Thr Gly Gly Arg Tyr Glu Pro Leu Val Arg Arg
1               5                   10                  15

Cys

<210> SEQ ID NO 21
<211> LENGTH: 17
<212> TYPE: PRT
<213> ORGANISM: Hepatitis GB virus C

<400> SEQUENCE: 21
```

```
Gly Cys Arg Cys Ala Arg Gly Val Leu Leu Thr Pro Gly Glu Gly Tyr
1               5                   10                  15
Phe
```

GB VIRUS C (HEPATITIS G VIRUS) E2 GLYCOPROTEIN AS AN IMMUNOMODULATORY AGENT

RELATED APPLICATIONS

This application is a national phase application under 35 U.S.C. §371 of International Application Number PCT/US2013/030665, filed Mar. 13, 2013, which claims priority to U.S. Provisional Patent Application Ser. No. 61/613,298, filed Mar. 20, 2012. The entire contents of the above-referenced disclosures are specifically incorporated herein by reference.

This invention was made with government support under Grant No. RO1 AI-58740 awarded by the National Institutes of Allergy and Infectious Disease and Merit Review Grant I01BX000207 awarded by the Department of Veterans Affairs. The Government has certain rights in the invention.

BACKGROUND OF THE INVENTION

The sequence listing that is contained in the file named "IOWAP0113US_ST25.txt", which is 117 KB (as measured in Microsoft Windows®) and was created on Sep. 11, 2014, is filed herewith by electronic submission and is incorporated by reference herein.

I. Field of the Invention

The present invention relates generally to the fields of molecular biology and virology. More particularly, it concerns methods and compositions to treat inflammatory conditions, in particular those resulting from pathologic T-cell activation.

II. Description of Related Art

GB virus C (GBV-C) is a human virus of Flaviviridae family that is most closely related to hepatitis C virus (HCV) (reviewed in Stapleton et al., 2011; Mohr and Stapleton, 2009; Stapleton, 2003). GBV-C infection is common, and about 1% to 4% of US blood donors are viremic at the time of donation. Due to shared route of transmission, the virus is highly prevalent among HIV-infected individuals (up to 42%) (Stapleton et al., 2011; Mohr and Stapleton, 2009; Rey et al., 2000). GBV-C infection is not clearly associated with any disease; however, several studies found an association between persistent GBV-C infection and prolonged survival in HIV-positive individuals (Williams et al., 2004; Nunnari et al., 2003; Xiang et al., 2001; Tillmann et al., 2001; Yeo et al., 2000; Lefrere et al., 1999; Toyoda et al., 1998; Heringlake et al., 1998). GBV-C is lymphotropic, and GBV-C infection modulates multiple host factors that play a critical role in HIV infection including the expression of cytokines, chemokines and their receptors (reviewed in Bhattarai and Stapleton, 2012). The alteration of host factors involved in HIV replication by GBV-C could limit HIV infection and contribute to the protective effect of GBV-C coinfection observed in HIV-positive individuals.

Chronic HIV infection is characterized by persistent immune activation which contributes to T cell depletion, altered cytokine expression and loss of T cell function (reviewed in Pett, 2009; Abrams et al., 2009; Sodora and Silvestri, 2008). Interleukin-2 (IL-2) is a critical cytokine required for T cell activation, proliferation, and function (reviewed in Pett et al., 2010; Nel, 2002). However, IL-2 also induces secretion of proinflammatory cytokines like IL-6, IL-β and tumor necrosis factor alpha (TNF-α) (Fortis et al., 2002; Sereti et al., 2001; Heaton et al., 1993), and is associated with increased levels of inflammatory markers like C-reactive protein (CRP) and D-dimer in the plasma of HIV-infected subjects independent of HIV viral load (Porter et al., 2009). In addition, in vitro activation of peripheral blood mononuclear cells (PBMCs) with IL-2 increases HIV production (Kinter et al., 1995; Morgan et al., 1976). Thus, IL-2 may also promote HIV replication and contribute to HIV associated immune activation Immune activation not only supports HIV replication but it is suggested to be a better predictor of HIV disease progression than plasma HIV viral load (VL) (Giorgi et al., 1999; Hazenberg et al., 2003).

In studies of HIV-infected people, GBV-C viremia is associated with lower surface expression of T cell activation markers compared to GBV-C non-viremic controls independent of HIV VL (Maidana-Giret et al., 2009; Schwarze-Zander et al., 2010; Nattermann et al., 2003). Surface expression of T cell activation markers CD38 and/or CCR5 were significantly lower in CD4+ and CD8+ T cells from GBV-C viremic subjects compared to non-viremic controls. Among HIV-infected subjects receiving intravenous IL-2, GBV-C viremic subjects had significantly reduced CD4+ T cell expansion compared GBV-C non-viremic controls (Stapleton et al., 2009) suggesting GBV-C infection may alter T cell activation and IL-2 signaling pathways. In addition, GBV-C produced by peripheral blood mononuclear cells (PBMCs) in vitro was significantly reduced following activation with IL-2 and phytohemagglutinin (PHA) (George et al., 2006) further suggesting an interaction between GBV-C and IL-2. Since IL-2 plays a critical role in HIV infection and disease progression, the effects of GBV-C on IL-2 may contribute to the protective effect of GBV-C coinfection in HIV infected individuals. Previous studies demonstrated that addition of the GBV-C envelope glycoprotein (E2) inhibits HIV replication when added to cells (Mohr and Stapleton, 2009; Koedel et al., 2011; Jung et al., 2007), or when expressed in a CD4+ T cell line (Xiang et al., 2006). However, the full impact of these interactions on immune signaling is not understood.

SUMMARY OF THE INVENTION

Thus, in accordance with the present invention, there is provided a method a method of inhibiting immune cell activation comprising administering to a mammalian subject in need thereof a GBV-C E2 peptide or polypeptide comprising 10 contiguous residues of the GBV-C2 E2 protein including Tyrosine 87. The subject may suffer from a T cell- or B-cell-mediated inflammatory disease or an IL-2-mediated inflammatory disease.

The peptide or polypeptide may comprise 11, 12, 13, 14, 15, 16, 17, 18, 19, 20, 21, 22, 23, 24, 25, 30, 35, 40, 45, 50, 75, 100, 150, 175, 200, 219, 250 consecutive residues of GBV-C E2 or full length GBV-C E2. The peptide or polypeptide may be about 16, 17, 18, 19, 20, 21, 22, 23, 24, 25, 30, 35, 40, 45, 50, 75, 100, 125, 150, 175, 200, 219 or 250 residues in length. The peptide may comprise the sequence VYGSVSVTCVWGS (SEQ ID NO: 9), PQYVYGSVS (SEQ ID NO: 10) VYGSVS (SEQ ID NO: 11) or QYVYGS-VSVT (SEQ ID NO: 12). The peptide or polypeptide may comprise a non-GBV-C E2 sequence, such as a cell permeability peptide, such as HIV TAT. The GBV-C E2 sequences may be SEQ ID NOS: 5, 6 or 8. The peptide or polypeptide may comprises all L amino acids, all D amino acids, or a mix of L and D amino acids.

The immune cell may be a T cell, a B cell, such as a helper T cell suppressor T cell, or a killer T cell or NK cell. The subject may a human. Administering comprises intravenous, intra-arterial, oral, subcutaneous, topical or intraperitoneal administration. The method may further comprising administering a second anti-inflammatory agent, such as a steroid or a COX-2 inhibitor. The second anti-inflammatory agent may be contacted prior to said peptide or polypeptide, or after said peptide or polypeptide or even contacted at the same time as said peptide or polypeptide. The peptide or polypeptide may be administered at 0.1-500 mg/kg/d, may be administered daily or weekly, or may be administered daily for 7 days, 2 weeks, 3 weeks, 4 weeks, one month, 6 weeks, 8 weeks, two months, 12 weeks, or 3 months, or weekly for 2 weeks, 3 weeks, 4 weeks, 6 weeks, 8 weeks, 10 weeks, or 12 weeks.

In another embodiment, there is provided a method of inhibiting IL-2 release in a mammalian subject comprising administering to said subject a GBV-C E2 peptide or comprising 10 contiguous residues of the GBV-C2 E2 protein including Tyr87. The method may result in reduced or inhibited CD25 expression or levels.

In yet another embodiment, there is provided a method of inhibiting inflammation in a mammalian subject comprising administering to said subject a GBV-C E2 peptide or polypeptide comprising 10 contiguous residues of the GBV-C2 E2 protein including Tyr87. The peptide or polypeptide may comprise about 16, 17, 18, 19, 20, 21, 22, 23, 24, 25, 30, 35, 40, 45, 50, 75, 100, 150, 175, 200, 219, 250 consecutive residues of GBV-C E2 or full length GBV-C E2.

An even further embodiment comprises a method of inhibiting STAT5-mediated signaling in a mammalian subject comprising administering to said subject a GBV-C E2 peptide or polypeptide comprising 10 contiguous residues of the GBV-C2 E2 protein including Tyr87. The peptide or polypeptide may comprise about 16, 17, 18, 19, 20, 21, 22, 23, 24, 25, 30, 35, 40, 45, 50, 75, 100, 150, 175, 200, 219, 250 consecutive residues of GBV-C E2 or full length GBV-C E2.

In still a further embodiment, there is provided an isolated peptide comprising 10 contiguous residues of the GBV-C2 E2 protein including Tyr87. The peptide may comprise about 11, 12, 13, 14, 15, 16, 17, 18, 19, 20, 21, 22, 23, 24, 25, 30, 35, 40, 45, or 50 consecutive residues of GBV-C E2. The peptide may be about 11, 12, 13, 14, 15, 16, 17, 18, 19, 20, 21, 22, 23, 24, 25, 30, 35, 40, 45, 50, 75, or 100 residues in length. The the peptide may comprise SEQ ID NOS: 5, 6 or 8, or the sequence VYGSVSVTCVWGS (SEQ ID NO: 9), PQYVYGSVS (SEQ ID NO: 10) VYGSVS (SEQ ID NO: 11) or QYVYGSVSVT (SEQ ID NO: 12). The peptide may be formulated for pharmaceutical administration, such as topical, cutaneous, subcutaneous, alimentrary or parenteral administration.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are cited, it is understood that the steps are not required to be performed in the particular order recited unless one of skill in the art is not be able to practice the method in a different order.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C. Summary of GBV-C E2 proteins stably expressed in Jurkat CD4+ T cells. Schematic of GBV-C envelope protein E2 (nt 1167-2161; 331aa), E2 deletion mutants, N terminal 219 amino acids (nt 1167-1824) and C terminal 112 amino acids (nt 1824-2161) and frame-shift control (FS) (FIG. 1A). Boxes indicate cell lines in which IL-2 release was not inhibited (white) or inhibited (shaded) compared to the vector control following TCR engagement. GFP expression in cell lines expressing GBV-C E2 protein, deletion mutants (E2 1-219; E2 219-331), frame shift (FS) control or empty vector (VC) (FIG. 1B). E2 protein expression detected in Jurkat cell lysates with tetra-his antibody directed to C-terminal his-tag fused with E2 protein (FIG. 1C).

FIGS. 2A-B. GBV-C E2 protein inhibits TCR-induced IL-2 in Jurkat CD4+ T cells. Following TCR engagement IL-2 secretion was significantly inhibited in Jurkat cells expressing GBV-C E2 protein and N terminal 219 amino acids compared to the vector control. Expression of GBV-C E2 RNA (FS) or C terminal 112 amino acids did not alter IL-2 synthesis (FIG. 2A). IL-2 transcription was significantly inhibited by GBV-C E2 protein expression and culturing E2 expressing Jurkat cells in doxycycline rescued the inhibitory effect of GBV-C E2 protein on IL-2 transcription (FIG. 2B). *$P<0.05$; **$P<0.01$.

FIGS. 3A-C. GBV-C E2 protein alters IL-2 signaling pathways. GBV-C E2 protein expression reduced CD25 expression in Jurkat cells which was rescued by culturing cells in doxycycline. Following activation with anti-CD3/CD28, CD25 expression was significantly lower in E2 expressing Jurkat cells compared to the control cells or E2 expressing cells cultured in doxycycline (FIG. 3A). CD25 transcription was significantly inhibited by GBV-C E2 protein expression compared to control cells and E2 expressing Jurkat cells cultured in doxycycline (FIG. 3B). Following stimulation with IL-2 for 15 minutes STAT5 phosphorylation was inhibited Jurkat cells expressing GBV-C E2 protein compared to frame shift (FS) control cells. Total STAT5 expression was not altered by GBV-C E2 protein expression (FIG. 3C). *$P<0.05$; ***$P<0.001$.

FIGS. 4A-B. GBV-C E2 protein expression inhibits proliferation of Jurkat cells following TCR activation. At baseline (day 0), there was no significant difference in percentage of cells stained with proliferation dye eFlour450. Following activation with anti-CD3/CD25 for five days proliferation was significantly reduced in Jurkat cells expressing GBV-C E2 protein compared to the frame shift control (FS) (FIG. 4A). Cell proliferation was significantly reduced in Jurkat cells expressing GBV-C E2 protein during five days of anti-CD3/CD28 stimulation (FIG. 4B). *$P<0.05$.

FIGS. 5A-C. GBV-C E2 protein inhibits IL-2 secretion from PBMCs and CD25 expression on primary CD4+ and CD8+ T cells. SDS-PAGE and immunoblot analysis of purified recombinant GBV-C E2 protein fused to human IgG Fc (FIG. 5A). Following stimulation with anti-CD3/CD28, IL-2 secretion by PBMCs (FIG. 5B) and CD25 expression on CD4+ and CD8+ T cells (FIG. 5C) were significantly reduced in PBMCs from healthy donors (n=4) incubated with GBV-C E2 compared to the human IgG control following stimulation with anti-CD3/CD28. P<0.01; *P<0.001.

FIGS. 6A-B. GBV-C E2 expression inhibits T cell activation. Jurkat (CD4+) cells expressing GBV-C E2 or the GBV-C RNA with a frameshift introduced to abolish translation (FS) were stimulated with anti-CD3/CD28. (FIG. 6A) Surface expression of the activation marker CD69 measured 24 hrs post-activation. (FIG. 6B) The reduction in activation was reversed by growing E2 expressing cells in doxycycline (Tet-Off cells). * p<0.001.

FIG. 13C) and zeta-chain-associated protein kinase (ZAP)-70 (FIG. 13D) compared to the frameshift control (FS). MFI=mean fluorescence intensity. Each experiment was repeated at least three times with consistent results. *P<0.05; **P<0.001

(FIG. 17C) was inhibited in Jurkat cells (JC; GFP-negative) co-cultured with GBV-C E2 expressing cells (GFP-positive) compared to Jurkat cells (JC; GFP-negative) co-cultured with vector control cells (VC; GFP-positive). Detection of GBV-C E2 protein and CD63 (a marker for microvesicles of endocytic origin) in extracellular microvesicles (EMV) purified from the clarified supernatant of Jurkat cells expressing GBV-C E2 protein or control cells containing the GBV-C E2 coding region with a frameshift to abolish translation (FS) (FIG. 17D). Following stimulation with anti-CD3/CD28 antibodies, IL-2 release (FIG. 17E), CD69 and CD25 cell surface expression (FIGS. 17F-G) was significantly inhibited in PBMCs from healthy donor incubated with GBV-C E2-positive secreted microvesicles (E2 EMV) compared to E2-negative microvesicles (FS EMV). -Fold change was calculated by measuring IL-2, CD69 and CD25 levels before and after stimulation. US=unstimulated, MFI=mean fluorescence intensity. Data represent the average of three independent cultures. *P<0.01, **P<0.01.

FIGS. 19A-B. GBV-C E2 protein expression reduces LAT and ZAP-70 phosphorylation. Phosphorylation of LAT (Y191) was significantly inhibited following TCR activation in Jurkat cells expressing GBV-C E2 protein compared to the frameshift control (FS) as determined by ELISA (FIG. 19A). -Fold change in phosphorylation of ZAP-70 (Y319) following TCR activation (FIG. 19B). ELISA data represent the average LAT phosphorylation from three independent cultures. Each experiment was repeated at least three times with consistent results. *P<0.05; **P<0.01.

FIGS. 20A-C. GBV-C E2 protein does not alter CD45 and Csk expression. Expression of CD45 (FIG. 20A) and Csk (FIG. 20C) was not different in GBV-C E2 expressing cells compared to the FS control. Recombinant GBV-C E2 protein did not affect CD45 enzymatic function (FIG. 20B). NS=not significant.

FIGS. 22A-D. Sequence alignment of E2 protein from human and chimpanzee GBV-C isolates. GBV-C E2 protein sequence from human GBV-C (GBV-$C_{hum}$) and chimpanzee GBV-C (GBV-$C_{cpz}$) representing two predicted Lck substrate motifs (aa 83-91) (FIG. 22A) and (aa 281-289) (FIG. 22B), and two SH3 binding motifs (aa 48-51) (FIG. 22C) and (aa 257-260) (FIG. 22D).

FIGS. 24A-D. Uptake of TAT-fused peptides in PBMCs. Cellular uptake of FITC labelled TAT-fused synthetic GBV-C E2 peptides representing (86-98) aa region (FIGS. 24C-D) and TAT-only control peptide (FIG. 24B) or no peptide (FIG. 24A) by PBMCs after 24 hours as determined by flow cytometry.

FIGS. 25A-C. Proposed model for inhibition of T cell receptor (TCR) signaling in infected and bystander T cells during GBV-C infection. GBV-C infection of T cells results into exposure to envelope protein E2 which competes for Lck and inhibits Lck function in the infected T cells (FIG. 25A). GBV-C infected T cells secrets GBV-C E2 proteins and RNA in microvesicles along with virus particles. Newly released virus particles can infect and inhibit TCR signaling in permissive T cells by inhibiting Lck (FIG. 26B). In addition, E2-containing extracellular microvesicles are taken up by bystander non-infected T cells where E2 can compete for Lck and inhibit Lck activation (FIG. 25C).

DESCRIPTION OF ILLUSTRATIVE EMBODIMENTS

Persistent immune activation and immune dysfunction are characteristic features of chronic HIV infection and contribute to HIV-mediated immunodeficiency (reviewed in Pett, 2009; Sodora and Silvestri, 2008). GBV-C viremia is associated with reduced T cell activation markers on CD4+ and CD8+ T cells in HIV-infected subjects compared to controls without GBV-C viremia, independent of HIV viral load (Maidana-Giret et al., 2009). HIV-positive individuals with GBV-C viremia had reduced expression of T cell activation markers compared to non-viremic controls, suggesting that GBV-C may modulate T cell activation responses (Maidana-Giret et al., 2009; Schwarze-Zander et al., 2010; Nattermann et al., 2003). IL-2 is a critical cytokine which regulates T cell activation and proliferation (reviewed in Pett, 2009; Pett et al., 2010), and previous studies suggested an interaction between GBV-C and IL-2 in vitro and in vivo (Stapleton et al., 2009; George et al., 2003). Thus, GBV-C effects on T cell activation may be mediated in part by altering IL-2 expression.

In this study, the inventors found that the GBV-C envelope protein E2 expression significantly inhibited IL-2 production following TCR engagement (FIG. 2A) by reducing IL-2 transcription (FIG. 2B). The region within the E2 protein required to alter IL-2 expression resided in the N terminal 219 amino acids (aa), as the expression of amino acids 219 to 331 of the GBV-C E2 protein did not affect IL-2 release (FIG. 2C). In addition, since proximal TCR signaling contributes to IL-2 transcription (reviewed in Nel, 2002), studies into the effects of GBV-C infection and GBV-C E2 protein on TCR signaling appear warranted. The GBV-C effects on IL-2 observed in this study may contribute to lower immune activation in HIV-positive individuals and limit HIV mediated immunopathogenesis.

Figure 3C:
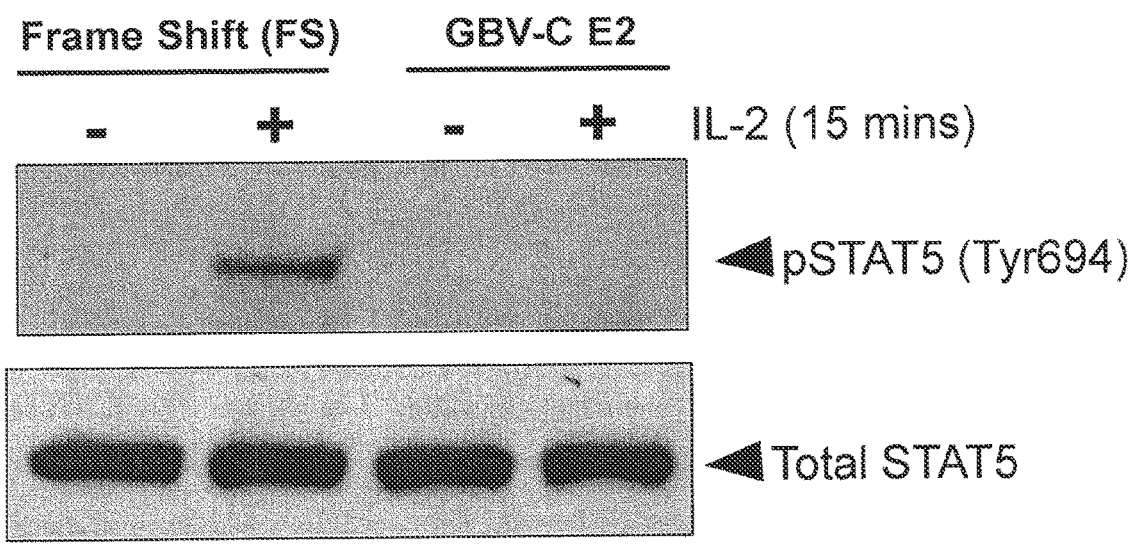

GBV-C viremic HIV-positive subjects had significantly reduced CD4+ T cell expansion following intravenous IL-2 therapy compared to GBV-C non-viremic controls (Stapleton et al., 2009) suggesting GBV-C may alter IL-2 signaling pathways. IL-2 signaling is initiated upon binding to the high affinity IL-2 receptor (IL-2R), as noted above (reviewed in (Cheng et al., 2011). CD25 expression is upregulated upon activation, promoting IL-2 mediated T cell activation and proliferation. Expression of CD25 on Jurkat cell was impaired by GBV-C E2 protein expression and was significantly reduced following activation compared to the FS controls. Furthermore, this was due to E2 expression, as CD25 expression increased in the E2 expressing, Tet-off Jurkat cells maintained in doxycycline (FIG. 3A). The effect of GBV-C E2 protein on CD25 was mediated in part by reducing CD25 transcription (FIG. 3B). STAT5 phosphorylation was inhibited in GBV-C E2 expressing Jurkat cells following stimulation with IL-2 (FIG. 3C) suggesting a significant alteration of IL-2 signaling pathway. Consistent with these data, GBV-C/HIV viremic subjects had reduced CD25 expression on CD4+ and CD8+ T cells compared to HIV mono-infected subjects (Maidana-Giret et al., 2009).

The reduction in IL-2 and CD25 transcription reduced both IL-2 signaling (FIG. 3C) and cellular proliferation (FIG. 4), providing an explanation for why GBV-C infection is associated with reduced CD4+ T cell expansion following IL-2 therapy in HIV-positive subjects (Stapleton et al., 2009). Consistent with the Jurkat cell data, incubation of PBMCs from healthy subjects with recombinant GBV-C E2 protein stimulated with anti-CD3/CD28 demonstrated a reduction in IL-2 secretion and CD25 expression on both CD4+ and CD8+ T cells compared to control PBMCs (FIGS. 5B-C).

These data support in vivo findings that GBV-C viremia modulates T cell activation, IL-2 mediated proliferation (Maidana-Giret et al., 2009; Stapleton et al., 2009) and suggest that the effect is mediated at least in part by the viral envelope glycoprotein E2. Previous studies found that GBV-C E2 protein inhibits HIV replication at the entry step, and recently this was mapped to amino acids 276-292 on the GBV-C E2 protein (Mohr and Stapleton, 2009; Jung et al., 2007; Xiang et al., 2006). The GBV-C E2 region required for downregulation of IL-2 mRNA and IL-2 release appears to be distinct from that involved in HIV inhibition as the E2 region from 1-219 did not inhibit HIV (Xiang et al., 2006) and expression of GBV-C E2 amino acids 219-331 did not alter IL-2 release, while expression of amino acids 1-219 of E2 blocked IL-2 release, transcription and CD25 upregulation in response to T cell activation. Thus, different regions of the GBV-C E2 protein have distinct functional roles in the interaction between HIV inhibition and modulation of T cell activation and proliferation. The effects of GBV-C E2 protein on IL-2 signaling pathways may contribute to the reduction in HIV-associated immune activation observed in GBV-C/HIV coinfected individuals, and may also play an important role in regulating other immune cell function including regulatory T cells (Tregs), B cells, natural killer (NK) cells, macrophages, monocytes and dendritic cells, all of which are important in maintaining immune homeostasis (Morgan et al., 1976; Kim et al., 2006; Green et al., 2003).

The present invention, therefore, seeks to exploit this newly identified function of GBV-C E2 to modulate a variety of immune cells in pathologic settings. In particular, the inventors contemplate the treatment of hyperinflammatory conditions, including those linked to IL-2 release. These and other aspects of the invention are discussed in detail below.

I. GBV-C VIRUS

Like other members of the Flaviviridae, GBV-C is a positive-strand RNA virus that encodes a single long open reading frame (Leary et al., 1996). GBV-C does not cause acute or chronic hepatitis, yet it is the family member most closely related to HCV, the cause of hepatitis C. Sequences of GBV-C have been previously reported, for example in U.S. Pat. No. 5,874,563, which is specifically incorporated by reference. In particular, an infectious GBV-C clone has been described in the PCT application WO 01/77157, which is incorporated herein by reference.

The GBV-C polyprotein is predicted to be cleaved into two envelope proteins (E1 and E2, referred to collectively as GBV-C envelope protein), an RNA helicase, a trypsin-like serine protease, and an RNA-dependent RNA polymerase. A major difference between GBV-C and HCV is in the amino terminus of the polyprotein. In many isolates, this region is truncated, and no core (or nucleocapsid) protein is present (Simons et al., 1995; Xiang et al., 1999). In vitro translation experiments suggest that the AUG immediately upstream of the putative E1 protein is preferentially used to initiate translation, although there may be as many as four AUG's in frame with the polyprotein upstream of this AUG (Simons et al., 1996).

The site of GBV-C replication has not been clearly identified, but it appears that replication in the hepatocyte, if it occurs, is not the primary source of virus in infected individuals (Laskus et al., 1998; Pessoa et al., 1998; Seipp et al., 1999). Recently, there were reports that human peripheral blood mononuclear cells (PBMC's) and interferon-resistant Daudi cells are permissive for GBV-C replication (Fogeda et al., 1999; Shimizu, 1999). In addition, transient replication of GBV-C was described in MT-2 cells (a human T-cell line), and PHSCH (a human hepatocyte line immortalized with simian virus 40 large T antigen) (Seipp et al., 1999).

II. GBV-C E2 POLYPEPTIDES

In certain aspects, the invention is directed to the GBV-C virus E2 protein. The expression or provision of GBV-C E2 peptides and polypeptides can be used to modulate immune function. SEQ ID NO: 2 and 3 represent the translated product of SEQ ID NO:1 (GBV-C polyprotein) and 4 (GBV-C E2 protein), respectively. It is contemplated that the compositions and methods disclosed herein may be utilized to express all or part of SEQ ID NO: 3 and derivates thereof. In certain embodiments, compositions of the invention may include the peptides as set forth in SEQ ID NOs: 5, 6 or 8. Other peptides include the sequence VYGSVSVTCVWGS (SEQ ID NO: 9), PQYVYGSVS (SEQ ID NO: 10) VYGSVS (SEQ ID NO: 11) or QYVYGSVSVT (SEQ ID NO: 12).

The method of claim 1, wherein said peptide comprises about 10, 11, 12, 13, 14, 15, 16, 17, 18, 19, 20, 21, 22, 23, 24, 25, 30, 35, 40, 45, 50, 75, 100, 150, 175, 200, 219, 250 consecutive residues of GBV-C E2 or full length GBV-C E2. Determination of which peptides possess activity may be achieved using functional assays measuring T-cell activation and proliferation as well as cytokine productiOn, which are familiar to those of skill in the art.

In certain embodiments, the GBV-C E2 peptide comprises at least about 15 residues of the N-terminal 100 residues of full-length GBV-C E2 protein and 100 residues or less in length. Certain embodiments of the invention include various peptides and/or fusion proteins of GBV-C polypeptides, in particular GBV-C E2 protein. For example, all or part of a GBV-C E2 protein as set forth in SEQ ID NO: 5, SEQ ID NO: 6 and SEQ ID NO:8 may be used in various embodiments of the invention. In certain embodiments, a fragment of the GBV-C E2 may comprise, but is not limited to about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, 219, about 220 or more amino acid residues, and any range derivable therein.

It also will be understood that amino acid sequences may include additional residues, such as additional N- or C-terminal amino acids, and yet still be essentially as set forth in one of the sequences disclosed herein, so long as the sequence meets the criteria set forth above, including the maintenance of biological activity (e.g., immunogenicity) where protein expression is concerned. Theses non-GBV-C E2 sequences may be termed "heterologous."

A. Variants of GBV-C Polypeptides

Embodiments of the invention include various GBV-C polypeptides, peptides, and derivatives thereof. Amino acid sequence variants of a polypeptide can be substitutional, insertional or deletion variants. Deletion variants lack one or more residues of the native protein that are not essential for immunosuppressive activity. Insertional mutants typically involve the addition of material at a non-terminal point in the polypeptide. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of the GBV-C E2 polypeptides, provided the biological activity of the protein or peptide is maintained.

The term "functionally equivalent codon" is used herein to refer to codons that encode the same amino acid, such as the six codons for arginine or serine, and also refers to codons that encode biologically equivalent amino acids (see Table 1, below).

The following is a discussion based upon changing of the amino acids of a GBV-C E2 polypeptide or peptide to create an equivalent, or even an improved, second-generation molecule. For example, certain amino acids may be substituted for other amino acids in a protein structure without appreciable loss of interactive binding capacity with structures. Since it is the interactive capacity and nature of a protein that defines that protein's biological functional activity, certain amino acid substitutions can be made in a protein sequence, and in its underlying DNA or RNA coding sequence, and nevertheless produce a protein with like properties. It is thus contemplated by the inventors that various changes may be made in the DNA or RNA sequences of genes or coding regions without appreciable loss of their biological utility or activity, as discussed herein. Table 1 shows the codons that encode particular amino acids.

TABLE 1

CODON TABLE

| Amino Acids | | Codons | | | | |
|---|---|---|---|---|---|---|
| Alanine | Ala A | GCA | GCC | GCG | GCU | |
| Cysteine | Cys C | UGC | UGU | | | |
| Aspartic acid | Asp D | GAC | GAU | | | |
| Glutamic acid | Glu E | GAA | GAG | | | |
| Phenylalanine | Phe F | UUC | UUU | | | |
| Glycine | Gly G | GGA | GGC | GGG | GGU | |
| Histidine | His H | CAC | CAU | | | |
| Isoleucine | Ile I | AUA | AUC | AUU | | |
| Lysine | Lys K | AAA | AAG | | | |
| Leucine | Leu L | UUA | UUG | CUA | CUC | CUG | CUU |
| Methionine | Met M | AUG | | | | |
| Asparagine | Asn N | AAC | AAU | | | |
| Proline | Pro P | CCA | CCC | CCG | CCU | |
| Glutamine | Gln Q | CAA | CAG | | | |
| Arginine | Arg R | AGA | AGG | CGA | CGC | CGG | CGU |
| Serine | Ser S | AGC | AGU | UCA | UCC | UCG | UCU |
| Threonine | Thr T | ACA | ACC | ACG | ACU | |
| Valine | Val V | GUA | GUC | GUG | GUU | |
| Tryptophan | Trp W | UGG | | | | |
| Tyrosine | Tyr Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

It is understood that an amino acid substituted for another having a similar hydrophilicity value still produces a biologically equivalent and immunologically equivalent protein.

In certain embodiments, a GBV-C E2 polypeptide may be a fusion protein. Fusion proteins may alter the characteristics of a given polypeptide, such antigenicity or purification characteristics. A fusion protein is a specialized type of insertional variant. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification.

The present invention may employ peptides that comprise modified, non-natural and/or unusual amino acids. A table of exemplary, but not limiting, modified, non-natural and/or unusual amino acids is provided herein below. Chemical synthesis may be employed to incorporate such amino acids into the peptides of interest.

TABLE 2

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides. Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. These structures, which render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

The present invention may utilize an L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

B. In Vitro Production of GBV-C E2 Polypeptides or Peptides

Various types of expression vectors are known in the art that can be used for the production of protein products. Following transfection with a expression vector, a cell in culture, e.g., a primary mammalian cell, a recombinant product may be prepared in various ways. A host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented (for exemplary methods see Freshney, 1992).

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large-scale production of cells and cell products. However, suspension cultured cells have limitations, such as tumorigenic potential and lower protein production than adherent cells.

In further aspects of the invention, other protein production methods known in the art may be used, including but not limited to prokaryotic, yeast, and other eukaryotic hosts such as insect cells and the like.

C. Protein Purification

It may be desirable to purify anti-GBV-C E2 polypeptides and peptides, or variants and derivatives thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, hydrophobic interaction chromatography, exclusion chromatography; polyacrylamide gel electrophoresis; isoelectric focusing. A particularly efficient method of purifying peptides is fast protein liquid chromatography or even FPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme.

D. Peptide Synthesis

GBV-C E2-related peptides may be generated synthetically for use in various embodiments of the present invention. Because of their relatively small size, the peptides of the invention can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); Barany and Merrifield (1979), each incorporated herein by reference. Short peptide sequences, or libraries of overlapping peptides, usually from about 5 up to about 34 to 40 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

It may be desirable to purify GBV-C E2 polypeptide and peptides. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

III. GBV-C E2 POLYNUCLEOTIDES

Certain embodiments of the invention include GBV-C E2-coding polynucleotides or nucleic acid molecules and fragments thereof. The polynucleotides of the invention may be isolated and purified from GBV-C virus or cells infected or transfected with GBV-C polynucleotides. The term isolated indicating they are free or substantially free from total viral or cellular genomic RNA or DNA, and proteins. It is contemplated that an isolated and purified GBV-C nucleic acid molecule may take the form of RNA or DNA. A GBV-C E2 nucleic acid molecule refers to an RNA or DNA molecule that is capable of yielding all or part of a GBV-C E2 protein from a transfected cell.

As used in this application, the term "polynucleotide" refers to a nucleic acid molecule, RNA, or DNA that has been isolated free of total genomic nucleic acid. Therefore, a "polynucleotide encoding all or part of GBV-C E2" refers to a nucleic acid segment that contains GBV-C E2 coding sequences, yet is isolated away from, or purified and free of, total viral genomic RNA and proteins; similarly, a "polynucleotide encoding full-length GBV-C E2" refers to a nucleic acid segment that contains full-length GBV-C E2 coding sequences yet is isolated away from, or purified and free of, total viral genomic RNA and protein.

The term "cDNA" is intended to refer to DNA prepared using RNA as a template. The advantage of using a cDNA, as opposed to genomic RNA or an RNA transcript is stability and the ability to manipulate the sequence using recombinant DNA technology (See Maniatis, 1989; Ausubel, 1994). There may be times when the full or partial genomic sequence is preferred. Alternatively, cDNAs may be advantageous because it represents coding regions of a polypeptide and eliminates introns and other regulatory regions.

It also is contemplated that a given GBV-C E2 may be represented by natural variants or strains that have slightly different nucleic acid sequences but, nonetheless, encode the same viral polypeptides (see Table 1 above). Consequently, the present invention also encompasses derivatives of GBV-C E2 with minimal amino acid changes in its viral proteins, but that possesses the same activities.

The term "gene" is used for simplicity to refer to the nucleic acid giving rise to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding GBV-C E2 may contain a contiguous GBV-C E2 nucleic acid sequence of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more nucleotides, nucleosides, or base pairs. Such sequences may be identical or complementary to all or part of SEQ ID NO:1, 4 or Genbank Accession numbers AY196904 or AF070476.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode GBV-C E2 polypeptides or peptides that include within its amino acid sequence a contiguous amino acid sequence in accordance with, or essentially corresponding to GBV-C E2 polypeptides.

The nucleic acid segments used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The nucleic acid segments used in the present invention encompass biologically functional and/or immunogenically equivalent GBV-C E2 proteins and peptides. Such sequences may arise as a consequence of codon redundancy and functional equivalency that are known to occur naturally within nucleic acid sequences and the proteins thus encoded. Alternatively, functionally and immunologically equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

D. Vectors Encoding GBV-C E2

The present invention encompasses the use of vectors to encode for all or part of the GBV-C E2 polypeptide. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). In particular embodiments, gene therapy or immunization vectors are contemplated. One of skill in the art would be well equipped to construct a vector through standard recombinant techniques, which are described in Maniatis et al., 1988 and Ausubel et al., 1994, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" means that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202 and U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or exogenous, i.e., from a different source than GBV-C sequence. In some examples, a prokaryotic promoter is employed for use with in vitro transcription of a desired sequence. Prokaryotic promoters for use with many commercially available systems include T7, T3, and Sp6.

Table 3 lists several elements/promoters that may be employed, in the context of the present invention, to regulate the expression of a gene. This list is not intended to be exhaustive of all the possible elements involved in the promotion of expression but, merely, to be exemplary thereof. Table 4 provides examples of inducible elements, which are regions of a nucleic acid sequence that can be activated in response to a specific stimulus.

TABLE 3

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al; 1990 |
| Immunoglobulin Light Chain | Queen et al., 1983; Picard et al., 1984 |
| T-Cell Receptor | Luria et al., 1987; Winoto et al., 1989; Redondo et al; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrook et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |

TABLE 3-continued

Promoter and/or Enhancer

| Promoter/Enhancer | References |
|---|---|
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez at., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee et al., 1997), insulin-like growth factor II (Wu et al., 1997), human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome-scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames.

Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

8. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

E. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

F. Expression Systems

Numerous expression systems exist that comprise at least all or part of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al. (1992) and Gossen et al. (1995), and U.S. Pat. No. 5,650,298, all of which are incorporated by reference.

INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

G. Introduction of Nucleic Acids into Cells

In certain embodiments, a nucleic acid may be introduce into a cell in vitro for production of polypeptides or in vivo for immunization purposes. There are a number of ways in which nucleic acid molecules such as expression vectors may be introduced into cells. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

"Viral expression vector" is meant to include those vectors containing sequences of that virus sufficient to (a) support packaging of the vector and (b) to express a polynucleotide that has been cloned therein. In this context, expression may require that the gene product be synthesized. A number of such viral vectors have already been thoroughly researched, including adenovirus, adeno-associated viruses, retroviruses, herpesviruses, and vaccinia viruses.

Delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), liposome (Ghosh and Bachhawat, 1991; Kaneda et al., 1989) and receptor-mediated transfection (Wu and Wu, 1987; Wu and Wu, 1988). Some of these techniques may be successfully adapted for in vivo or ex vivo use.

In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro, but it may be applied to in vivo use as well.

IV. GBV-C RELATED IMMUNOTHERAPY

A. Inflammatory Conditions

The present invention relates to the use of GBV-C E2 compositions (polypeptides, peptides, nucleic acids coding therefor, and mimetics) for the modulation of immune responses, particularly those relating to pathologic inflammation. In one embodiment, the pathologic inflammation relates to interleukin-2 (IL-2) expression. IL-2 has multiple, sometimes opposing, functions during an inflammatory response. It is a potent inducer of T cell proliferation and T-helper 1 (Th1) and Th2 effector T cell differentiation and provides T cells with a long-lasting competitive advantage resulting in the optimal survival and function of memory cells. In a regulatory role, IL-2 is important for the development, survival, and function of regulatory T cells, it enhances Fas-mediated activation-induced cell death, and it inhibits the development of inflammatory Th17 cells. Thus, in its dual and contrasting functions, IL-2 contributes to both the induction and the termination of inflammatory immune responses.

The present invention would therefore seek to intervene in those disease whre, for example, IL-2 is activating T cells and leading to inflammatory states. Such diseases include autoimmune diseases like multiple sclerosis, psoriasis, inflammatory bowel disorders, early arthritis, juvenile arthritis, rheumatoid arthritis, enteropathic arthritis, psoriatic arthritis, ankylosing spondylitis, familial Mediterranean fever, amyotrophic lateral sclerosis, systemic lupus erythematosus, ulcerative colitis, inflammatory bowel disease, Sjögren's syndrome, or Crohn's disease. Other inflammatory conditions include cardiovascular disease, trauma, or pancreatitis.

B. Combinations with Anti-Inflammatories

It is common in many fields of medicine to treat a disease with multiple therapeutic modalities, often called "combination therapies." Inflammatory disease are no exception. To treat inflammatory disorders using the methods and compositions of the present invention, one would generally contact a target cell or subject with a GBV-C E2 agent and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the GBV-C E2 agent and the other includes the other agent.

Alternatively, the GBV-C E2 agent may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the GBV-C E2 agent or the other therapy will be desired. Various combinations may be employed, where the GBV-C E2 agent is "A," and the other therapy is "B," as exemplified below:

A/B/A B/A/B B/B/A A/A/B B/A/A A/B/B B/B/B/A

B/B/A/B A/A/B/B A/B/A/B A/B/B/A B/B/A/A

B/A/B/A B/A/A/B B/B/B/A A/A/A/B B/A/A/A

A/B/A/A A/A/B/A A/B/B/B B/B/A/B B/B/A/B

Other Combinations are Contemplated.

Agents or factors suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

V. PHARMACEUTICAL COMPOSITIONS AND ROUTES OF Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render proteins stable. Buffers also will be employed when proteins are introduced into a patient. Aqueous compositions of the present invention comprise an effective amount of the protein or polypeptide, dissolved or dispersed in a pharmaceutically acceptable carrier or aqueous media. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The percentage of active compound in any pharmaceutical preparation is dependent upon both the activity of the compound. Typically, such compositions should contain at least 0.1% active compound. The percentage of the compositions and preparations may, of course, be varied and may conveniently be between about 2 to about 60% of the weight of the unit. The amount of active compounds in such therapeutically useful compositions is such that a suitable dosage will be obtained.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy injection is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, phenylmecuric nitrate, m-cresol, and the like. In many cases, it will be preferable to use isotonic solutions, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active compounds in the required amount in the appropriate solvent with various of the other ingredients enumerated above, as required, followed by sterile filtration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques that yield a powder of the active ingredient plus any additional desired ingredient from a previously sterile-filtered solution thereof The present invention contemplates GBV-C E2 peptide and polypeptides, and nucleic acid molecules coding therefor. In some embodiments, pharmaceutical compositions are administered to a subject. Different aspects of the present invention involve administering an effective amount of an aqueous composition. In another embodiment of the present invention, therapeutic GBV-C E2 compositions are administered to a subject. Such compositions will generally be dissolved or dispersed in a pharmaceutically acceptable carrier or aqueous medium. Those of skill in the art are well aware of how to apply antibodies or other binding agents, as well as gene delivery to in vivo and ex vivo situations.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, intrathoracic, sub-cutaneous, or even intraperitoneal routes. Administration by i.v. or i.m. are specifically contemplated.

The compositions may be formulated as neutral or salt forms. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, it may be desirable to provide a continuous supply of compositions to the patient. For intravenous or intraarterial routes, this is accomplished by drip system. For various approaches, delayed release formulations could be used that provided limited but constant amounts of the therapeutic agent over and extended period of time. For internal application, continuous perfusion, for example with a GBV-C peptide, may be preferred. This could be accomplished by catheterization followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Peptides may be administered in a dose that can vary from 0.01, 0.05, 0.1, 0.5, 1, 5, 10, 20, 30, 40, 50, 60, 70, 80, 90, 100 mg/kg of weight to 50, 60, 70, 80, 90, 100, 110, 120, 130, 140, 150, 160, 170, 180, 190, 200 mg/kg of weight in one or more daily, weekly, monthly, or yearly administrations during one or various days, weeks, months, or years.

In many instances, it will be desirable to have multiple administrations of the peptides or other compositions of the invention. The compositions of the invention may be administered 1, 2, 3, 4, 5, 6, 7, 8, 9, 10, or more times. The administrations will normally be at from one to twelve week intervals, more usually from one to four week intervals.

Dosages commonly used for formulations that provide passive immunity are in the range of from 0.5 ml to 10 ml per dose, preferably in the range of 2 ml to 5 ml per dose. Repeated doses to deliver the appropriate amount of active compound are common Both the age and size by weight of the recipient must be considered when determining the appropriate dosage of active ingredient and volume to administer.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Expression of GBV-C E2 Proteins.

The near full-length GBV-C E2 protein (nt 1167-2161, GenBank AF 121950) coding sequences, E2 deletion mutants (N-terminal 219 amino acids (nucleotides 1167-1824)] and C terminal 112 amino acids (nucleotides 1824-2161)), and control sequences were ligated into a modified pTRE2-Hyg plasmid (Clontech Laboratories, Mountain View, Calif.) as described (Xiang et al., in press). This plasmid generates a bicistronic message encoding the viral sequence followed by the encephalomyocarditis virus (EMC) internal ribosomal entry site (IRES) that directs translation of GFP as previously described (Xiang et al., 2006).

Jurkat (tet-off) cell lines (Clontech, Inc) were transfected with plasmids encoding GBV-C E2 proteins, an E2 plasmid in which frameshift mutation was inserted to abrogate protein expression (FS) or the empty vector expressing green fluorescent protein (GFP) only (vector control; VC). Insert and control sequences were confirmed by sequencing plasmid DNA (University of Iowa DNA Core Facility). All transfections were accomplished using the Nucleofector II device (Lonza Inc.). Stable cell lines were generated after selection in hygromycin and neomycin (200 µg/ml) and GFP-positive cells were bulk sorted using a BD FACSDiva (University of Iowa Flow Cytometry Facility). Expression of GBV-C E2 protein or E2 mutants were analyzed either by western blot using tetra-his antibody (Qiagen) or GFP expression by flow cytometry (BD FACScan). All cell lines were maintained in RPMI 1640 supplemented with 10% fetal calf serum (heat-inactivated), 2 mM L-glutamine, 100 IU/ml penicillin, and 100 µg/ml streptomycin with hygromycin and neomycin (200 µg/ml).

Recombinant GBV-C E2 protein fused to Fc at the C terminus was constructed by inserting the human IgG Fc coding sequence at nt 2161 of GBV-C E2 in the pTRE2-Hyg vector. CHO cells were transfected and selected by hygromycin and GFP expression. Following stable transfection, cells were adapted to serum free media as described (McLinden et al., 2006). Fusion protein expressed in CHO cells was purified by protein G affinity chromatography as described Mohr et al., 2010), and analyzed by SDS-PAGE and immunoblot analysis as described (McLinden et al., 2006).

Cell Stimulation.

Jurkat cells ($1 \times 10^6$ cells/ml) were stimulated with plate-bound anti-CD3 (5 µg/ml, OKT3 clone, eBioscience) and soluble CD28 (5 µg/ml, clone CD28.2, BD Biosciences). Following obtaining written consent peripheral blood mononuclear cells (PBMCs) from four healthy subjects were isolated by Ficoll-Hypaque density gradient centrifugation. PBMCs were washed with PBS and incubated with purified GBV-C E2 protein (20 µg/ml) or purified human IgG (20 µg/ml, Sigma) for 48 hours and stimulated with anti-CD3 (500 ng/ml) and soluble CD28 (500 ng/ml). Following 24 hours of stimulation, cells were analyzed for measurement of cytokine and cellular receptor expression. To measure STAT5 phosphorylation Jurkat cells were prepared as described (Camargo et al., 2009). Briefly, cells were stimulated with 1 µg/ml of anti-CD3 and soluble CD28 for 48 hours followed by 24 hours of serum starvation. Cells were washed and incubated with IL-2 (250 U/ml; Zeptometrix) for 15 minutes. Cellular lysates were separated by polyacrylamide gel electrophoresis using 10% gels and membrane was incubated with anti-phospho Stat5 (pY694; BD Biosciences) or anti-Stat5 (BD Biosciences). Phosphorylation of Stat5 and total Stat5 expression was detected with Amersham ECL (GE Healthcare) using a Kodak Imager.

Cytokine Quantitation.

IL-2 cytokine released into cell culture supernatant was quantified using human IL-2 quantikine ELISA kit (R&D Systems, Minneapolis, Minn.) according to manufacturer's instructions.

mRNA Expression.

Total cellular RNA was extracted using RNeasy Mini Kit (Qiagen) following DNase treatment (RNase-Free DNase Set, Qiagen). Complementary DNA (cDNA) was generated using $RT^2$ First Strand cDNA Kit (SABiosciences) and relative expression of IL-2 and CD25 mRNA was determined using RT² qPCR primer assay for human IL2 and human CD25 (SABiosciences) and normalized to 18SrRNA using ABI 7500 Real Time PCR system.

Flow Cytometry—CD25 Surface Expression.

Cells were stained with the following antibodies from Becton Dickinson (BD) per manufacturer's recommendation; CD3 (V450), CD4 (PE), CD8 (Alexa700) and CD25 (APC) Staining was performed on ice for 1 hour and cells were subsequently washed 3 times with PBS. Data was acquired on BD LSR II flow cytometer using single stained CompBeads (BD Biosciences) for compensation. At least 10,000 total events were collected and FlowJo program (Tree Star Inc.) was used for data analysis.

Cell Proliferation.

Jurkat cells expressing GBV-C E2 protein or vector control (FS) were stained with cell proliferation dye (eFlour450, eBioscience) and stimulated with plate-bound anti-CD3 (1 µg/ml) and soluble CD28 (1 µg/ml) and cell proliferation was measured by gating eFlour450-positive cells in flow cytometry.

Statistics.

Statistics were performed using GraphPad software V4.0 (GraphPad Software Inc.). Comparisons between two groups were carried out using two-sided Student's t tests. P values less than 0.05 were considered statistically significant.

Example 2

Results

GBV-C E2 Protein Expression Inhibits IL-2 Production.

Figure 1A:
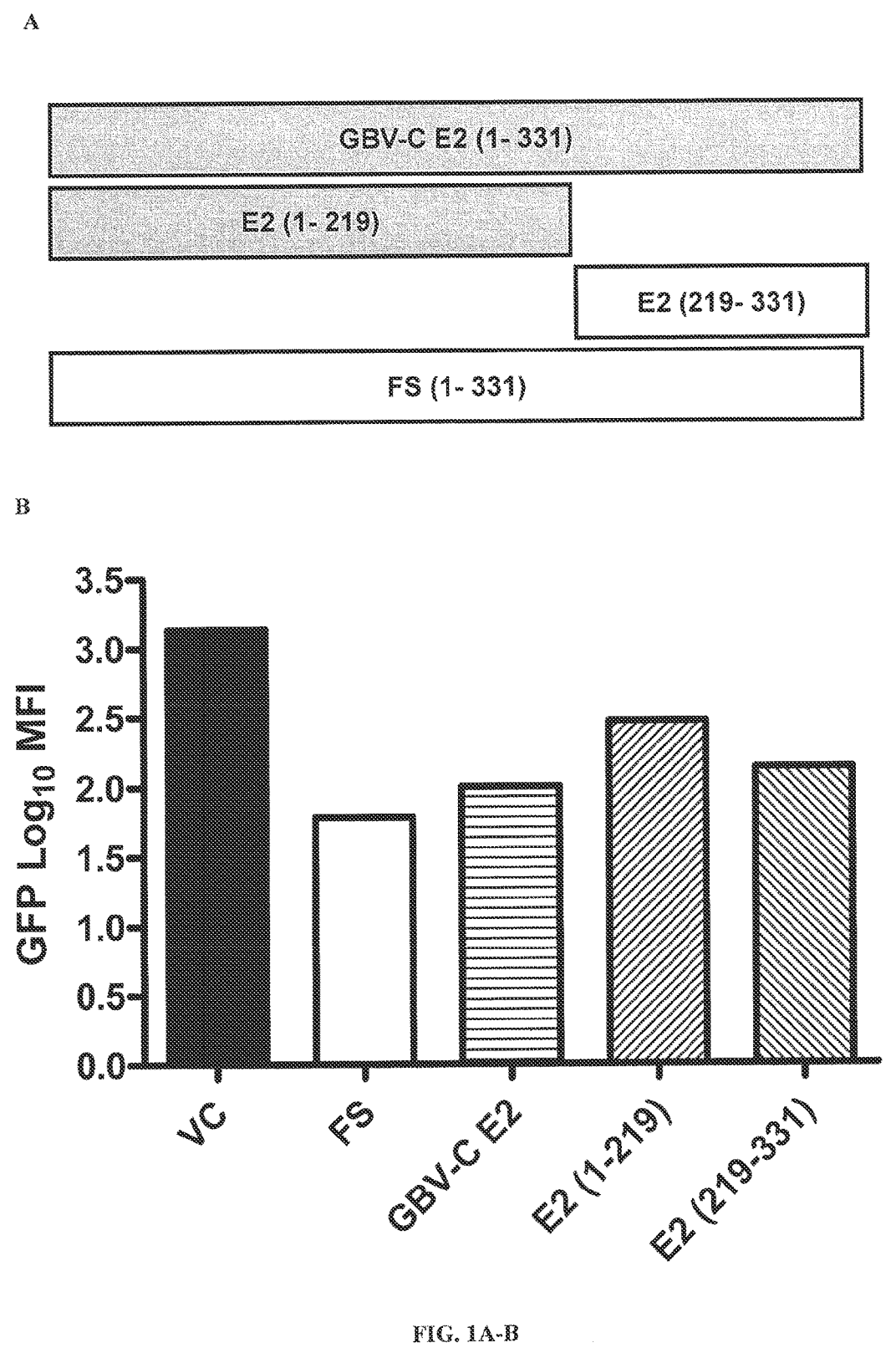
Figure 1C:
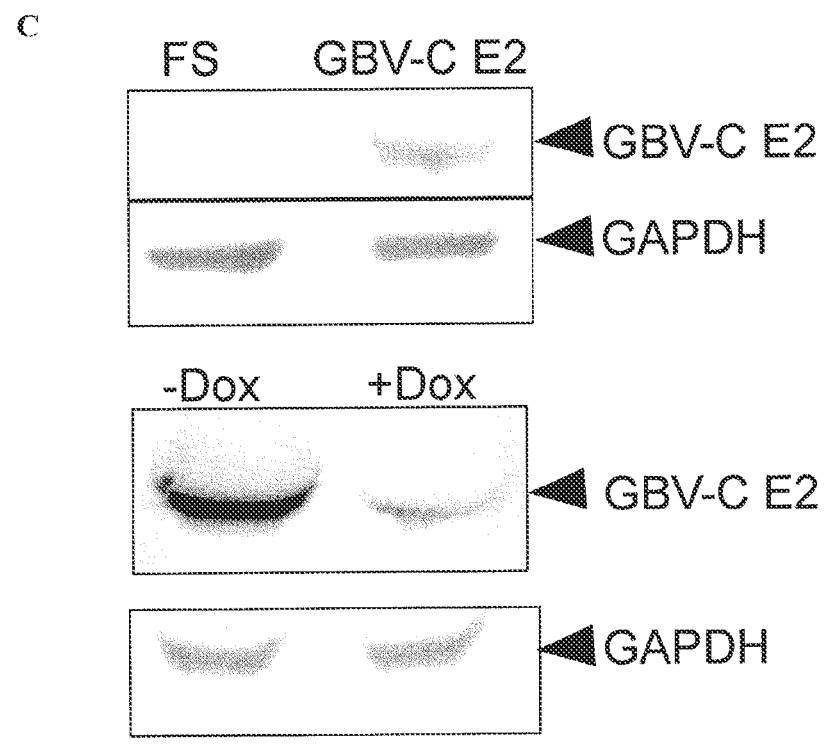

CD4+ Jurkat (tet-off) T cell lines that stably expressed the GBV-C E2 protein (331 amino acids), the N terminal 219 amino acids, and the coding region for the E2 protein with a frame-shift to abolish protein translation (FS) were previously described (reference—Jinhua). In addition, a stable cell line expressing the E2 protein region from amino acid 219 to 331 was generated (FIG. 1A). GFP expression in these cell lines was determined by flow cytometry (FIG. 1B), and the E2 protein expression was detected in Jurkat cell lysates with tetra-his antibody directed to C-terminal his-tag fused with E2 protein (FIG. 1C). Expression of GBV-C E2 RNA in Jurkats expressing E2 frameshift construct was confirmed by RT-PCR and DNA sequencing. E2 expressing Jurkat cells cultured with doxycycline (doxy, 1 µg/ml) had significantly reduced expression of E2 as determined by immunoblot (FIG. 1C) and flow cytometry (data not shown).

IL-2 production was significantly inhibited in Jurkat cells expressing GBV-C E2 compared to the VC following activation through T cell receptor (TCR) engagement with anti-CD3 and soluble CD28 antibodies (FIG. 2A). IL-2 inhibition required GBV-C E2 protein expression as Jurkat cells expressing E2 RNA but not protein (FS) did not inhibit IL-2 production (FIG. 2A). Jurkat cells expressing the N terminal 219 amino acids of GBV-C E2 protein (E2 1-219) also reduced IL-2 production compared to the VC; however, the C-terminal E2 amino acids (219 to 331) did not inhibit IL-2 production following stimulation (FIG. 2A). Steady state IL-2 mRNA levels were significantly reduced in GBV-C E2 expressing cells compared to the VC and E2 RNA expressing cells (FS), suggesting that the reduction is due to a reduction in IL-2 mRNA transcription (FIG. 2B). Growing GBV-C E2 expressing Jurkats in doxycycline (dox) reduced E2 expression (FIG. 1C), and this restored the concentration of IL-2 mRNA suggesting GBV-C E2 protein expression alters TCR-mediated IL-2 transcription (FIG. 2B).

GBV-C E2 Protein Expression Inhibits CD25 Expression and STAT5 Phosphorylation.

Surface expression of CD25, the alpha chain of IL-2 receptor is upregulated following activation of T cells (reviewed in Cheng et al., 2011; Kim et al., 2006). Following upregulation, CD25 interacts with CD122 (IL-2 beta) and CD132 (IL-2-gamma) to form the high affinity IL-2 receptor (IL-2R) that binds IL-2 and initiates IL-2 signaling (reviewed in Cheng et al., 2011; Kim et al., 2006). Since GBV-C viremia is associated with altered response to IL-2 therapy in HIV-infected subjects (Stapleton et al., 2009), the inventors examined the effect of GBV-C E2 protein on CD25 expression. The percentage of CD25+ cells was significantly lower in Jurkat cells expressing GBV-C E2 compared to controls and Jurkat cells cultured in doxycycline (FIG. 3A). Furthermore, GBV-C E2 expression abrogated the upregulation of CD25 following TCR engagement, and this was prevented by growing the Jurkat cells expressing E2 in doxycycline (FIG. 3A). GBV-C E2 expression resulted in a reduction in CD25 mRNA levels, suggesting that the mechanism of CD25 reduction is mediated specifically by GBV-C E2 protein effects on CD25 transcription (FIG. 3B). Since CD25 expression is essential for IL-2 signaling we further investigated the effect of GBV-C E2 protein expression on IL-2 signaling pathways. Phosphorylation of STAT5 is rapidly detected after IL-2 and IL-2R interaction and is critical for IL-2 signaling (Lin and Leonard, 1997). Following stimulation with IL-2 for 15 minutes, STAT5 phosphorylation was detected in FS control cells but was completely inhibited in Jurkat cells expressing GBV-C E2 protein (FIG. 3C). Since total STAT5 protein expression did not alter by GBV-C E2 protein expression (FIG. 3C) these data indicate a significant alteration of IL-2 signaling pathway by GBV-C E2 protein.

GBV-C E2 Protein Reduces Activation Induced Proliferation in Jurkat Cells.

Figure 4A:
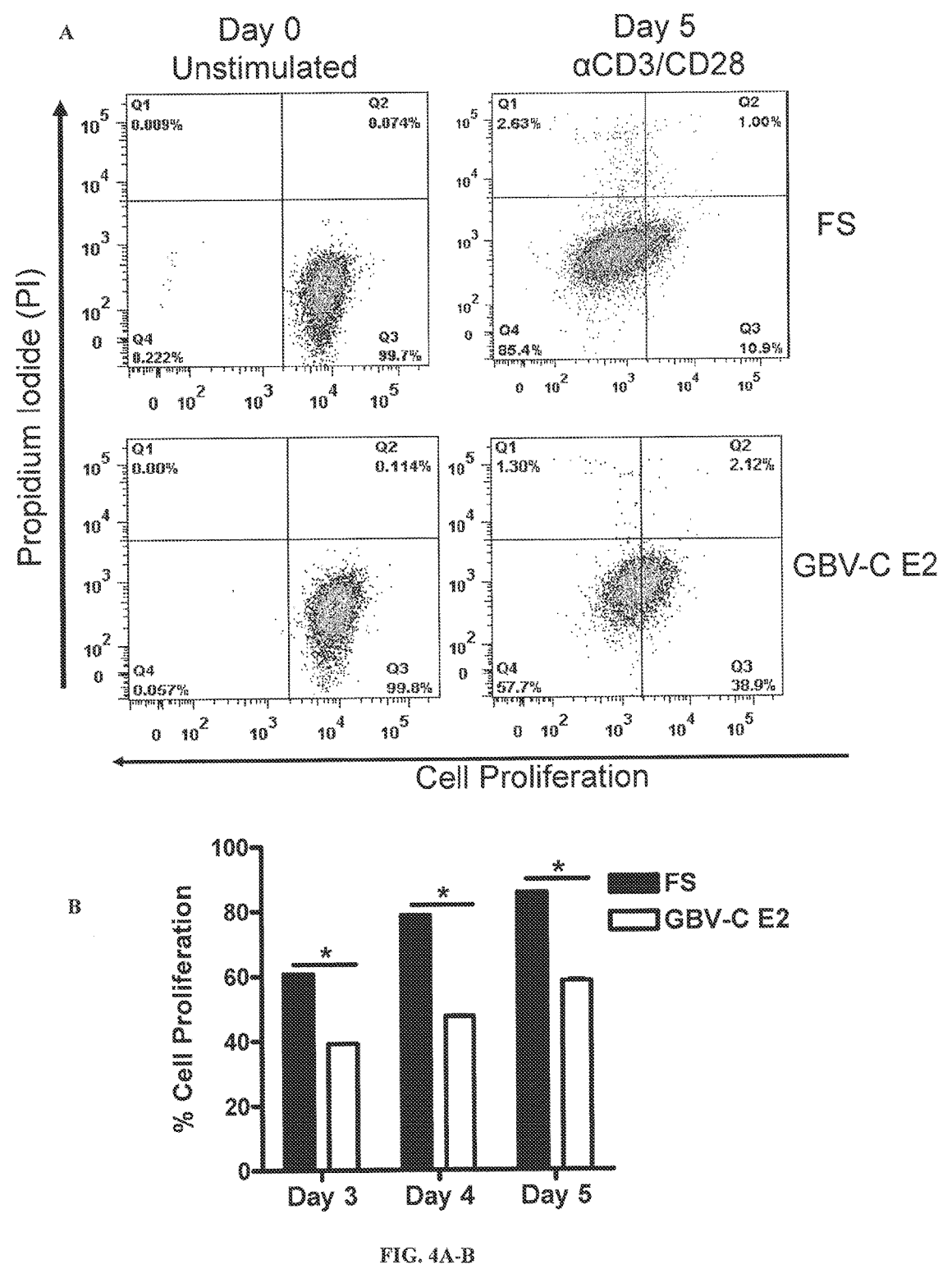

To examine if GBV-C E2-expression-induced inhibition of IL-2 release, CD25 expression and STAT5 phosphorylation affected T cell proliferation, the inventors assessed Jurkat cells expressing GBV-C E2 or FS by flow cytometry. At baseline, there was no difference in the percentage of Jurkat cells positively stained for the proliferation dye eFlour450 compared to control cells (Day 0, FIG. 4A). However, following TCR engagement with anti-CD3/CD28, GBV-C E2 protein reduced proliferation in Jurkat cells compared to the FS control (Day 5, FIG. 4A). Cell proliferation was significantly reduced in Jurkats expressing E2 protein during five days of anti-CD3/CD28 stimulation (FIG. 4B).

GBV-C E2 Protein Inhibits IL-2 Production and CD25 Expression in Primary CD4+ and CD8+ T cells.

Figure 5A:
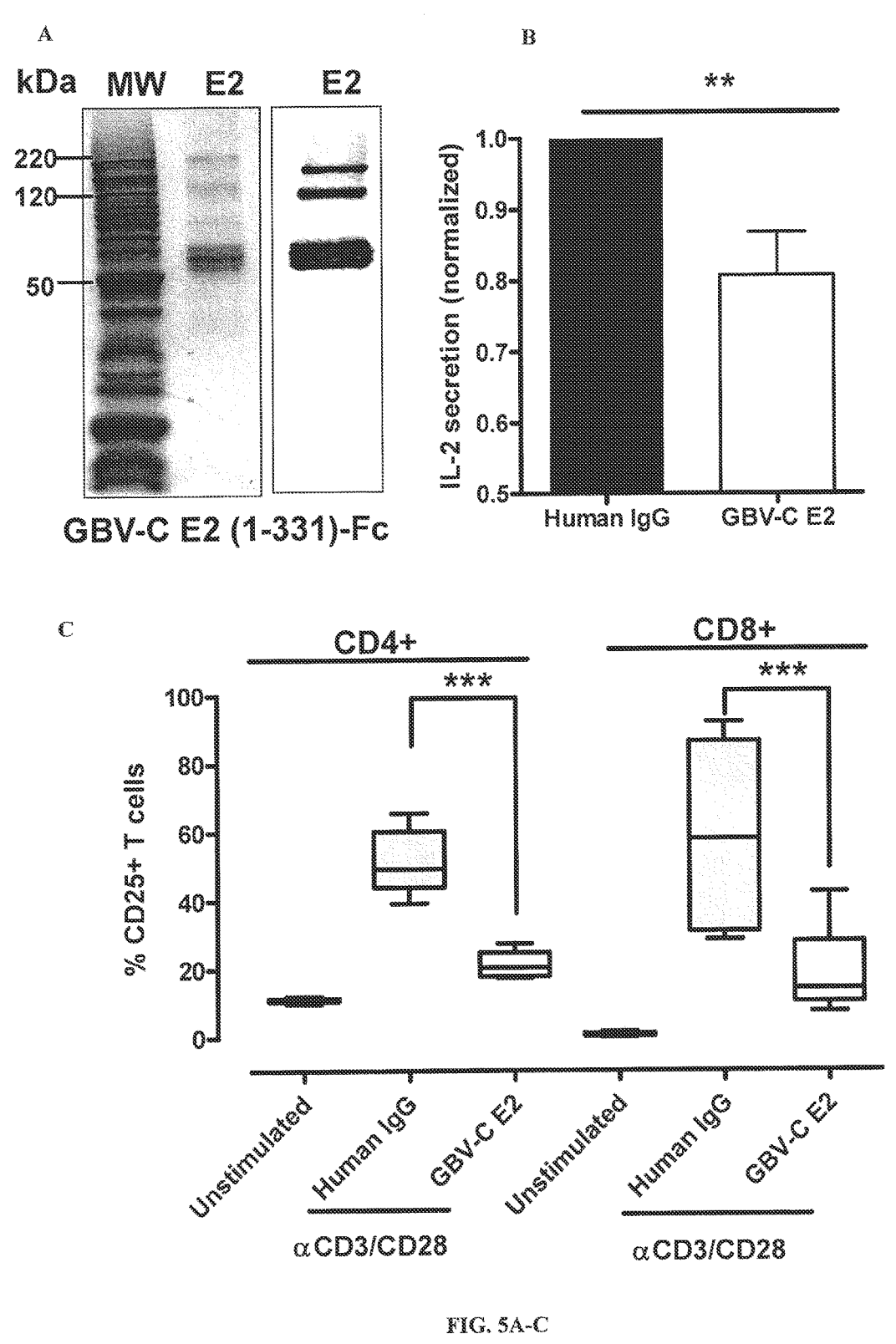

Recombinant GBV-C E2 protein fused to human IgG Fc was analyzed by SDS-PAGE and immunoblot analysis. Purified protein fractions were enriched for GBV-C E2 and reacted with anti-human IgG antibodies (FIG. 5A). Following stimulation with anti-CD3/CD28, IL-2 secretion was significantly reduced in PBMCs from healthy subjects incubated with GBV-C E2 protein compared to human IgG (n=4; P=0.008) (FIG. 5B). Consistent with findings in Jurkat cells, following stimulation with anti-CD3/CD28, CD25 expression was significantly reduced in CD4+ and CD8+ T cells from healthy subjects incubated with GBV-C E2 protein compared to the IgG control (FIG. 5C).

Mechanism(s) for GB Virus C (GBV-C) E2 Protein Inhibition of T Cell Activation.

In humans infected with GBV-C, circulating CD4+ and CD8+ T cells have significantly lower levels of surface receptors that associated with T cell activation (Maidana-Giret et al., 2009). To date, no mechanism for how this phenotype has been described. The inventors investigated the hypothesis that GBV-C envelope glycoprotein E2 may alter T cell signaling, leading to a block in activation following activation stimuli. They expressed the GBV-C E2 protein truncated at the C-terminus to remove the transmembrane domain (aa 1-331; or nucleotides 1167-2161 based on GenBank Accession No. AF121950) in a Jurkat (CD4+) T cell line. Cell lines expressing smaller portions of E2 were also generated (1-219, 219-331), and control cells including a vector control and a control cell line in which nt 1167-2161 were transcribed, but in which a frame shift was inserted to abolish translation of the E2 (1-331) protein.

Figure 7:
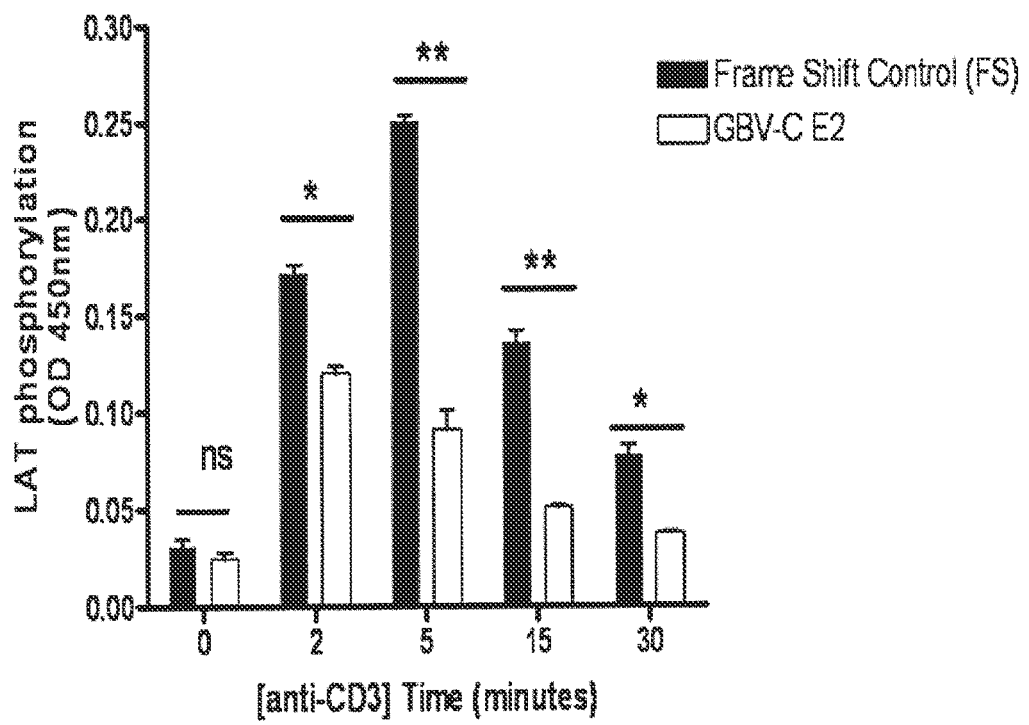
FIG. 7. GBV-C E2 expression inhibits LAT phosphorylation. Jurkat cells expressing GBV-C E2 or the frameshift control were stimulated with anti-CD3. LAT phosphorylation (Tyr191) was quantified by ELISA. * p<0.01.

Following stimulation with anti-CD3 and anti-CD28 antibody, cells expressing GBV-C E2 had significantly less activation, as measured by the activation-regulated marker CD69, than did the frame shift control cells (FS; FIG. 6A). Reduction in E2 expression by growing cells in doxycycline (these are Tet-Off cells) restored activation response (CD69 surface expression) in the cells containing E2 protein (FIG. 6B). To assess T cell receptor (TCR)-related signaling pathways, LAT phosphorylation was assessed by ELISA, and E2 protein expression was associated with significantly less phosphorylation of LAT following TCR activation (FIG. 7).

Figure 8:
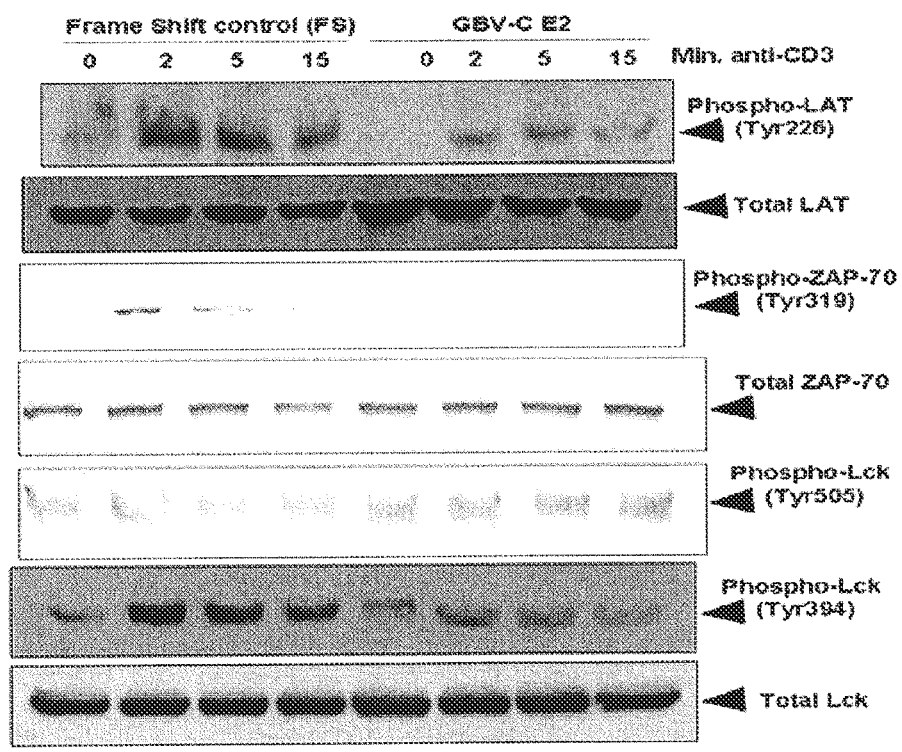
FIG. 8. GBV-C E2 inhibits TCR signaling. Jurkat cells stably expressing GBV-C E2 or the FS control were stimulated with anti-CD3. Phosphorylation of LAT (Y226), ZAP-70 (Y319) and Lck (Y394 and Y505) was determined by immunoblot. Phosphorylation of LAT, ZAP-70 and Lck (Y394) was inhibited by E2 expression compared to FS control.
Figure 9:
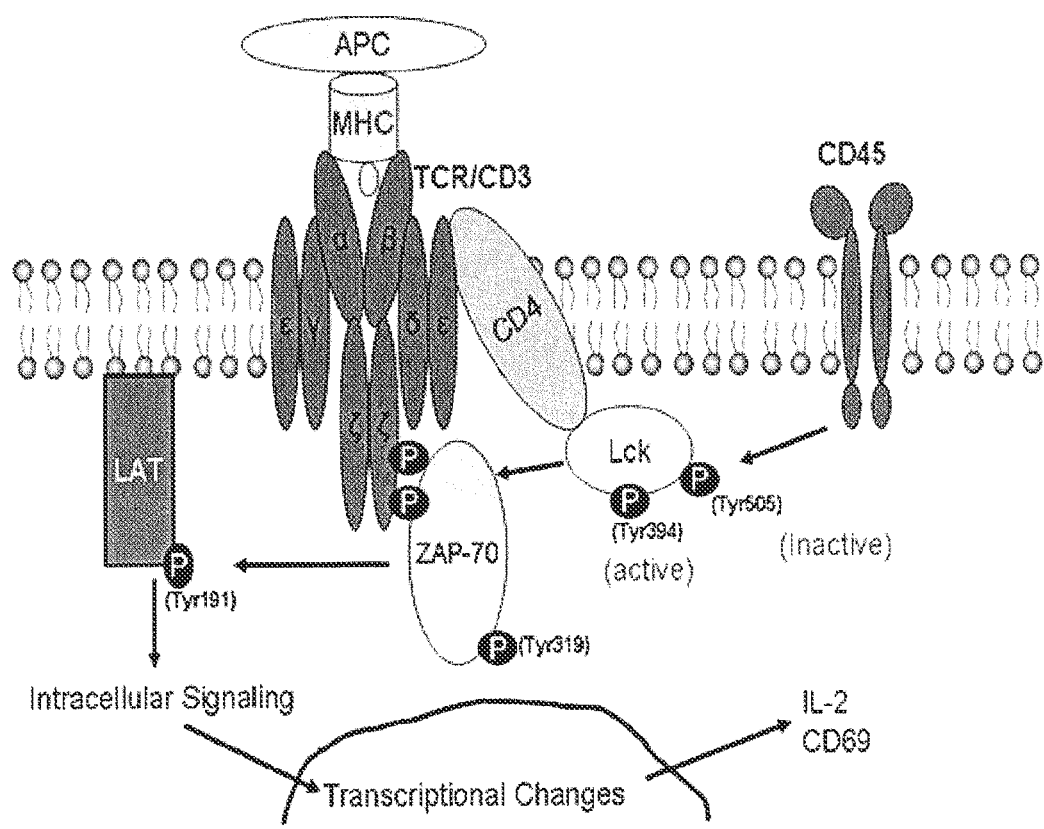
FIG. 9. T-cell signaling pathways. Following engagement of the T cell receptor (TCR), monophosporylated Lck is dephosphorylated by CD45 (phosphatase), leading to a conformational change exposing tyrosine (394) that allows phosphorylation and activation. This leads ZAP-70 and LAT phosphorylation, downstream signaling and activation.
Figure 10:
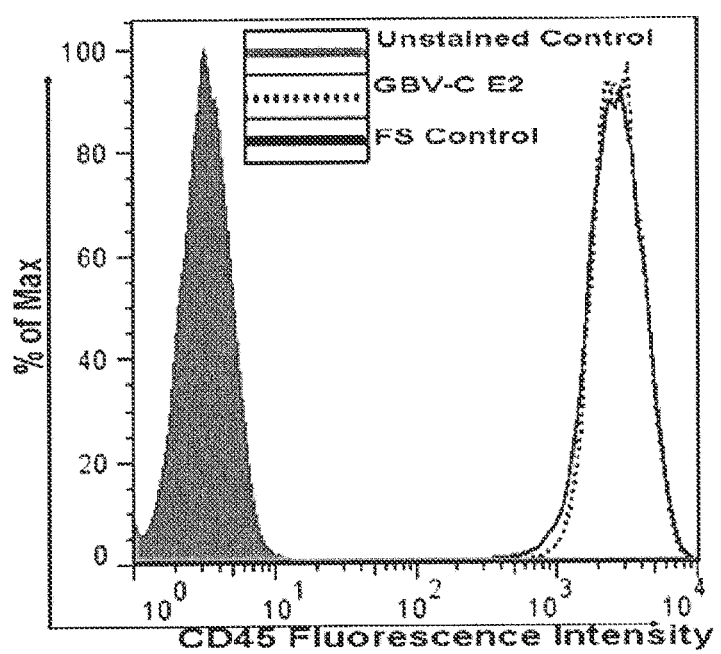
FIG. 10. Lck phosphorylation is not diminished due to altered CD45 phosphatase activity. CD45 is required for the activation of Lck. Cell surface CD45 was not different between E2-expressing cells and the FS control.
Figure 11:
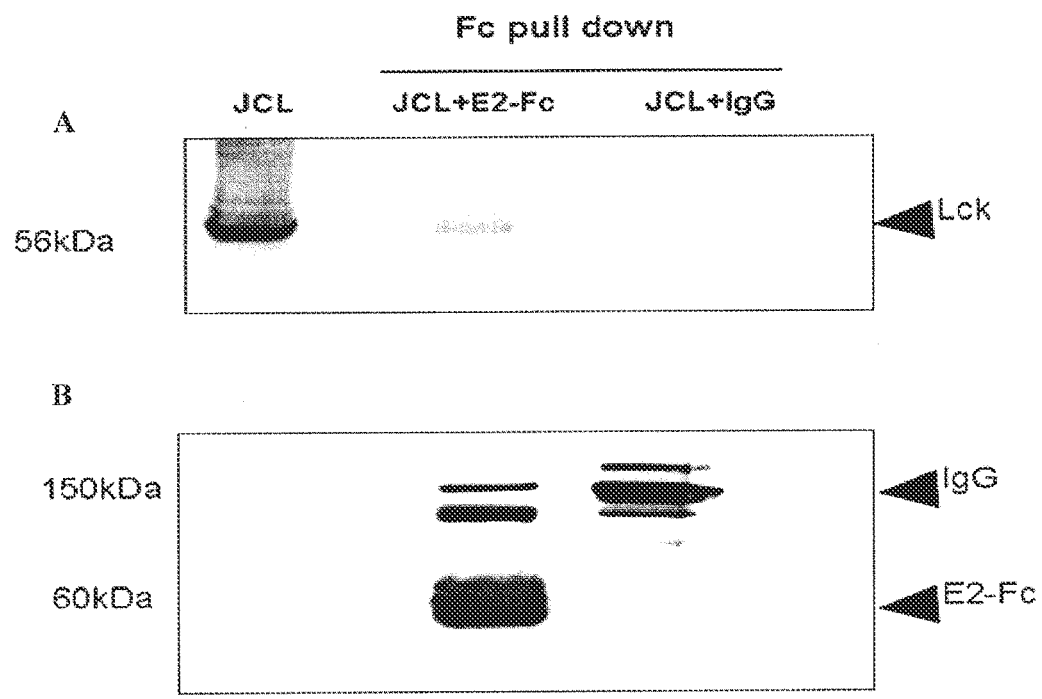
FIGS. 11A-B. GBV-C E2 protein interacts with Lck. Parental Jurkat cell lysate (JCL) was incubated with recombinant GBV-C E2-Fc fusion protein or IgG and precipitated with protein A/G beads. JCL control, JCL+E2-Fc, and JCL+IgG pull-downs are shown as indicated. Lck (FIG. 11A) and E2-Fc or IgG (FIG. 11B) were identified by immunoblot and anti-Lck or anti-Fc antibodies.

Further assessment using immune blot analysis revealed that E2 protein expression reduced activation of LAT, ZAP 70, and Lck (at the activation site of amino acid 394), all critical molecules in the activation cascade initiated by engagement of the TCR (FIGS. 8-9). As shown in FIG. 9, CD45 dephosphorylation of Lck at position 505 is required for activation of Lck. Lck505 is not diminished following TCR engagement (FIG. 8). This was not due to altered CD45 expression on the GBV-C E2 expressing Jurkat cells (FIG. 10). To determine if GBV-C E2 interacted with Lck, jurkat cell lysates were incubated with recombinant GBV-C E2 (fused to human Fc protein) or human IgG and precipitated with protein A/G beads. Lck was readily detected in the control lysate. E2-Fc precipitated Lck while human IgG did not (FIG. 11A). Similarly, GBV-C E2 expressing Jurkat cell lysates were incubated with anti-Lck antibody or isotype control IgG and precipitated with protein A/G beads. GBV-C E2 was precipitated by Lck (FIG. 11B). Thus, GBV-C E2 directly interacts with the Src-family kinase Lck.

In summary, expression of the GBV-C envelope glycoprotein E2 in Jurkats (CD4+ T cells) significantly inhibited activation (CD69 surface expression) upon TCR stimulation suggesting T cell activation pathways are modulated by E2 protein expression. The activation of proximal signaling downstream of the TCR, specifically LAT, ZAP-70 and Lck, was inhibited by GBV-C E2 protein expression. The Lck activation was not due to altered CD45 phosphatase levels or activity (data not shown) Immuno-precipitation and pull down experiments demonstrated interactions between GBV-C E2 protein and Lck. Thus, GBV-C directly interacts with Lck, the critical T cell tyrosine kinase in the Src kinase family, reducing downstream signaling. This leads to a reduction in T cell activation, release of proinflammatory cytokines, and proliferation. These represent a novel approach to modulating T cell activation and inflammation.

Example 3

Materials and Methods

Expression of GBV-C E2 protein. Tet-off Jurkat cell lines expressing GBV-C E2 protein (nt 1167-2161 based on GenBank AF 121950), the vector control (expressing GFP) and E2 coding sequence with a plus one frameshift mutation inserted to abolish protein expression (FS control) were previously described[12]. Six truncated E2 proteins were cloned into a modified pTRE2-HGY plasmid (Clontech, Inc.) as described[28]. This plasmid generates a bicistronic message encoding the GBV-C E2 sequence followed by the encephalomyocarditis virus (EMC) internal ribosomal entry site (IRES) that directs translation of GFP. Jurkat (tet-off) cell lines (Clontech, Inc) were transfected (Nucleofector II, Lonza Inc.) and cell lines were selected for resistance to hygromycin and neomycin. GFP-positive cells were bulk sorted using a BD FACS Diva (University of Iowa Flow Cytometry Facility). Protein expression was analyzed by measuring GFP by flow cytometry (BD LSR II) and by immunoblot using antibodies directed against a C-terminal histidine tag (Qiagen). All cell lines were maintained in RPMI 1640 supplemented with 10% fetal calf serum (heat-inactivated), 2 mM L-glutamine, 100 IU/ml penicillin, and 100 µg/ml streptomycin with hygromycin and neomycin (200 µg/ml). Insert sequences were confirmed by sequencing plasmid DNA (University of Iowa DNA Core Facility).

Cell Stimulation.

Jurkat cells ($5 \times 10^6$ cells/ml) were stimulated with plate-bound anti-CD3 (5 µg/ml, OKT3 clone, eBioscience) and soluble CD28 antibody (5 µg/ml, clone CD28.2, BD Biosciences) unless stated otherwise. For co-culture experiments, non-transfected GFP-negative Jurkat cells were ($5 \times 10^5$ cells/ml) were incubated with either transfected GFP-positive vector control or GFP-positive GBV-C E2-expressing cells ($1 \times 10^6$ cells/ml) for 72 hours prior to stimulation with anti-CD3/CD28. Following 24 hours of stimulation, cellular receptor expression and cytokine release were measured by flow cytometry in GFP-negative cells and by ELISA respectively.

Flow Cytometry.

Cellular receptor expression was measured using the following antibodies per manufacturer's recommendation: CD69 (PE), CD25 (APC), CD45 (PE) (BD Biosciences). Cells were incubated on ice for 1 hour, washed 3 times with PBS and fixed in 2% paraformaldehyde (Polysciences). Data was acquired on BD LSR II flow cytometer using single stained CompBeads (BD Biosciences) for compensation. At least 10,000 total events were collected in each experiment and the FlowJo program (Tree Star Inc.) was used for data analysis. All flow cytometry experiments were repeated at least three times with consistent results.

Immunoblot Analysis.

Jurkat cells ($5 \times 10^6$) were stimulated with anti-CD3 (5 µg/ml) for indicated times prior to the addition of cell lysis buffer (Cell Signaling) for 15 minutes and briefly sonicated. Lysates were separated by polyacrylamide gel electrophoresis and transferred to nitrocellulose membranes (BIO-RAD). Membranes were incubated in protein-free blocking buffer (Thermo Scientific) for 1 hour at room temperature followed by incubation with primary antibodies Immunoreactive proteins were detected with Amersham ECL (GE Healthcare) using a Kodak Imager. Protein phosphorylation was quantified using ImageJ (NIH) and normalized to total protein levels. Primary antibodies used were: pLAT (Y226; BD Biosciences); total LAT (Biolegend); CD63 antibodies (Systems Biosciences); and pZAP70 (Y319); total ZAP70; pLck (Y505); pLck (Y394/pSrcY416); total Lck (Y394) and total Csk (all from Cell Signaling Technology). For immune precipitation studies, Jurkat cell lysates were incubated with recombinant Fc fused GBV-C E2 protein[12] or alternatively GBV-C E2 expressing Jurkat cell lysates were incubated with anti-Lck antibodies overnight at 4° C. as described. Protein complexes were isolated from the cellular lysates using protein A/G agarose beads (Thermo Scientific) and precipitated proteins were detected as described above.

ELISA.

pLAT (Y191) was quantified using PathScan ELISA kit (Cell Signaling Technology) and IL-2 cytokine released into cell culture supernatant was quantified using human IL-2 quantikine ELISA kit (R&D Systems) according to manufacturer's instructions.

Enzyme Assays.

CD45 activity was measured using CD45 tyrosine phosphatase assay kit (Enzo Life Sciences) following the manufacturer's instructions. Purified recombinant GBV-C E2 protein expressed in CHO cells was described previously[2]. Enzymatic activity was evaluated with or without GBV-C E2 protein (10 μg) or human IgG control (10 μg; Sigma) at room temperature. Following 1 hour incubation, the reaction was terminated and absorbance determined by a Microplate reader (Model 680, Bio-Rad) at $OD_{620nm}$. Phosphorylation of GBV-C E2 protein by Lck was measured by incubating recombinant E2 protein (40 μg) with or without human Lck (500 μg; R&D Systems) as recommended by the manufacturer. Samples were subjected to immunoblot analysis as described above. Phosphorylation was determined by immunoblot analysis with phosphotyrosine antibodies (Invitrogen) and GBV-C E2 protein was identified using an anti-E2 monoclonal antibody. Lck mediated phosphorylation of GBV-C E2 derived TAT-peptides were performed using Lck kinase enzyme system (Promega) as recommended by the manufacturer.

GBV-C E2 Synthetic Peptides.

FITC labelled synthetic peptides with an N-terminal HIV TAT protein transduction domain (TAT) alone (GGGGGRK-KRRQRRR; SEQ ID NO: 13), or with the GBV-C E2 aa 86-101 (GGGGGRKKRRQRRRVYGSVSVTCVWGS; SEQ ID NO: 14; Y87), or the Y87H mutation (GGGGGRK-KRRQRRRVHGSVSVTCVWGS; SEQ ID NO: 15) were obtained from Ana Spec, Inc. Peptides with the TAT domain and GBV-C E2 aa 276-292 (GGAGLTGGRYEPLVRRC; SEQ ID NO: 16), or the same amino acids in a scrambled order (GCRCARGVLLTPGEGYF; SEQ ID NO: 17) as previously described[28]. Peptides were dissolved in RPMI with 10% DMSO. The TAT domain enhances cellular uptake of the peptide. Healthy donors PBMCs (1×10⁶ cells/ml) were incubated with 20 μg peptide at 37° C. over night before stimulation with 500 ng/ml anti-CD3/CD28. IL-2 release and cellular receptor expression was analyzed 24 hrs later.

GBV-C RNA Quantification.

GBV-C viremic HIV-infected subjects receiving cART who were attending the University of Iowa HIV Clinic and healthy volunteer blood donors were invited to participate. HIV-infected subjects' HIV viral load (VL) was below the limit of detection (<48 copies/mL) for a minimum of 6 months and at the time of blood donation. All subjects provided written informed consent and the study was approved by the University of Iowa Institutional Review Board. PBMCs were prepared as described[4]. For sorting experiments, CD3+ T cells were enriched using Automacs (Miltenyi Biotech), and CD3+ T cells were sorted into CD4+ and CD8+ populations by FACS (BD ARIA II) using CD3 (V450), CD4 (FITC), CD8 (Alexa700) antibodies (all BD Biosciences). Sorted cells were counted using Countess™ automated cell counter (Invitrogen). Total cellular RNA from specific T cell populations was isolated and GBV-C RNA was quantified by real-time RT-PCR as described[4].

Extracellular Microvesicles (EMV) Isolation.

EMV were purified from the clarified cell-culture supernatant or from human serum using ExoQuick reagent (Systems Biosciences) according to the manufacturer's instructions. This commercial reagent has been previously reported to yield EMV from cell culture supernatant and human serum[29-32]. Sodium chloride (NaCl) density flotation was performed as described[23]. Briefly, 1 ml of undiluted serum was mixed with 35 ml of NaCl solution (1.063 g/ml), and centrifuged in a Beckman SW28 rotor (112,000×g, 4° C.). After 65 hours of spin, top and bottom fractions were collected for subsequent analysis. PBMCs from healthy donors were incubated with EMV purified from 5 ml of GBV-C-positive or GBV-C-negative serum or EMV purified from 10 ml of culture supernatant overnight and stimulated with anti-CD3/CD28 antibodies (500 ng/ml) for 24 hours before analysis.

Statistics.

Statistics were performed using GraphPad software V4.0 (GraphPad Software Inc.). Two-sided Student's t test was used to compare results between GBV-C E2 protein expressing cells and controls. P values less than 0.05 were considered statistically significant.

Example 4

Results

Figure 12:
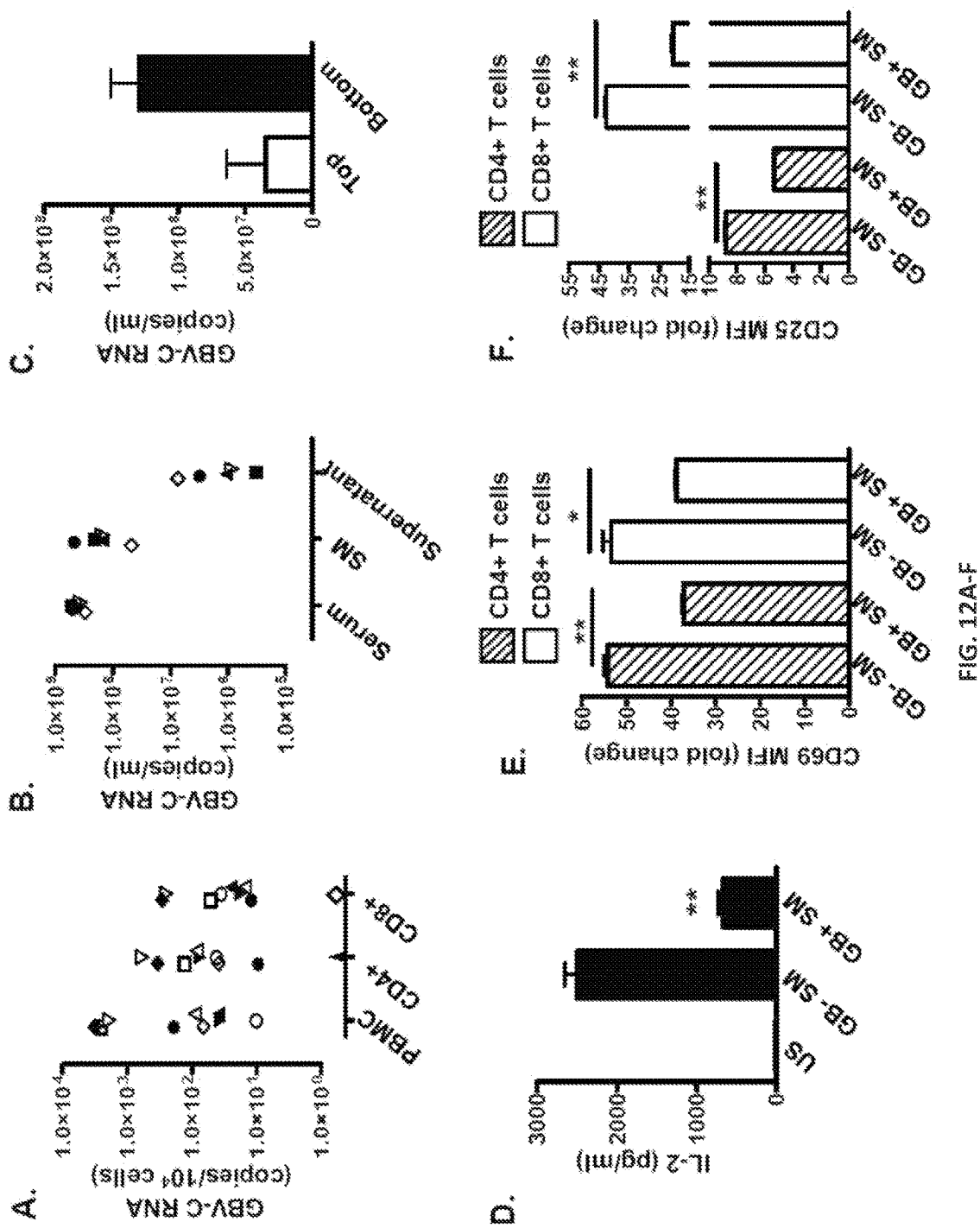
FIGS. 12A-F. Extracellular microvesicles from GBV-C infected human serum inhibit T cell receptor (TCR) signaling in primary human T cells. Quantification of GBV-C RNA in peripheral blood mononuclear cells (PBMC), and purified CD4+ and CD8+ T cells obtained from nine GBV-C infected subjects (FIG. 12A). Quantification of GBV-C RNA in the serum, extracellular microvesicles (EMV) purified from the serum and supernatant after isolating microvesicles from five individuals with GBV-C infection (FIG. 12B). Quantification of GBV-C RNA in the top and bottom fraction after GBV-C-positive serum was subjected to saline flotation gradient (FIG. 12C). IL-2 release (FIG. 12D), CD69 and CD25 cell surface expression (FIGS. 12E-F) in PBMCs from healthy donors incubated with GBV-C-positive (GB+) or -negative (GB−) serum derived EMV and stimulated with CD3 and CD28 antibodies. -Fold change was calculated by measuring CD69 and CD25 levels before and after stimulation. US=unstimulated, MFI=mean fluorescence intensity. Data represent the average of three independent cultures. *P<0.05; **P<0.01
Figure 18:
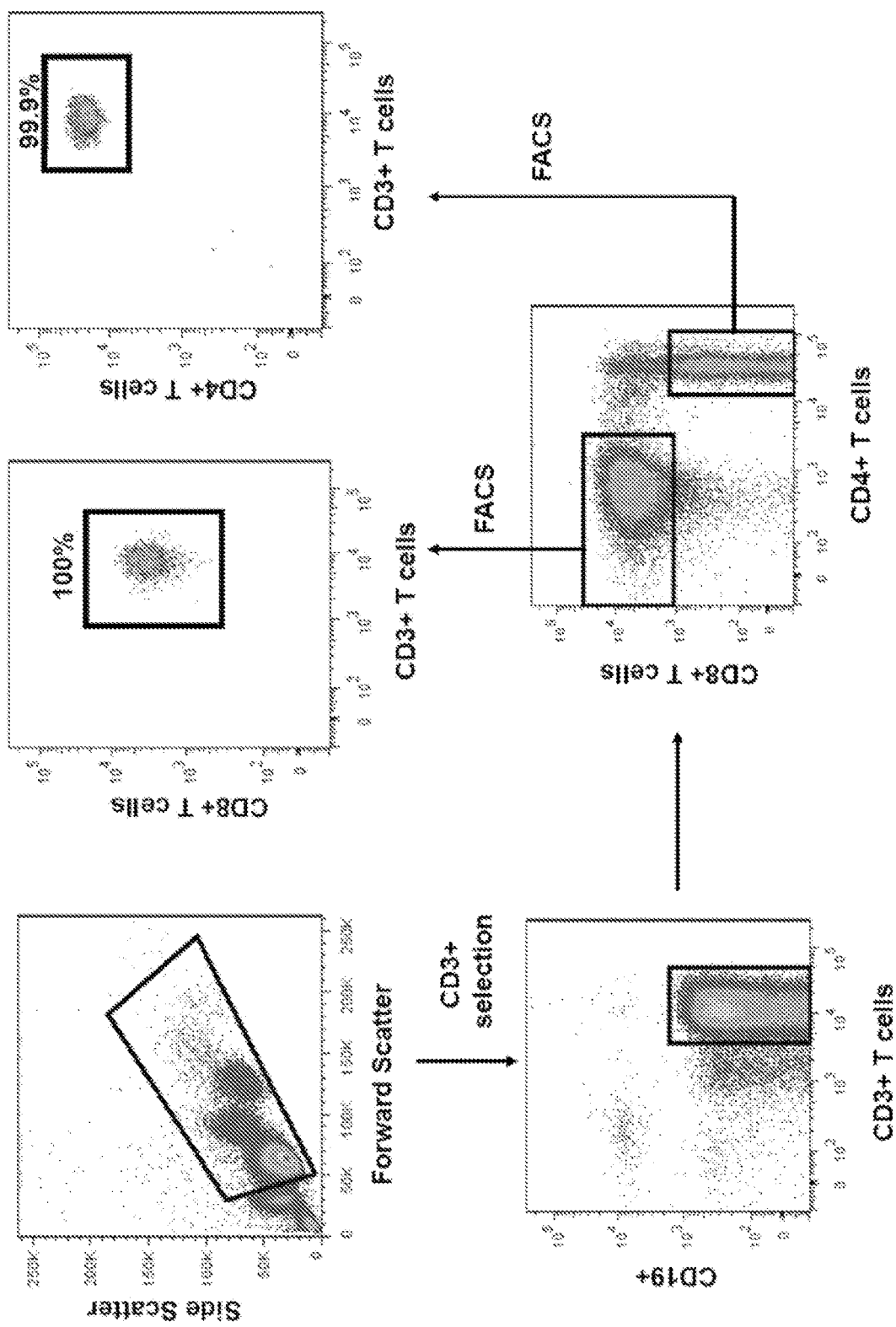
FIG. 18. Purification of CD4+ and CD8+ T cells from GBV-C viremic subjects. PBMCs from nine GBV-C viremic subjects were subjected to immunoaffinity selection for CD3+ T cells using magnetic beads followed by flow cytometric (FACS) purification of CD4+ and CD8+ T cells using antibodies. Purity of sorted CD4+ and CD8+ T cells were above 99%.

Extracellular microvesicles from GBV-C infected human serum inhibit TCR signaling in primary human T cells. GBV-C infection is associated with global reduction in T cell activation and reduced IL-2 signaling in the peripheral blood mononuclear cells (PBMCs)(Rydze, et al., 2012; Bhattarai et al., 2012; Stapleton, 2009; Maidana-Giret, 2009 and Stapleton, 2012). Since the frequency of GBV-C infected lymphocytes in peripheral blood is unknown, we quantified GBV-C RNA copy number within CD4+ and CD8+ T cells obtained from nine GBV-C viremic subjects. Using immuno-affinity selection and fluorescent activated cell sorting (FACS) to sort CD4+ and CD8+ T cells from peripheral blood mononuclear cells (PBMCs), we recovered highly purified (>99%) populations (FIG. 18). GBV-C RNA was detected in PBMCs obtained from all nine subjects with an average of 879 genome equivalents (G.E.) per 10⁴ cells (FIG. 12A). GBV-C RNA was detected in both CD4+ T cells (average 146 GE per 10⁴ cells) and CD8+ T cells (average 77 GE per 10⁴ cells) in all but two subjects. One of these subjects had GBV-C RNA only detected in CD4+ T cells while the other had GBV-C RNA present in only the CD8+ T cell population (FIG. 12A). Thus, assuming that there is only one GBV-C RNA produced per cell, less than 10% of PBMCs are infected. However, it is likely that each cell contains multiple copies of viral RNA and that the proportion of GBV-C infected PBMCs is much lower than 10%. Given the low frequency of circulating infected cells, GBV-C infection must alter TCR activation in uninfected T cells to explain the global reduction in T cell activation as observed in previous clinical studies.

Since a closely related virus HCV transmits viral RNA and proteins to bystander cells via extracellular microvesicles (EMV)(Dreux, 2012 and Dreux, 2012), the inventors hypothesized that GBV-C may utilize a similar mechanism to interact with bystander cells. To test this hypothesis, they examined EMV from the serum of GBV-C viremic subjects for the presence of GBV-C RNA. EMV purified using a commercial reagent (Exoquick) contained GBV-C RNA (FIG. 12B). Above 98% of GBV-C RNA in the serum was associated with EMV and only less than 2% of RNA was found in the leftover supernatant (FIG. 12B). Consistent with a previous study (Xiang, 1998), saline flotation gradient centrifugation of GBV-C-positive serum yielded two populations of RNA-containing particle with distinctly different densities (FIG. 21D). Viral RNA was concentrated in a low density fraction (Top; ~1.07 g/ml), consistent with LDL-associated particles, and a heavier fraction (Bottom; ~1.16 g/ml). The heavier particles had a density similar to that described for vesicles of endocytic origin (exosomes; 1.10-1.19 g/ml) (Meckes, 2011) and were precipitated by Exoquick reagent. In contrast, the lower density particles did not precipitate with Exoquick reagent suggesting microvesicles of endocytic origin are preferentially precipitated by Exoquick reagent (data not shown). Incubation of primary human CD4+ and CD8+ T cells from healthy blood donors with the EMV prepared from GBV-C viremic sera (GB+ EMV) inhibited TCR signaling, as measured by the release of IL-2 and cell surface expression of CD69 and CD25 (T cell activation markers) following TCR engagement with CD3/CD28 antibodies compared to cells incubated in EMV obtained from GBV-C non-viremic controls (GB− EMV) (FIGS. 12E-G).

GBV-C E2 Protein Inhibits TCR-Mediated Activation of CD4+ T Cells.

Figure 13:
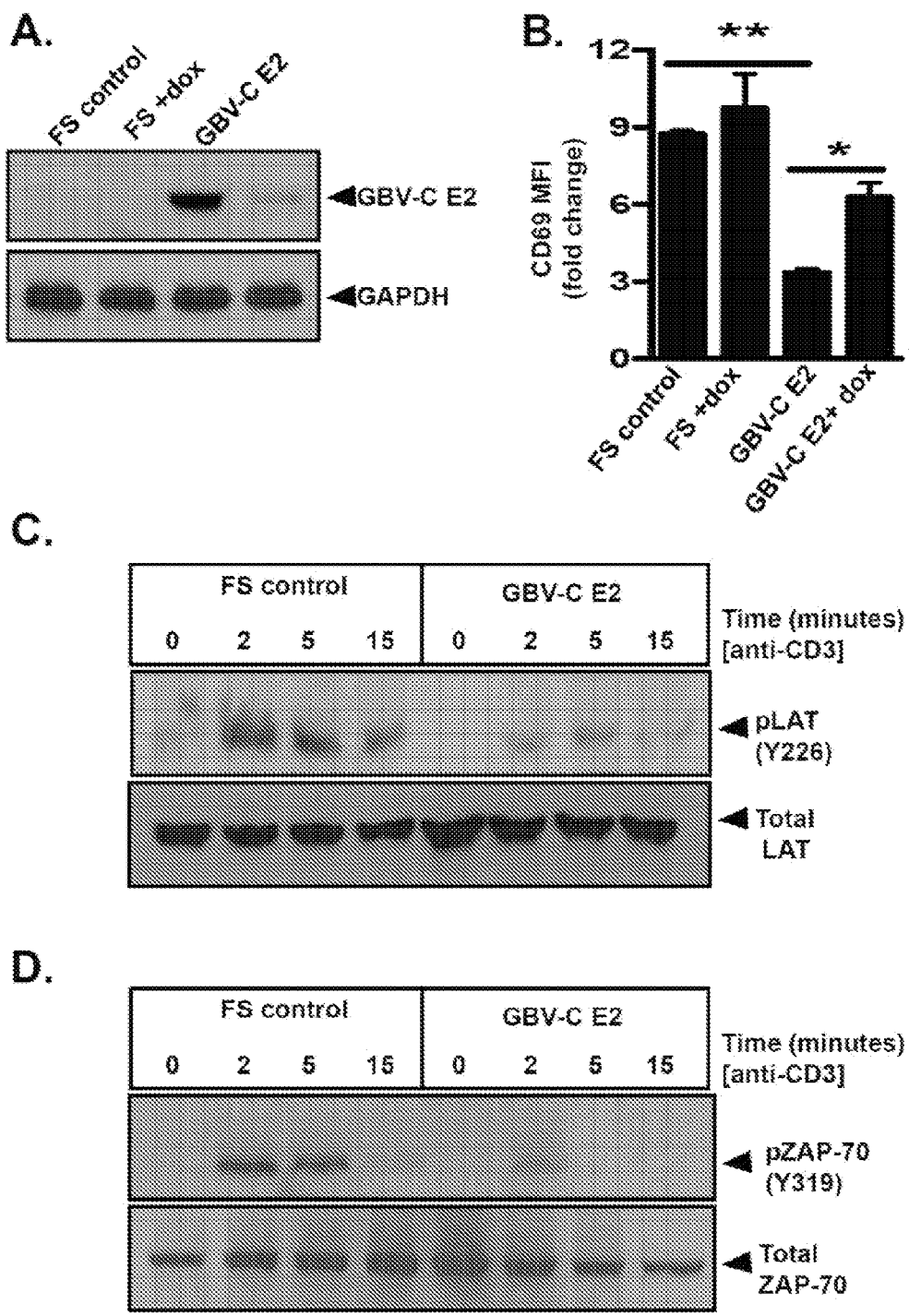
FIGS. 13A-D. GBV-C E2 protein expression inhibits T cell receptor (TCR) mediated activation of human T cells. Jurkat (tet-off) cells stably expressing GBV-C E2 protein or the same GBV-C sequence with a plus one frame shift to abolish translation (FS) were incubated with or without doxycycline (dox; 1 μg/ml) for 5 days. Dox treatment significantly reduced E2 protein expression (FIG. 13A). Twenty-four hours after TCR stimulation with CD3 and CD28 antibodies, CD69 surface expression was significantly reduced in Jurkat cells expressing E2 protein, and this was reversed by maintaining cells in doxycycline (FIG. 13B). Data represent the −fold increase in CD69 expression before and after TCR stimulation from three independent cultures. Following TCR stimulation with CD3 and CD28 antibodies, Jurkat cells expressing E2 had a reduction in phosphorylation of linker for activation of T cells (LAT.

Previous study suggested that GBV-C E2 protein inhibits T cell activation and IL-2 signaling pathways in human T cells[12]. To determine if TCR activation was altered by E2 protein, E2 RNA or both, activation was measured in tet-off Jurkat (CD4+) T cells before and following TCR stimulation with CD3/CD28 antibodies. Tet-off Jurkat cells stably expressing the GBV-C E2 protein or the GBV-C E2 sequence in which a plus one frame shift was inserted to abolish translation (FS) were incubated with or without doxycycline (1 µg/ml) for 5 days to reduce expression of GBV-C E2 (FIG. 13A). Following TCR stimulation, surface expression of CD69 (a marker for T cell activation) was significantly inhibited in E2 expressing Jurkat cells compared to the control FS cells expressing the E2 RNA sequence, and this inhibition was reversed in cells maintained in doxycycline (FIG. 13B). Thus, GBV-C E2 protein and not the E2-coding RNA was responsible for the reduced activation following TCR stimulation.

Since GBV-C E2 protein expression inhibited surface expression of CD69 following TCR stimulation (FIG. 13B), the effects of E2 protein on proximal TCR signaling pathways were assessed. Following TCR stimulation, phosphorylation of the linker for activation of T cells (LAT) (FIG. 13C, FIG. 19A) and zeta-chain-associated protein kinase (ZAP)-70 (FIG. 13D, FIG. 19B) was reduced in GBV-C E2 expressing cells compared to the FS control. This reduction in phosphorylation was due to inhibition of TCR signaling, as the total cellular LAT and ZAP-70 protein levels were not different between the E2 expressing and FS control Jurkat cells (FIG. 13C-D).

GBV-C E2 Protein Inhibits Lck Activation.

Lymphocyte specific protein tyrosine kinase (Lck) activation is required for signaling through the TCR (Davis and van der Merwe, 2011). Inactive Lck is phosphorylated at tyrosine 505 (Y505) by the C-src tyrosine kinase (Csk). Following TCR engagement, phosphorylated Y505 is dephosphorylated by CD45 tyrosine phosphatase, leading to a change in conformation and subsequent auto-phosphorylation of Lck tyrosine 394 (Y394) in trans (Davis and van der Merwe, 2011). Phosphorylated Y394 in Lck is the active form, is required for ZAP70 phosphorylation, and drives downstream signaling through the TCR pathway.

Figure 14:
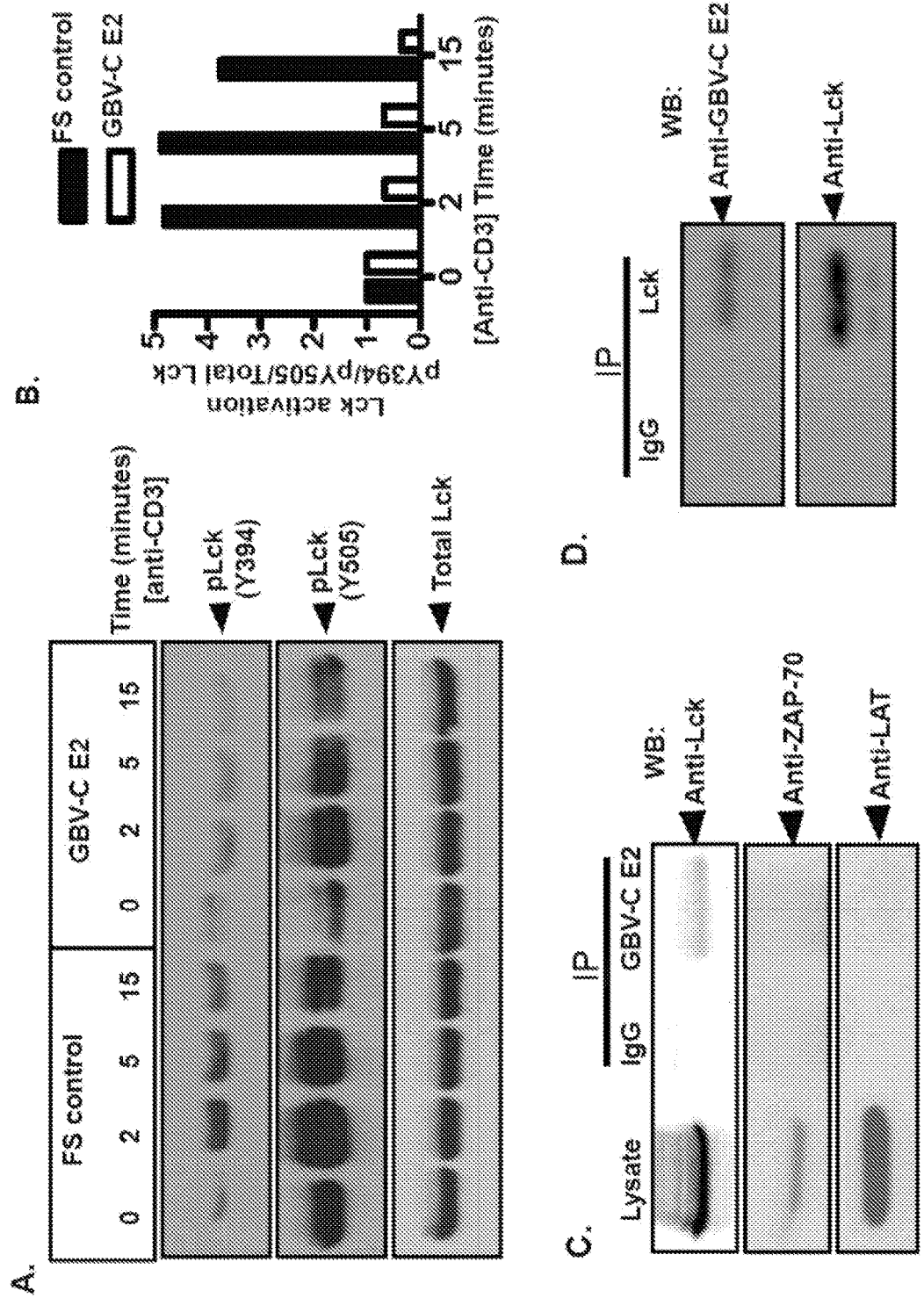
FIGS. 14A-D. GBV-C E2 protein interacts with and inhibits Lck activation. Lck activation (phosphorylation of Lck Y394) was reduced in Jurkat cells expressing GBV-C E2 protein compared to the frameshift (FS) control following TCR stimulation with CD3 antibody (A, B). Recombinant GBV-C E2-human Fc fusion protein but not human IgG precipitated Lck, but not Zap-70 or LAT from Jurkat cell lysates (C). Similarly, precipitation of Lck from Jurkat cells expressing GBV-C E2 protein also precipitated E2 protein (D). Each experiment was repeated at least three times with consistent results.

Following TCR engagement with anti-CD3, Lck activation, as measured by phosphorylation of Y394, was reduced in Jurkat cells expressing E2 protein compared to FS controls (FIGS. 14A-B). This inhibition was not due to altered Lck regulation, as CD45 and Csk expression levels were similar in both GBV-C E2 expressing cells and the FS control cells (FIGS. 20A-B). Furthermore, CD45 phosphatase activity was not altered in vitro by incubation with recombinant GBV-C E2 protein (FIG. 20C). To determine if GBV-C E2 interacted directly with Lck, recombinant GBV-C E2 protein incubated with the Jurkat cell lysate was precipitated and probed for the presence of co-precipitating signaling molecules. GBV-C E2 protein specifically co-precipitated Lck but not ZAP-70 or LAT from Jurkat cell lysate (FIG. 14C) Immunoprecipitation in the reversed order confirmed the association of GBV-C E2 and Lck as immunoprecipitation of Lck co-precipitated E2 protein from Jurkat cells expressing E2 protein (FIG. 14D).

Figure 15:
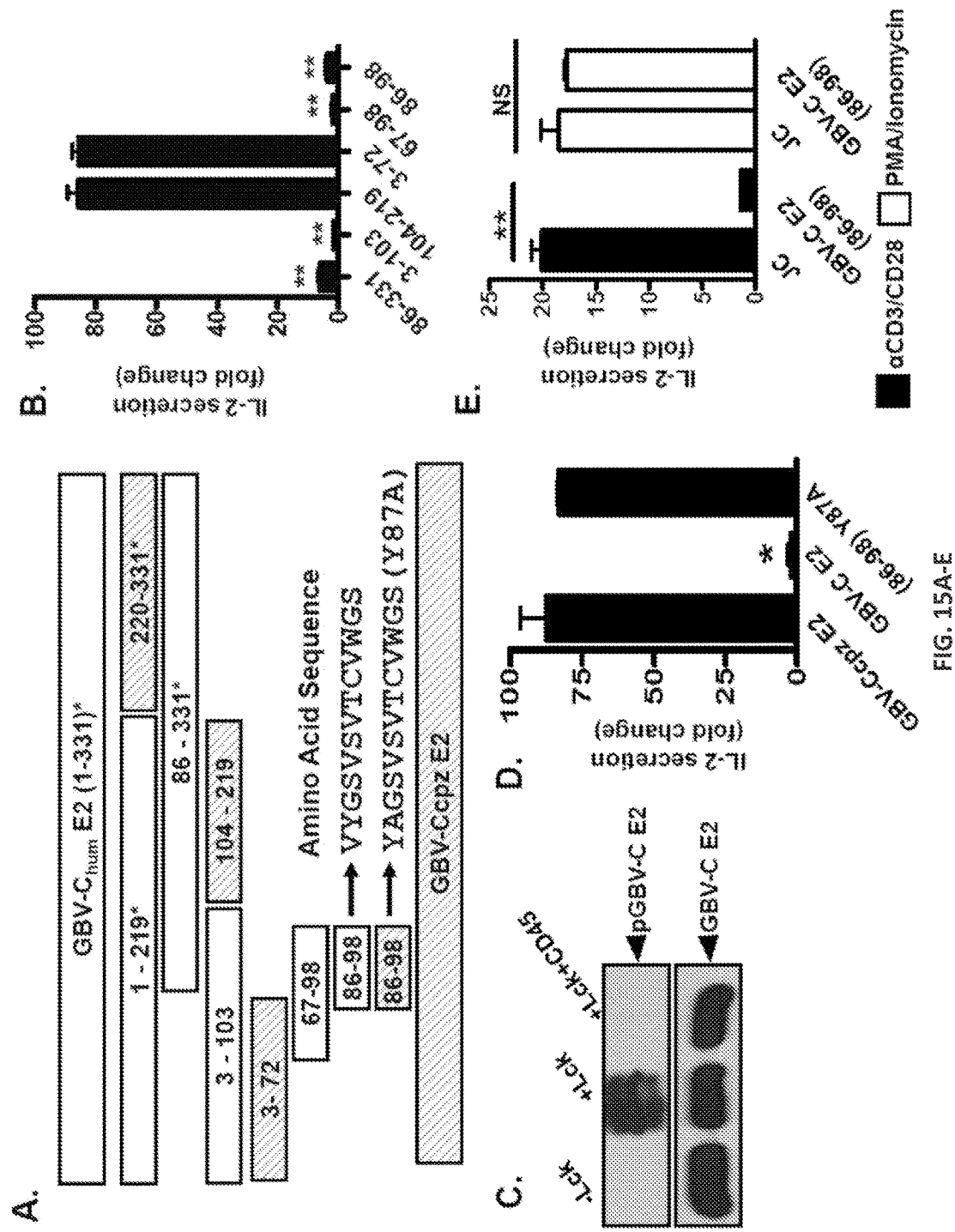
FIGS. 15A-E. Characterization of a peptide domain within GBV-C E2 that inhibits T cell receptor (TCR) signaling. Panel A illustrates Jurkat cells lines that stably expressed GBV-C E2 proteins (amino acid numbers shown). *=previously described cell lines. Shaded box represent cell lines that did not inhibit TCR signaling (FIG. 15A). IL-2 release was inhibited following TCR stimulation with CD3 and CD28 antibodies in all cell lines expressing E2 amino acids 86-98 (FIG. 15B). Recombinant E2 protein incubated with recombinant Lck demonstrated E2 tyrosine phosphorylation and when CD45 was added, E2 was dephosphorylated (FIG. 15C). TCR-induced IL-2 release was not inhibited in Jurkat cells expressing the chimpanzee GBV-C E2 protein (GBV-Ccpz) or the human E2 with a tyrosine to alanine substitution (Y87A) (FIG. 15D). Expression of E2 amino acids 86-98 did not inhibit activation by PMA (50 ng/ml) and Ionomycin (1 μg/ml) when compared to Jurkat cells without E2 (FIG. 15E). -Fold change in IL-2 release was calculated by measuring IL-2 at baseline (~5 pg/ml) and after anti-CD3/CD28 stimulation for 24 hours. Data represents average from three independent cultures. Each experiment was repeated at least three times with consistent results. *P<0.05, **P<0.01
Figure 21:
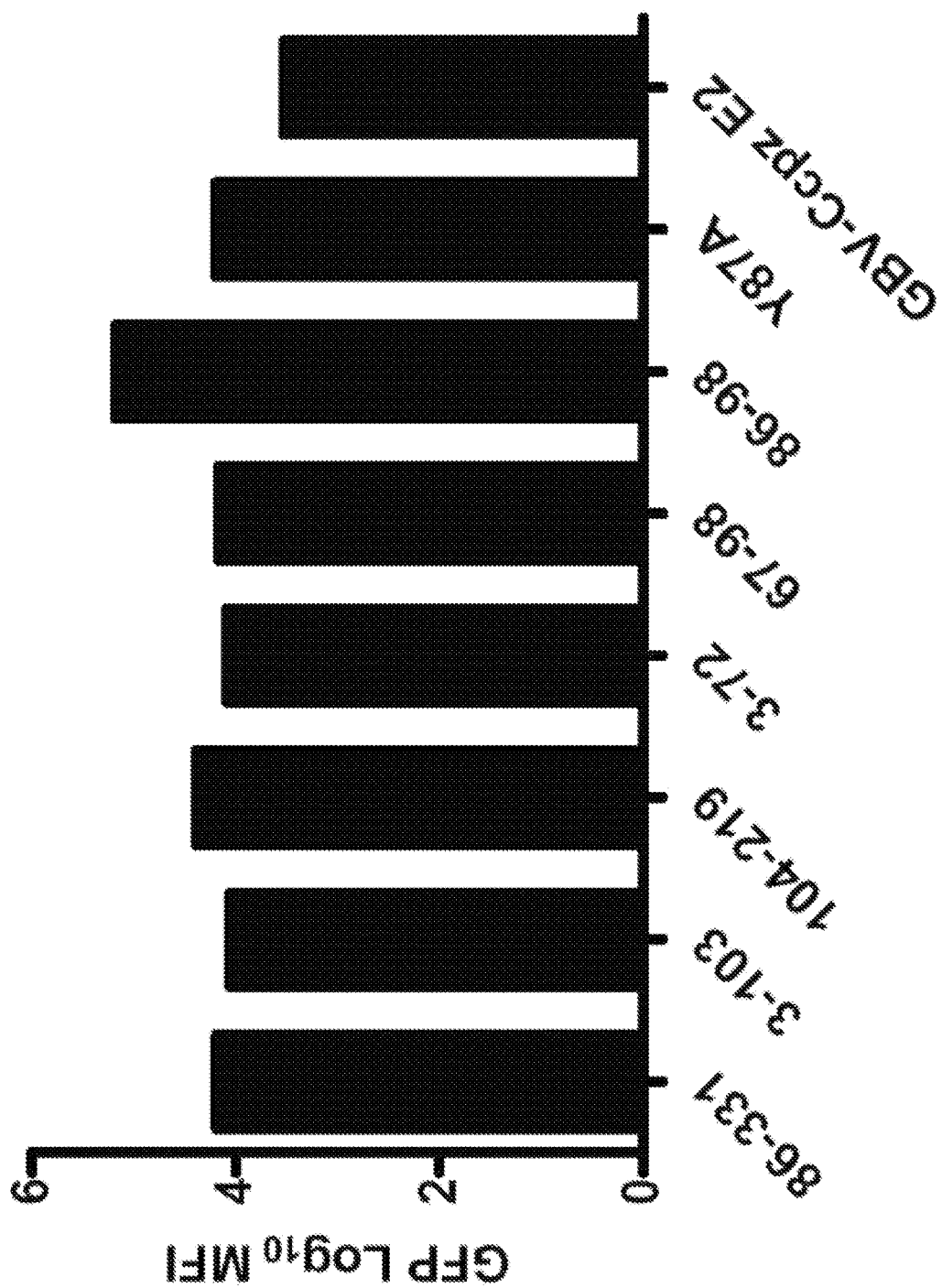
FIG. 21. GFP expression by Jurkat cell lines. Jurkat cell lines expressing human GBV-C E2 protein truncated mutants and E2 protein from chimpanzee GBV-C (GBV-$C_{cpz}$) isolate stably expressed GFP as determined by flow cytometry.

Expression of the N-terminal region 219 aa of GBV-C E2 protein is sufficient to inhibit IL-2 production following TCR stimulation (Bhattarai, 2012). To map the site(s) in the GBV-C E2 protein that mediated changes in TCR signaling, we generated a series of Jurkat cells expressing GBV-C E2 deletions (FIG. 15A). All cell lines stably expressed GFP, as demonstrated by flow cytometry (FIG. 21). Following TCR stimulation with anti-CD3/CD28, IL-2 production was blocked in all cell lines that expressed a 13 amino acid motif within GBV-C E2 (aa 86-98), but not in cell lines that expressed other regions of E2 without this motif (FIG. 15B). Utilizing kinase-specific phosphorylation substrate prediction programs, the inventors identified a tyrosine residue at position 87 (Y87) in GBV-C E2 that is predicted to be Lck (Src-kinase) target (FIG. 15A) (Xiang, 1998 and Meckes, 2011). Confirming this prediction, in vitro GBV-C E2 protein was found to be phosphorylated by Lck as demonstrated by immunoblot analysis using phospho-tyrosine specific antibodies (FIG. 15C). Similar to Lck, the GBV-C E2 protein was dephosphorylated by CD45 tyrosine phosphatase (FIG. 15C).

Figure 16:
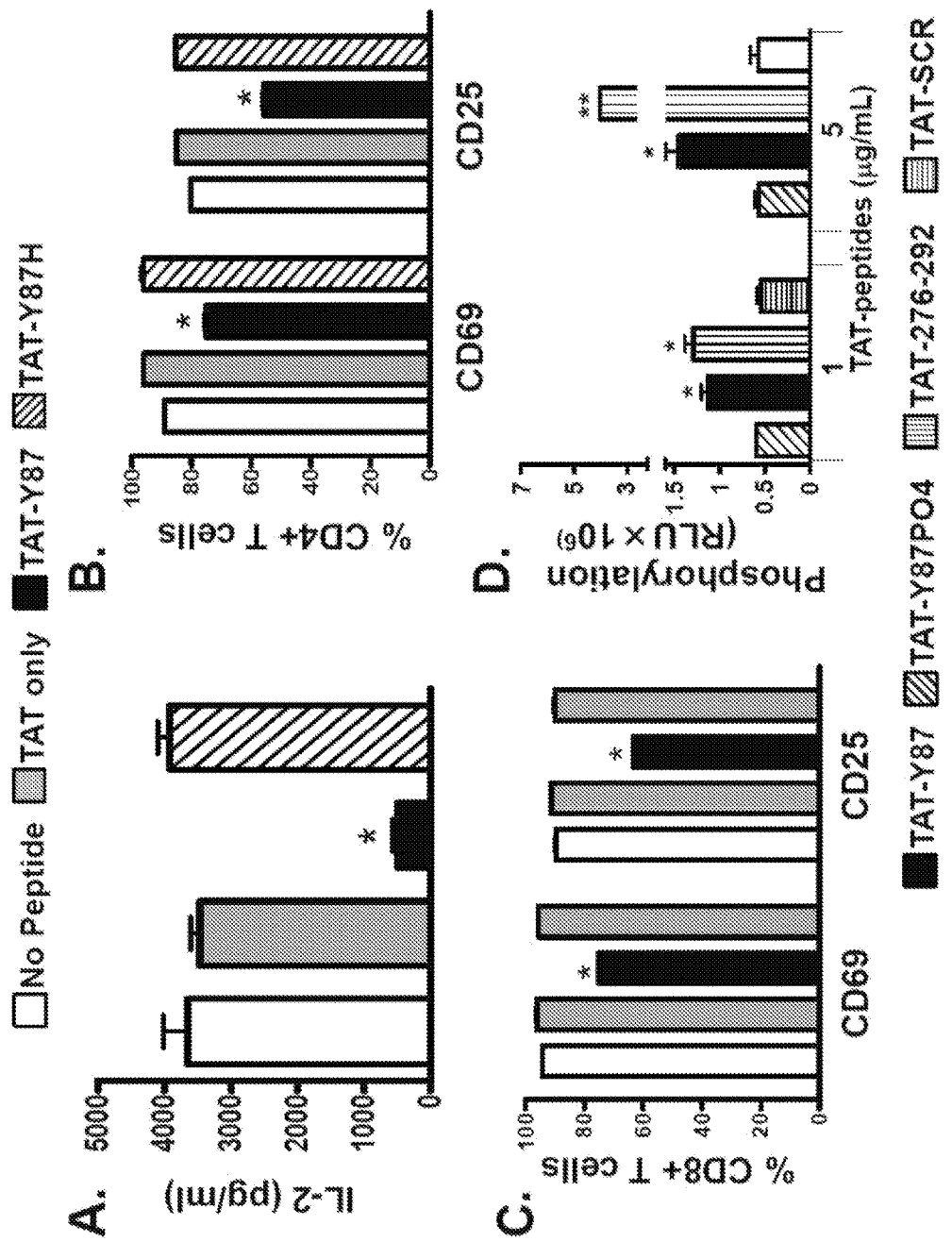
FIGS. 16A-D. Synthetic GBV-C E2 peptides inhibit TCR activation in primary human T cells. Following TCR-stimulation with CD3 and CD28 antibodies, healthy donor PBMCs incubated with GBV-C E2 86-101 peptides containing an HIV TAT protein transduction domain (TAT-Y87) had reduced IL-2 production (FIG. 16A); CD69 and CD25 expression on CD4+(FIG. 16B) and CD8+(FIG. 16C) T cells compared to no peptide, a TAT only peptide, or the 86-101 peptide that substituted a histidine for the tyrosine (TAT-Y87H). Lck mediated phosphorylation of TAT-Y87 and TAT-276-292 peptide was detected in dose-dependent manner compared to TAT-Y87 peptide synthetically phosphorylated (TAT-Y87PO4) or the TAT-276-292 peptide synthesized in a scrambled order TAT-SCR (FIG. 16D). RLU=relative luminescence units. Each experiment was repeated at least three times with consistent results. *P<0.05, *P<0.01.
Figure 23:
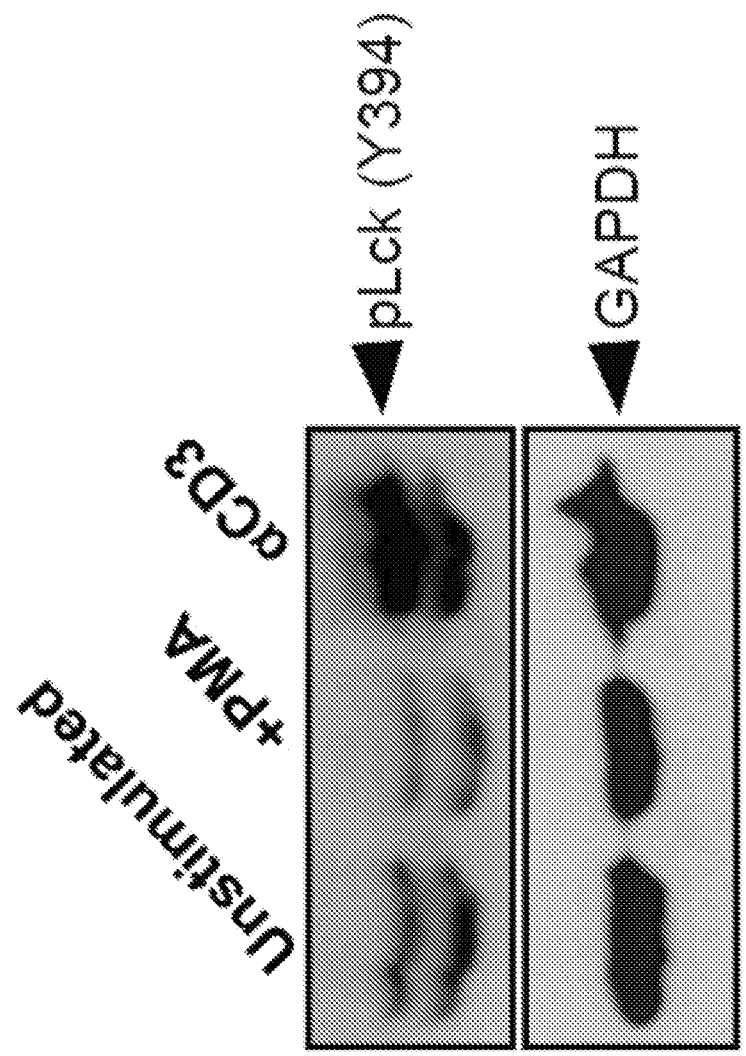
FIG. 23. Phorbol-12-myristate-13-acetate (PMA) does not induce Lck activation. Jurkat cells were either unstimulated or stimulated with PMA (50 ng/ml) or anti-CD3 (5 µg/ml) for two minutes. Lck phosphorylation (Y394) was only detected in Jurkat cells incubated with anti-CD3 but not with PMA.

The predicted Lck substrate motif within GBV-C E2 protein (aa 83-91; PQYVYGSVS (SEQ ID NO: 10)) is highly conserved and there is no sequence variation detected among 39 of the 42 complete human GBV-C isolates that represent the seven identified genotypes (FIG. 16A). The three isolates that differ do so at a single aa (Q84L or V90A), and neither of these changes altered predicted Lck phosphorylation site. In contrast, there were significant differences in this region of the E2 protein of the chimpanzee variant of GBV-C (GBV-Ccpz) sequences (83-91 aa; PRYVHGHIT; FIG. 22A). In addition, GBV-Ccpz E2 protein contained a histidine residue at position 87 (H87) instead of a tyrosine and expression of this protein in Jurkat cells did not inhibit IL-2 production following TCR stimulation (FIG. 15D). Furthermore, mutation of the tyrosine (Y87) in the human GBV-C E2 (aa 86-98) peptide to an alanine (Y87A) reversed the inhibition of TCR signaling as measured by IL-2 release (FIG. 15D). To further assess the specificity of GBV-C E2 protein for TCR signaling inhibition, control Jurkat cells or Jurkat cells expressing the human GBV-C E2 (86-98 aa) were stimulated with phorbol-12-myristate-13-acetate (PMA) and ionomycin. PMA-ionomycin stimulation does not activate Lck (FIG. 23) and PMA-ionomycin induced T cell activation as measured by IL-2 release was not inhibited by the GBV-C E2 (aa 86-98) peptide (FIG. 15E). These data suggest that GBV-C E2 protein specifically inhibits TCR signaling pathways at the level of Lck activation.

To confirm that the predicted Lck substrate motif within GBV-C E2 protein was sufficient to inhibit TCR-mediated signaling in primary human CD4+ and CD8+ T cells, the inventors compared the inhibitory capacities of a series of synthetic peptides with native or mutated (Y87H) sequences in the region of interest (residues 86-101). The peptides were biotinylated to monitor cell uptake and included an N-terminal HIV Tat protein transduction domain (TAT) to promote internalization by target cells. A TAT only synthetic peptide served as a negative control. All three biotinylated peptides were internalized by healthy human PBMCs, as demonstrated by flow cytometry (FIGS. 24A-D). Following TCR stimulation, IL-2 production by PBMCs was inhibited in cells incubated with the TAT-Y87 peptide, but not in those incubated with either the TAT-Y87H or the TAT control peptides (FIG. 16A). Consistent with this selective inhibition of IL-2 production, surface expression of T cell activation markers (CD69 and CD25) was significantly reduced in primary human CD4+ and CD8+ T cells incubated with the TAT-Y87 peptide compared to mutant or control peptide (FIGS. 16B-C). In addition, the TAT-Y87 peptide served as an Lck substrate in vitro, and was phosphorylated by Lck in a dose-dependent manner (FIG. 16D). In contrast, a synthetically phosphorylated Y87 peptide (TAT-Y87PO4) did not serve as an Lck substrate (FIG. 16D), supporting the hypothesis that this region on the GBV-C E2 protein competes for phosphorylation with Lck. There is one additional predicted Lck substrate motif within the GBV-C E2 protein (aa281-289; TGGFYEPLV; FIG. 22B). A synthetic peptide containing this motif (TAT-276-292) also served as a Lck substrate in vitro compared to a control peptide (TAT-SCR) which was synthesized with the same amino acids as the TAT-276-292 in a scrambled order to disrupt predicted Lck substrate sequence (FIG. 16D). Although TAT-276-292 peptide served as a Lck substrate in vitro, expression of this region of E2 protein did not inhibit TCR-induced IL-2 production (Bhattarai, 2012).

GBV-C E2 Protein Inhibits T Cell Activation in Bystander Cells.

Figure 17:
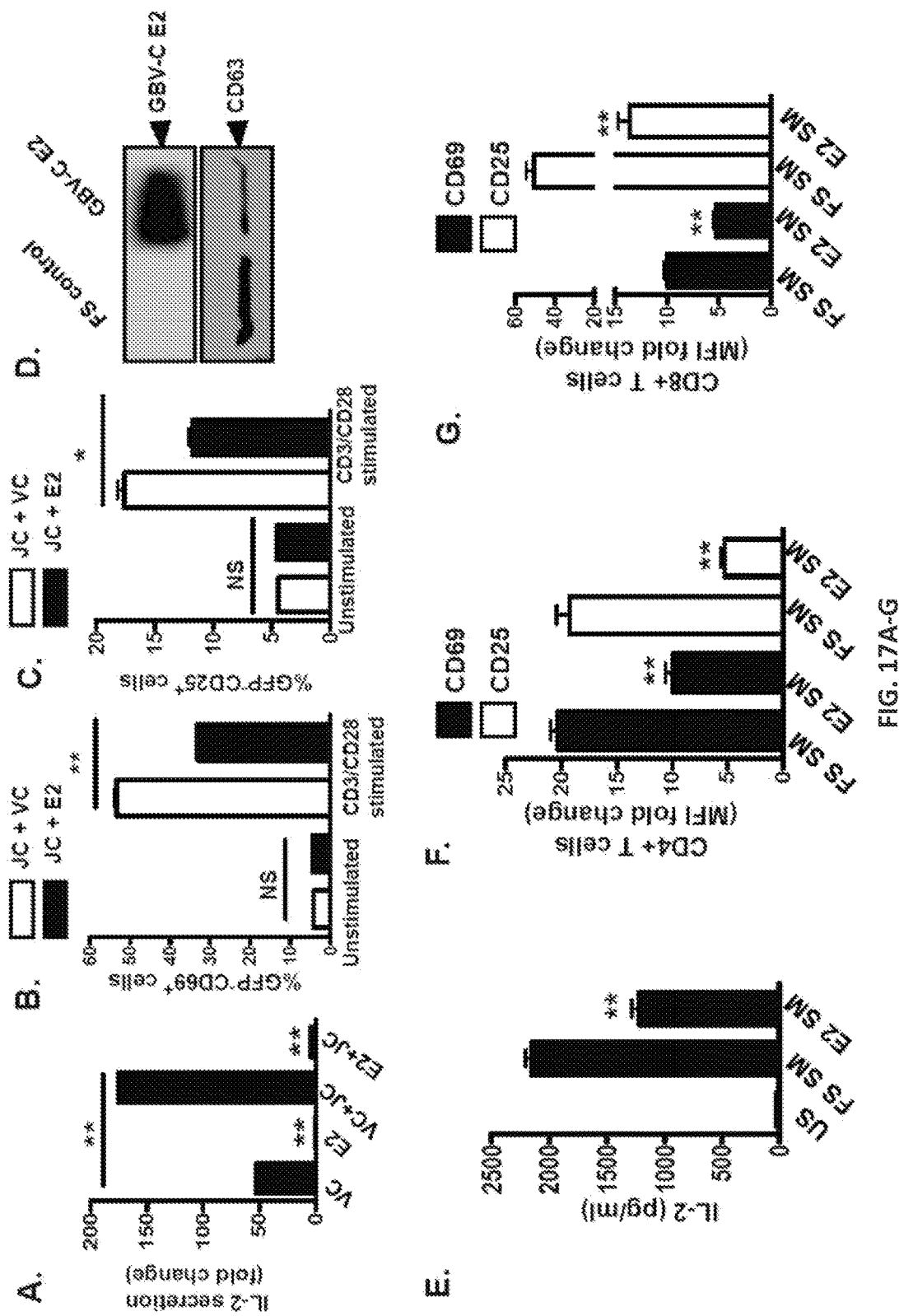
FIGS. 17A-G. GBV-C E2 protein inhibits T cell receptor (TCR) signaling in bystander cells. Following TCR stimulation with CD3 and CD28 antibodies, IL-2 release (FIG. 17A), surface expression of CD69 (FIG. 17B) and CD25

Since expression of GBV-C E2 protein alone inhibited TCR signaling (FIGS. 13A-D), the inventors hypothesized that E2-expressing cells may inhibit TCR signaling in bystander cells contributing to global reduction in TCR signaling observed in GBV-C infected subjects (Bhattarai et al., 2012; Stapleton, 2009; Maidana-Giret, 2009 and Stapleton, 2012). To test this hypothesis, GBV-C E2-expressing (GFP-positive) or vector control Jurkat cells (VC; also GFP-positive) were co-cultured with Jurkat cells not expressing GFP. Following TCR engagement, IL-2 secretion and surface expression of the activation markers CD69 and CD25 were significantly inhibited in the bystander Jurkat cells co-cultured with GBV-C E2 expressing cells compared to bystander cells co-cultured with the vector control cells (FIGS. 17A-C). Since, extracellular microvesicles (EMV) purified from the serum of GBV-C infected subjects inhibited TCR signaling when incubated with primary human T cells (FIGS. 12A-F), the inventors tested if E2 protein may get released in EMV from E2 expressing cells. GBV-C E2 protein was detected in EMV purified from E2-expressing Jurkat cell culture supernatant but not the FS supernatant fluid (FIG. 17D). These EMV also contained CD63 suggesting that they were of endocytic origin (Meckes, 2011) (FIG. 17D) consistent with the EMV obtained from GBV-C infected human serum (FIGS. 12B-C). To determine if GBV-C E2 protein released from Jurkat cells reduced TCR signaling in bystander T cells, primary human CD4+ and CD8+ T cells from healthy blood donors were incubated with EMV purified from E2-expressing Jurkat cells (E2 EMV) or FS control Jurkat cells (FS EMV). Following TCR engagement, IL-2 release and cell surface expression of CD69 and CD25 was significantly reduced in cells incubated with E2 EMV compared to cells incubated with FS EMV (FIGS. 12E-G).

Example 5

Discussion

GBV-C is an RNA virus that replicates only in the host cell cytoplasm and like the related HCV, it is capable of causing persistent human infection. Among HIV-infected people, persistent GBV-C co-infection is associated with reduced T cell activation and inhibition of IL-2 signaling (Rydze, et al., 2012; Bhattarai et al., 2012; Stapleton, 2009; Maidana-Giret, 2009 and Stapleton, 2012). The IL-2 signaling defect is due, at least in part, to effects of the envelope glycoprotein E2 (Bhattarai, 2012). The effects of GBV-C on T cell activation and IL-2 signaling may contribute to viral persistence (Bhattarai and Stapleton, 2012). In addition, there is little evidence that antibodies to GBV-C proteins develop during viremia, suggesting an impairment in B cell function which may reflect altered antigen presentation (Stapleton et al., 2011). Although clinical studies demonstrate an association between GBV-C infection and a global reduction in T cell activation (Bhattarai et al., 2012, Maidana-Giret, 2009 and Stapleton, 2012), only a small proportion of T cells contained viral genomes (FIG. 11A). Thus, the virus and viral proteins contained in extracellular microvesicles (EMV), or virus-infected cells must interact with and inhibit activation of uninfected bystander T cells.

In this study we demonstrate that extracellular microvesicles (EMV) present in the serum of GBV-C infected subjects and EMV released by E2-expressing Jurkat cells inhibit TCR signaling in primary human T cells. This is accomplished by reducing the activation of Lck, the proximal tyrosine kinase phosphorylated in the TCR signaling cascade. The data are consistent with the transfer of GBV-C E2 protein within virus particles or in EMV to bystander cells with resultant TCR-signaling inhibition. Since the average GBV-C RNA concentration in infected humans is greater than 1×10 (Stapleton, 2003) genome copies/mL of plasma and the virus is produced by T cells (Rydze, et al., 2012), lymphoid tissue is constantly exposed to high concentrations of GBV-C E2 protein in infected humans.

Synthetic peptides containing only one of the two predicted Lck substrate motif inhibited TCR signaling in the CD4+ T cell line and in primary human CD4+ and CD8+ T cells (Y87). Although the tyrosine at aa 285 was phosphorylated by Lck in vitro (FIG. 16D), this region of E2 did not inhibit TCR-mediated activation (Bhattarai et al., 2012). This may be due to inaccessibility of this region of E2 to Lck, as the Y285 is not likely to be exposed on the surface of the protein based on structural models of the related HCV E2 protein (Krey, 2010). This also suggests that not all predicted tyrosine kinase substrate motifs on viral structural proteins will display functional activity.

In addition to the two predicted Lck phosphorylation substrate motifs (aa 83-91 and 281-289; FIG. 22A, 5B), GBV-C E2 protein also contains two well conserved Src homology domain 3 (SH3) binding domains (PXXP; aa 48-51 and 257-260; FIGS. 22C-D). Although, GBV-C E2 protein interacted with Lck (FIGS. 14C-D) most likely through interactions between SH3 binding domain on GBV-C E2 protein and SH3 domain present on Lck, these two SH3 binding regions were not required for TCR signaling inhibition as expression of amino acids (3-72) and (220-331) of E2 did not inhibit IL-2 release following TCR activation (FIG. 15B) (Bhattarai, et al., 2012). However, it is possible that either these SH3 binding domains may contribute to inhibition of Lck activation in the setting of natural infection.

The predicted Lck substrate motif (aa 83-91) that inhibits TCR signaling is conserved in all human GBV-C (GBV-$C_{hum}$) E2 protein studied, but is not present in the E2 protein from chimpanzee GBV-C (GBV-$C_{cpz}$) isolates (FIG. 22A) and the expression of the GBV-Ccpz E2 protein did not inhibit TCR signaling (FIG. 15D). Based on this observation, it is tempting to speculate that since immune reactivity of lymphocytes from chimpanzee is significantly lower than humans (Soto et al., 2010), there is less selective pressure for GBV-Ccpz to inhibit TCR signaling for replication. Furthermore, mutation of the conserved tyrosine residue reversed the inhibitory effects of human GBV-C E2 protein (FIGS. 15D, 16A) and Lck phosphorylated GBV-C E2 and the synthetic peptide (Y87) in vitro (FIGS. 15C, 16D). These data demonstrate that the viral envelope glycoprotein is a substrate for Lck and since CD45 dephosphorylated E2 protein (FIG. 15C), phosphorylation of GBV-C E2 may be regulated in the same manner as Lck phosphorylation.

Although GBV-C E2 inhibited TCR-mediated activation compared to control cells when stimulated with anti-CD3/CD28, there were no significant differences in unstimulated cells or cells stimulated with PMA and ionomycin (FIG. 15E) suggesting the inhibition of TCR signaling by GBV-C E2 is not absolute and specifically due to inhibition of Lck activation. Thus, GBV-C infection although affects global T cell activation, the virus does not create a state of severe immune suppression resulting in clinical disease (Bhattarai and Stapleton, 2012).

In summary, the GBV-C structural protein E2 inhibits TCR-mediated T cell activation by interacting with Lck and competing for Lck phosphorylation. The inhibition is mediated by either the expression of GBV-C E2 protein within cells, or by the transfer of E2 to bystander cells as part of the virus particle or within microvesicular particles. These data identify a novel mechanism by which a viral structural protein interferes with tyrosine kinase function resulting in global inhibition of T cell activation and support a proposed model for global alteration of T cell activation during GBV-C infection (FIGS. 25A-C). Recently, a non-biased study of interactions between 70 viral proteins from 30 different viruses and host cells identified specific viral protein interactions with 579 different host proteins. More than half of the host proteins are involved in signal transduction pathways (Pichlmair, 2012). Since there are numerous predicted kinase binding and substrate sites encoded in viral structural proteins, it is tempting to speculate that the mechanism by which GBV-C inhibits Lck may also apply to other host cell signaling processes, and illustrate the potential for regulation of host cell function by virus particles. These interactions may influence viral persistence and viral pathogenesis. Identification of the interactions between viral structural proteins and host cells may facilitate the design of novel and specific antiviral therapies and vaccines.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,554,101
U.S. Pat. No. 4,683,202
U.S. Pat. No. 4,879,236
U.S. Pat. No. 5,440,013
U.S. Pat. No. 5,446,128
U.S. Pat. No. 5,475,085
U.S. Pat. No. 5,618,914
U.S. Pat. No. 5,650,298
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,871,986
U.S. Pat. No. 5,874,563
U.S. Pat. No. 5,925,565
U.S. Pat. No. 5,928,906
U.S. Pat. No. 5,929,237
U.S. Pat. No. 5,935,819
U.S. Pat. No. 6,261,569
PCT Application WO 01/77157
Abrams et al., *N Engl. J. Med.,* 361:1548-1559, 2009.
Angel et al., *Cell,* 49:729, 1987b.
Angel et al., *Mol. Cell. Biol.,* 7:2256, 1987a.
Ausubel et al., *Current Protocols in Molecular Biology,* Greene Publishing Associates and Wiley Interscience, N.Y., 1994.
Baichwal and Sugden, In: *Gene Transfer,* Kucherlapati (Ed.), NY, Plenum Press, 117-148, 1986.
Banerji et al., *Cell,* 27(2 Pt 1):299-308, 1981.
Banerji et al., *Cell,* 33(3):729-740, 1983.
Barany and Merrifield, In: *The Peptides,* Gross and Meienhofer (Eds.), Academic Press, NY, 1-284, 1979.
Berkhout et al., *Cell,* 59:273-282, 1989.
Bhattarai and Stapleton, *Trends Microbiol* 20, 124-130, 2012.
Bhattarai et al., *J Infect Dis* 206, 1469-1472, 2012.
Bhattarai, et al., *J Immunol* 189, 2211-2216, 2012.
Blanar et al., *EMBO J.,* 8:1139, 1989.
Boshart et al., *Cell,* 41:521, 1985.
Bosze et al., *EMBO J.,* 5(7):1615-1623, 1986.
Braddock et al., *Cell,* 58:269, 1989.

Camargo et al., *J. Immunol.*, 182:171-182, 2009.
Campo et al., *Nature*, 303:77, 1983.
Capaldi et al., *Biochem. Biophys. Res. Comm.*, 74(2):425-433, 1977.
Carbonelli et al., *FEMS Microbiol. Lett.*, 177(1):75-82, 1999.
Celander et al., *J. Virology*, 62:1314, 1988.
Chandler et al., *Cell*, 33:489, 1983.
Chandler et al., *Proc Natl. Acad. Sci. USA*, 94(8):3569-601, 1997.
Chatterjee et al., *Proc Natl. Acad Sci. U.S.A.*, 86:9114, 1989.
Chen and Okayama, *Mol. Cell Biol.*, 7:2745-2752, 1987.
Cheng et al., *Immunol. Rev.*, 241:63-76, 2011.
Cocea, *Biotechniques*, 23(5):814-6, 1997.
Cohen et al., *J. Cell. Physiol.*, 5:75, 1987.
Costa et al., *Mol. Cell. Biol.*, 8:81, 1988.
Cripe et al., *EMBO J.*, 6:3745, 1987.
Dandolo et al., *J. Virology*, 47:55-64, 1983.
Davis and van der Merwe, *Trends Immunol* 32, 1-5, 2011.
De Villiers et al., *Nature*, 312(5991):242-246, 1984.
Deschamps et al., *Science*, 230:1174-1177, 1985.
Dreux, *Cell Host Microbe* 12, 558-570, 2012.
Edbrooke et al., *Mol. Cell. Biol.*, 9:1908, 1989.
Edlund et al., *Science*, 230:912-916, 1985.
Fechheimer et al., *Proc. Nat'l Acad. Sci. USA*, 84:8463-8467, 1987.
Fogeda et al., *J. ViroL* 73:4052-4061, 1999.
Fortis et al., *AIDS Res. Hum. Retroviruses*, 18:491-499, 2002.
Fraley et al., *Proc. Natl. Acad. Sci. USA*, 76:3348-3352, 1979.
Freshney, In: *Animal Cell Culture: a Practical Approach*, Second Edition, Oxford/NY, IRL Press, Oxford University Press, 1992.
Fujita et al., *Cell*, 49:357, 1987.
George et al., *J. Infect. Dis.*, 193:451-454, 2006.
George et al., *Virology*, 316:191-201, 2003.
Ghosh and Bachhawat, In: *Liver diseases, targeted diagnosis and therapy using specific receptors and ligands*, (Wu G, Wu C ed.), NY, Marcel Dekker, 87-104, 1991.
Gilles et al., *Cell*, 33:717, 1983.
Giorgi et al., *J. Infect. Dis.*, 179:859-870, 1999.
Gloss et al., *EMBO J.*, 6:3735, 1987.
Godbout et al., *Mol. Cell. Biol.*, 8:1169, 1988.
Goodbourn et al., *Cell*, 45:601, 1986.
Gopal, *Mol. Cell Biol.*, 5:1188-1190, 1985.
Gossen et al., *Proc. Natl. Acad. Sci. USA*, 89:5547-5551, 1992.
Gossen et al., *Science*, 268:1766-69, 1995.
Graham and Van Der Eb, *Virology*, 52:456-467, 1973.
Green et al., *Immunol. Rev.*, 193:70-81, 2003.
Greene et al., *Immunology Today*, 10:272, 1989
Harland and Weintraub, *J. Cell Biol.*, 101:1094-1099, 1985.
Hazenberg et al., *AIDS*, 17:1881-1888, 2003.
Heaton et al., *Cancer Res.*, 53:2597-2602, 1993.
Hen et al., *Nature*, 321:249, 1986.
Hensel et al., *Lymphokine Res.*, 8:347, 1989.
Heringlake et al., *J. Infect. Dis.*, 177:1723-1726, 1998.
Hirochika et al., *J. Virol.*, 61:2599, 1987.
Holbrook et al., *Virology*, 157:211, 1987.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imler et al., *Mol. Cell. Biol*, 7:2558, 1987.
Jakobovits et al., *Mol. Cell. Biol.*, 8:2555, 1988.
Jaynes et al., *Mol. Cell. Biol.*, 8:62, 1988.
Johannesson et al. *J. Med. Chem.*, 42(22):4524-4537, 1999.
Johannesson et al., *J. Med. Chem.*, 42:601-608, 1999.
Johnson et al., In: *Biotechnology And Pharmacy*, Pezzuto et al., (Eds.), Chapman and Hall, NY, 1993.
Johnson et al., *Mol. Cell. Biol.*, 9:3393, 1989.
Kaneda et al., *Science*, 243:375-378, 1989.
Karin et al., *Mol. Cell. Biol.*, 7:606, 1987.
Katinka et al., *Cell*, 20:393, 1980.
Kawamoto et al., *Mol. Cell. Biol.*, 8:267, 1988.
Kiledjian et al., *Mol. Cell. Biol.*, 8:145, 1988.
Kim et al., *Cytokine Growth Factor Rev.*, 17:349-366, 2006.
Kinter et al., *J. Immunol.*, 154:2448-2459, 1995.
Klamut et al., *Mol. Cell. Biol.*, 10:193, 1990.
Koch et al., *Mol. Cell. Biol.*, 9:303, 1989.
Koedel et al., *J. Virol.*, 85(14):7037-47, 2011.
Kraus et al., *FEBS Lett.*, 428(3):165-70, 1998.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kyte and Doolittle, *J. Mol. Biol.*, 157:105-132, 1982.
Krey, PLoS *Pathog* 6, e1000762, 2010.
Lareyre, et al., *J. Bio. Chem.*, 274(12):8282-90, 1999.
Larsen et al., *Proc Natl. Acad. Sci. USA.*, 83:8283, 1986.
Laskus et al., *J. Virol.*, 72:3072-3075. 1998.
Laspia et al., *Cell*, 59:283, 1989.
Latimer et al., *Mol. Cell. Biol.*, 10:760, 1990.
Leary et al., *J. Med. Virol.*, 48:60-67. 1996.
Lee et al., *DNA Cell Biol.*, 16(11):1267-1275, 1997.
Lee et al., *Nature*, 294:228, 1981.
Lee et al., *Nucleic Acids Res.*, 12:4191-206, 1984.
Lefrere et al., *J. Med. Virol.*, 59:32-37, 1999.
Levenson et al., *Hum. Gene Ther.*, 9(8):1233-6, 1998.
Levinson et al., *Nature*, 295:79, 1982.
Lin and Leonard, *Cytokine Growth Factor Rev.*, 8:313-332, 1997.
Luria et al., *EMBO J.*, 6:3307, 1987.
Lusky et al., *Mol. Cell. Biol.* 3:1108, 1983.
Maidana-Giret et al., *AIDS*, 23:2277-2287, 2009.
Maniatis, et al., Molecular Cloning, A Laboratory Manual, Cold Spring Harbor Press, Cold Spring Harbor, N.Y., 1988.
Maniatis, et al., Molecular Cloning, A Laboratory Manual, Cold Spring Harbor Press, Cold Spring Harbor, N.Y., 1989.
Masciopinto, *Eur J Immunol* 34, 2834-2842, 2004.
McLinden et al., *J. Virol.*, 80:12131-12140, 2006.
McNeall et al., *Gene*, 76:81, 1989.
Meckes, *J Virol* 85, 12844-12854, 2011.
Merrifield, *Science*, 232(4748):341-347, 1986.
Miksicek et al., *Cell*, 46:203, 1986.
Mohr and Stapleton, *J. Viral Hepat.*, 16:757-768, 2009.
Mohr et al., *J. Immunol.*, 185:4496-4505, 2010.
Moreau et al., *Nucl. Acids Res.*, 9:6047, 1981.
Morgan et al., *Science*, 193:1007-1008, 1976.
Muesing et al., *Cell*, 48:691, 1987.
Nattermann et al., *AIDS*, 17:1457-1462, 2003.
Nel, *J. Allergy Clin. Immunol.*, 109:758-770, 2002.
Nicolas and Rubenstein, In: *Vectors: A survey of molecular cloning vectors and their uses*, Rodriguez and Denhardt (eds.), Stoneham: Butterworth, 493-513, 1988.
Nicolau and Sene, *Biochim. Biophys. Acta*, 721:185-190, 1982.

Nomoto et al., *Gene*, 236(2):259-271, 1999.
Nunnari et al., *Ann. Intern. Med.*, 139:26-30, 2003.
Ondek et al., *EMBO J.*, 6:1017, 1987.
Palmiter et al., *Nature*, 300:611, 1982.
Pech et al., *Mol. Cell. Biol.*, 9:396, 1989.
Pelletier and Sonenberg, *Nature*, 334(6180):320-325, 1988.
Pessoa et al., *Hepatol.*, 27:877-880, 1998.
Pett. *Curr. Opin. HIV AIDS*, 4:188-193, 2009.
Pichlmair, *Nature* 487, 486-490, 2012.
Pinkert et al., *Genes and Dev.*, 1:268, 1987.
Ponta et al., *Proc. Natl. Acad. Sci. USA*, 82:1020, 1985.
Porter et al., *AIDS*, 23:2015-2019, 2009.
Porton et al., *Mol. Cell. Biol.*, 10:1076, 1990.
Potter et al., *Proc. Nat'l Acad. Sci. USA*, 81:7161-7165, 1984.
Quinn et al., *Mol. Cell. Biol.*, 9:4713, 1989.
Redondo et al., *Science*, 247:1225, 1990.
Remington's Pharmaceutical Sciences, 15th Ed., 33:624-652, 1990.
Remington's Pharmaceutical Sciences, 18th Ed. Mack Printing Company, 1389-1404, 1990,
Rey et al., *Eur. J. Clin. Microbiol. Infect. Dis.*, 19:721-724, 2000.
Ridgeway, In: *Vectors: A survey of molecular cloning vectors and their uses*, Rodriguez and Denhardt (Eds.), Stoneham:Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rosen et al., *Cell*, 41:813, 1988.
Rydze, et al., *Antivir Ther* 17, 1271-1279, 2012.
Sakai et al., *Genes and Dev.*, 2:1144, 1988.
Sambrook et al., In: *Molecular Cloning: A Laboratory Manual*, Vol. 1, Cold Spring Harbor Laboratory Press, Cold Spring Harbor, N.Y., 7(7)19-17.29, 1989.
Satake et al., *J. Virology*, 62:970, 1988.
Schaffner et al., *J. Mol. Biol.*, 201:81, 1988.
Schwarze-Zander et al., *Antivir. Ther.*, 15:745-752, 2010.
Searle et al., *Mol. Cell. Biol.*, 5:1480, 1985.
Seipp et al., *J. Hepatol.*, 30:570-579, 1999.
Sereti et al., *AIDS*, 15:1765-1775, 2001.
Sherman et al., *Mol. Cell. Biol.*, 9:50, 1989.
Shimizu, *J. Virol.*, 73:8411-8414, 1999.
Simons et al., *J. Virol.*, 70:6126-6135. 1996.
Simons et al., *Nature Med.*, 1:564-569, 1995a.
Simons et al., *Proc. Natl. Acad. Sci. USA*, 92:3401-3405, 1995b.
Sodora and Silvestri, *AIDS*, 22:439-446, 2008.
Spalholz et al., *Cell*, 42:183, 1985.
Stapleton, *PLoS One* 7, e50563, 2012.
Stapleton et al., *AIDS*, 23:605-610, 2009.
Stapleton et al., *J Gen. Virol.*, 92:233-246, 2011.
Stapleton, *Semin. Liver Dis.*, 23:137-148, 2003.
Stewart and Young, In: *Solid Phase Peptide Synthesis*, $2^{nd}$ Ed., Pierce Chemical Co., 1984.
Stuart et al., *Nature*, 317:828, 1985.
Takebe et al., *Mol. Cell. Biol.*, 8:466, 1988.
Tam et al., *J. Am. Chem. Soc.*, 105:6442, 1983.
Tavernier et al., *Nature*, 301:634, 1983.
Taylor et al., *J. Biol. Chem.*, 264:15160, 1989.
Temin, In: *Gene Transfer*, Kucherlapati (ed.), NY: Plenum Press, 149-188, 1986.
Thiesen et al., *J. Virology*, 62:614, 1988.
Tillmann et al., *N. Engl. J. Med.*, 345:715-724, 2001.
Toyoda et al., *J Acquir. Immune Defic. Syndr. Hum. Retrovirol.*, 17:209-213, 1998.
Tronche et al., *Mol. Biol. Med.*, 7:173, 1990.
Tur-Kaspa et al., *Mol. Cell Biol.*, 6:716-718, 1986.
Tyndell et al., *Nuc. Acids. Res.*, 9:6231, 1981.
Vasseur et al., *Proc Natl. Acad. Sci. USA*, 77:1068, 1980.
Vita et al., *Biopolymers*, 47:93-100, 1998.
Weber et al., *Cell*, 36:983, 1984.
Weinberger et al. *Mol. Cell. Biol.*, 8:988, 1984.
Weisshoff et al., *Eur. J. Biochem.*, 259(3):776-788, 1999.
Williams et al., *N. Engl. J. Med.*, 350:981-990, 2004.
Wu and Wu, *Biochem.*, 27:887-892, 1988.
Wu and Wu, *J. Biol. Chem.*, 262:4429-4432, 1987.
Wu et al., *Biochem. Biophys. Res. Commun.*, 233(1):221-6, 1997.
Wu et al., *J Med. Virol.*, 52:83-85. 1997.
Xiang, *J Virol* 72, 2738-2744, 1998.
Xiang et al., *J. Viral Hepat.*, 6:S16-S22, 1999.
Xiang et al., *N Engl. J. Med.*, 345:707-714, 2001.
Xiang et al., *Proc. Natl. Acad. Sci USA*, 103:15570-15575, 2006.
Yang et al., *Proc. Natl. Acad. Sci USA*, 87:9568-9572, 1990.
Yeo et al., *Ann. Intern. Med.*, 132:959-963, 2000.
Yutzey et al. *Mol. Cell. BioL*, 9:1397, 1989.

---

What is claimed is:

1. A method of inhibiting immune cell activation comprising administering to a mammalian subject in need thereof a GBV-C E2 peptide or polypeptide, said peptide or polypeptide comprising SEQ ID NO: 8 and no more than 250 consecutive residues of GBV-C E2.

2. The method of claim 1, wherein said peptide or polypeptide comprises 232 or 250 consecutive residues of GBV-C E2.

3. The method of claim 1, wherein said peptide or polypeptide is about 232 or 250 residues in length.

4. The method of claim 1, wherein the peptide or polypeptide comprises a non-GBV-C E2 sequence.

5. The method of claim 4, wherein the non-GBV-C E2 sequence is a cell permeability peptide.

6. The method of claim 1, wherein the immune cell is a T cell or a B cell.

7. The method of claim 4, wherein the T cell is a helper T cell, a suppressor T cell, an NK cell or a killer T cell.

8. The method of claim 1, wherein said subject is a human.

9. The method of claim 1, wherein administering comprises intravenous, intra-arterial, oral, subcutaneous, topical or intraperitoneal administration.

10. The method of claim 1, further comprising administering a second anti-inflammatory agent.

11. The method of claim 1, wherein said peptide or polypeptide is administered at 0.1-500 mg/kg/d.

12. The method of claim 1, wherein said peptide or polypeptide is administered daily or weekly.

13. The method of claim 1, wherein said subject suffers from a T cell- or B-cell-mediated inflammatory disease or an IL-2-mediated inflammatory disease.

14. A method of inhibiting IL-2 release, inhibiting inflammation, and/or inhibiting STATS-mediated signaling in a mammalian subject comprising administering to said subject a peptide or polypeptide, said peptide or polypeptide comprising SEQ ID NO: 8 and no more than 250 consecutive residues of GBV-C E2.

15. A pharmaceutical formulation comprising an isolated peptide comprising (a) SEQ ID NO: 8 and no more than 250 consecutive residues of GBV-C E2 fused to a cell permeability peptide; and (b) a pharmaceutically acceptable diluent, carrier or buffer.

16. The pharmaceutical formulation of claim 15, wherein said peptide comprises 232 or 250 consecutive residues of GBV-C E2.

17. The pharmaceutical formulation of claim 15, wherein said peptide is about 232 or 250 residues in length.

18. The method of claim 5, wherein said cell permeability peptide is HIV TAT.

19. The pharmaceutical formulation of claim 15, wherein said cell permeability peptide is HIV TAT.

* * * * *

UNITED STATES PATENT AND TRADEMARK OFFICE
CERTIFICATE OF CORRECTION

PATENT NO. : 9,611,301 B2  
APPLICATION NO. : 14/384775  
DATED : April 4, 2017  
INVENTOR(S) : Jack T. Stapleton et al.

Page 1 of 1

It is certified that error appears in the above-identified patent and that said Letters Patent is hereby corrected as shown below:

On the Title Page

Item (73) Assignees, on the second line, delete "Iowa, IA" and replace with --Iowa City, IA-- therefor.

Signed and Sealed this  
Twenty-fifth Day of July, 2017

Joseph Matal  
*Performing the Functions and Duties of the*  
*Under Secretary of Commerce for Intellectual Property and*  
*Director of the United States Patent and Trademark Office*